US 8,637,449 B2

(12) United States Patent
Song et al.

(10) Patent No.: US 8,637,449 B2
(45) Date of Patent: Jan. 28, 2014

(54) PROCESSES FOR PREPARING PROTEASE INHIBITORS OF HEPATITIS C VIRUS

(75) Inventors: Zhiguo Jake Song, Edison, NJ (US); Yaling Wang, Westfield, NJ (US); David M. Tellers, Lansdale, PA (US); Laura M. Artino, Oakhurst, NJ (US); David R. Lieberman, London (GB)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/392,168

(22) PCT Filed: Aug. 26, 2010

(86) PCT No.: PCT/US2010/046725
§ 371 (c)(1),
(2), (4) Date: Feb. 24, 2012

(87) PCT Pub. No.: WO2011/025849
PCT Pub. Date: Mar. 3, 2011

(65) Prior Publication Data
US 2012/0232247 A1    Sep. 13, 2012

Related U.S. Application Data

(60) Provisional application No. 61/237,440, filed on Aug. 27, 2009.

(51) Int. Cl.
*A61K 38/00* (2006.01)
(52) U.S. Cl.
USPC .......................................................... 514/1.1
(58) Field of Classification Search
None
See application file for complete search history.

(56) References Cited

U.S. PATENT DOCUMENTS

| | | |
|---|---|---|
| 6,620,940 B1 | 9/2003 | Robey |
| 2002/0016294 A1 | 2/2002 | Venkatraman et al. |
| 2009/0155209 A1 | 6/2009 | Blatt et al. |

FOREIGN PATENT DOCUMENTS

| | | |
|---|---|---|
| WO | WO2007/015787 A1 | 2/2007 |
| WO | WO2007/015855 A1 | 2/2007 |
| WO | WO 2007015787 A1 * | 2/2007 |

OTHER PUBLICATIONS

Heck, Accounts of Chemical Research, 1979, vol. 12, p. 146-151.*

* cited by examiner

*Primary Examiner* — Marcela M Cordero Garcia
*Assistant Examiner* — Kaipeen Yang
(74) *Attorney, Agent, or Firm* — Henry P. Wu; Sheldon O. Heber

(57) ABSTRACT

The present invention relates to synthetic processes useful in the preparation of macrocyclic compounds of Formula (I) that are useful as inhibitors of the hepatitis C virus NS3 protease and have application in the treatment of conditions caused by the hepatitis C virus. The present invention also encompasses intermediates useful in the disclosed synthetic processes and the methods of their preparation.

26 Claims, 19 Drawing Sheets

```
                        SEQUENCE LISTING

<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: Protease Substrate
<221> NAME/KEY: ACETYLATION
<222> LOCATION: 1
<221> NAME/KEY: AMIDATION
<222> LOCATION: 11
<221> NAME/KEY: SITE
<222> LOCATION: 1
<223> OTHER INFORMATION: Europium label
<221> NAME/KEY: MOD_RES
<222> LOCATION: 7
<223> OTHER INFORMATION: Xaa = Abu
<221> NAME/KEY: SITE
<222> LOCATION: 8
<223> OTHER INFORMATION: Xaa = 2-hydroxy propanoic acid
<221> NAME/KEY: SITE
<222> LOCATION: (11)...(11)
<223> OTHER INFORMATION: QSY-7 label
<221> NAME/KEY: THIOLEST
<222> LOCATION: (7)...(8)

<400> SEQUENCE: 1

Cys Asp Asp Met Glu Glu Xaa Xaa Ser Ala Lys
 1               5                  10
```

PROCESSES FOR PREPARING PROTEASE INHIBITORS OF HEPATITIS C VIRUS

CROSS-REFERENCE TO RELATED APPLICATIONS

This application is a National Stage application of International Patent Application No. PCT/US2010/046725, filed Aug. 26, 2010, which claims priority to U.S. Provisional Patent Application No. 61/237,440, filed Aug. 27, 2009.

REFERENCE TO SEQUENCE LISTING SUBMITTED ELECTRONICALLY

The sequence listing of the present application is submitted electronically via EFS-Web as an ASCII formatted sequence listing with a file name "MRLIFD22448USPCT-SEQLIST-09MAY2012.TXT" and a size of 1023 bytes. This sequence listing submitted via EFS-Web is part of the specification and is herein incorporated by reference in its entirety.

FIELD OF THE INVENTION

The present invention relates to synthetic processes useful in the preparation of macrocyclic compounds that are useful as inhibitors of the hepatitis C virus NS3 protease and have application in the treatment of conditions caused by the hepatitis C virus. The present invention also encompasses intermediates useful in the disclosed synthetic processes and the methods of their preparation.

BACKGROUND OF THE INVENTION

Hepatitis C virus (HCV) infection is a major health problem that leads to chronic liver disease, such as cirrhosis and hepatocellular carcinoma, in a substantial number of infected individuals. Current treatments for HCV infection include immunotherapy with recombinant interferon-α alone or in combination with the nucleoside analog ribavirin.

Several virally-encoded enzymes are putative targets for therapeutic intervention, including a metalloprotease (NS2-3), a serine protease (NS3, amino acid residues 1-180), a helicase (NS3, full length), an NS3 protease cofactor (NS4A), a membrane protein (NS4B), a zinc metalloprotein (NS5A) and an RNA-dependent RNA polymerase (NS5B). The NS3 protease is located in the N-terminal domain of the NS3 protein, and is considered a prime drug target because it is responsible for an intramolecular cleavage at the NS3/4A site and for downstream intermolecular processing at the NS4A/4B, NS4B/5A and NS5A/5B junctions.

The compounds that can be prepared by the processes of this disclosure are effective as inhibitors of intermolecular cleavage at the NS3/4A site (referred to herein as "HCV NS3 inhibitors" or "HCV NS3 inhibitor compounds"). Such compounds are therefore useful in the treatment of hepatitis C viral infection and conditions caused by HCV. International Patent Application Publication WO2007/015855 and International Patent Application Publication WO2007/015787 describe macrocyclic compounds that are useful as HCV NS3 inhibitors and useful in the treatment of HCV and conditions caused by HCV infection. There is, therefore, a need for chemical processes for preparing compounds that are potent inhibitors of intermolecular cleavage at the NS3/4A site. This disclosure addresses this need.

SUMMARY OF THE INVENTION

The present invention relates to chemical processes useful in the synthesis of macrocyclic compounds of Formula I that are useful as inhibitors of the hepatitis C virus NS3 protease and have application in the treatment of conditions caused by the hepatitis C virus. The present invention also encompasses chemical processes that afford intermediates useful in the production of the macrocyclic compounds of Formula I and different forms of the compound of Formula III-205. The chemical processes of the present invention afford advantages over previously known procedures and include an efficient route to macrocyclic compounds of Formula I.

More particularly, the present invention relates to processes for preparing compounds of Formula I,

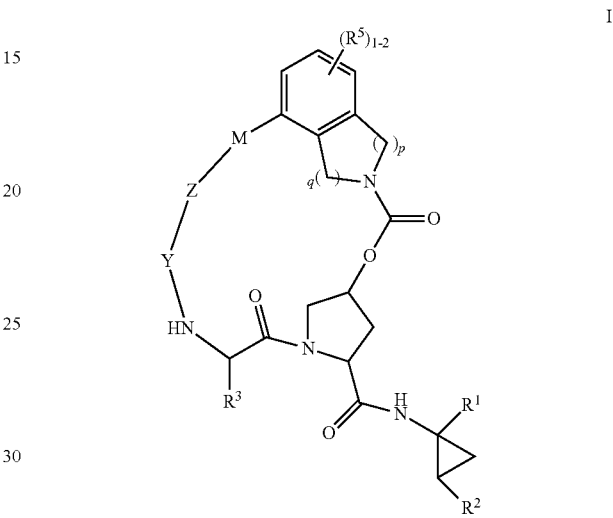

or pharmaceutically acceptable salts or hydrates thereof, wherein:
p and q are independently 1 or 2;
$R^1$ is $CO_2R^{10}$, $CONR^{10}SO_2R^6$, $CONR^{10}SO_2NR^8R^9$, or tetrazolyl;
$R^2$ is $C_1$-$C_6$ alkyl, $C_2$-$C_6$ alkenyl or $C_3$-$C_8$ cycloalkyl, wherein the alkyl, alkenyl or cycloalkyl is substituted with from 0 to 3 halo;
$R^3$ is $C_1$-$C_8$ alkyl, $C_3$-$C_8$ cycloalkyl, $C_3$-$C_8$ cycloalkyl($C_1$-$C_8$)alkyl, aryl($C_1$-$C_8$)alkyl, or Het, wherein aryl is phenyl or naphthyl and the alkyl, cycloalkyl, or aryl is substituted with from 0 to 3 substituents selected from the group consisting of halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $NO_2$, $CN$, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, $C(O)R^{10}$, and $CON(R^{10})_2$;
Het is a 5- or 6-membered saturated cyclic ring having 1 or 2 heteroatoms selected from N, O and S, wherein the ring is substituted with from 0 to 3 substituents selected from halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $NO_2$, $CN$, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, $C(O)R^{10}$, and $CON(R^{10})_2$;
$R^4$ is H, $C_1$-$C_8$ alkyl, $C_3$-$C_8$ cycloalkyl($C_1$-$C_8$)alkyl, or aryl ($C_1$-$C_8$)alkyl; wherein aryl is phenyl or naphthyl and the alkyl, cycloalkyl, or aryl is substituted with from 0 to 3 substituents selected from the group consisting of halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $NO_2$, $CN$, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, $C(O)R^{10}$, and $CON(R^{10})_2$;

$R^5$ is H, halo, $OR^{10}$, $C_1$-$C_6$ alkyl, CN, $CF_3$, $SR^{10}$, $SO_2(C_1$-$C_6$ alkyl), $C_3$-$C_8$ cycloalkyl, $C_3$-$C_8$ cycloalkoxy, $C_1$-$C_6$ haloalkyl, $N(R^7)_2$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein the aryl, heteroaryl, heterocyclyl, cycloalkyl, cycloalkoxy, or alkyl is substituted with from 0 to 4 substituents selected from the group consisting of halo, $OR^{10}$, $SR^{10}$, $N(R^7)_2$, $N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $C_3$-$C_6$ cycloalkyl, $C_3$-$C_6$ cycloalkoxy, $NO_2$, CN, $CF_3$, $SO_2(C_1$-$C_6$ alkyl), $NR^{10}SO_2R^6$, $SO_2N(R^6)_2$, $S(O)(C_1$-$C_6$ alkyl), $NHCOOR^6$, $NHCOR^6$, $NHCONHR^6$, $CO_2R^{10}$, $C(O)R^{10}$, and $CON(R^{10})_2$; wherein 2 adjacent substituents of the cycloalkyl, cycloalkoxy, aryl, heteroaryl or heterocyclyl, if present, are optionally taken together to form a 3- to 6-membered cyclic ring containing from 0 to 3 heteroatoms selected from N, O and S;

$R^6$ is $C_1$-$C_6$ alkyl, $C_3$-$C_6$ cycloalkyl, $C_3$-$C_6$ cycloalkyl($C_1$-$C_5$)alkyl, aryl, aryl($C_1$-$C_4$)alkyl, heteroaryl, heteroaryl($C_1$-$C_4$ alkyl), heterocyclyl, or heterocyclyl($C_1$-$C_8$ alkyl), wherein the alkyl, cycloalkyl, aryl, heteroaryl, or heterocyclyl is substituted with 0 to 2 W substituents; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

Y is C(=O), $SO_2$, or C(=N—CN);

Z is $C(R^{10})_2$, O, or $N(R^4)$;

M is $C_1$-$C_{12}$ alkylene, wherein the M alkylene is substituted with from 0 to 2 substituents selected from the group consisting of $C_1$-$C_8$ alkyl, $C_3$-$C_8$ cycloalkyl($C_1$-$C_8$ alkyl), and aryl($C_1$-$C_8$ alkyl); and 2 adjacent substituents of M, if present, are optionally taken together to form a 3- to 6-membered cyclic ring containing from 0 to 3 heteroatoms selected from N, O and S;

each $R^7$ is independently H, $C_1$-$C_6$ alkyl, $C_3$-$C_6$ cycloalkyl, $C_3$-$C_6$ cycloalkyl($C_1$-$C_5$)alkyl, aryl, aryl($C_1$-$C_4$)alkyl, heteroaryl, heteroaryl($C_1$-$C_4$ alkyl), heterocyclyl, or heterocyclyl($C_1$-$C_8$ alkyl), wherein the alkyl, cycloalkyl, aryl, heteroaryl, or heterocyclyl is substituted with from 0 to 2 W substituents; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

each W is independently halo, $OR^{10}$, $C_1$-$C_6$ alkyl, CN, $CF_3$, $NO_2$, $SR^{10}$, $CO_2R^{10}$, $CON(R^{10})_2$, $C(O)R^{10}$, $N(R^{10})C(O)R^{10}$, $SO_2(C_1$-$C_6$ alkyl), $S(O)(C_1$-$C_6$ alkyl), $C_3$-$C_8$ cycloalkyl, $C_3$-$C_8$ cycloalkoxy, $C_1$-$C_6$ haloalkyl, $N(R^{10})_2$, $N(C_1$-$C_6$ alkyl)$O(C_1$-$C_6$ alkyl), halo($C_1$-$C_6$ alkoxy), $NR^{10}SO_2R^{10}$, $SO_2N(R^{10})_2$, $NHCOOR^{10}$, $NHCONHR^{10}$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen;

$R^8$ is $C_1$-$C_8$ alkyl, $C_3$-$C_8$ cycloalkyl, $C_3$-$C_8$ cycloalkyl($C_1$-$C_8$ alkyl), aryl, aryl($C_1$-$C_4$ alkyl), heteroaryl, heterocyclyl, heteroaryl($C_1$-$C_4$ alkyl), or heterocyclyl($C_1$-$C_8$ alkyl), wherein the alkyl, cycloalkyl, aryl, heteroaryl or heterocyclyl is substituted with from 0 to 4 substituents selected from the group consisting of aryl, $C_3$-$C_8$ cycloalkyl, heteroaryl, heterocyclyl, $C_1$-$C_6$ alkyl, halo($C_1$-$C_6$ alkoxy), halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C(O)R^{10}$, $C_1$-$C_6$ haloalkyl, $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, and $C(O)N(R^{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein 2 adjacent substituents of the cycloalkyl, cycloalkoxy, aryl, heteroaryl or heterocyclyl, if present, are optionally taken together to form a 3- to 6-membered cyclic ring containing from 0 to 3 heteroatoms selected from N, O and S;

$R^9$ is $C_1$-$C_8$ alkyl, $C_3$-$C_8$ cycloalkyl, $C_3$-$C_8$ cycloalkyl($C_1$-$C_8$ alkyl), $C_1$-$C_8$ alkoxy, $C_3$-$C_8$ cycloalkoxy, aryl, aryl($C_1$-$C_4$ alkyl), heteroaryl, heterocyclyl, heteroaryl($C_1$-$C_4$ alkyl), or heterocyclyl($C_1$-$C_8$ alkyl), wherein the alkyl, cycloalkyl, alkoxy, cycloalkoxy, aryl, heteroaryl or heterocyclyl is substituted with from 0 to 4 substituents selected from the group consisting of aryl, $C_3$-$C_8$ cycloalkyl, heteroaryl, heterocyclyl, $C_1$-$C_6$ alkyl, halo($C_1$-$C_6$ alkoxy), halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C(O)R^{10}$, $C_1$-$C_6$ haloalkyl, $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, and $C(O)N(R^{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein 2 adjacent substituents of the cycloalkyl, cycloalkoxy, aryl, heteroaryl or heterocyclyl, if present, are optionally taken together to form a 3- to 6-membered cyclic ring containing from 0 to 3 heteroatoms selected from N, O and S;

or $R^8$ and $R^9$ are optionally taken together, with the nitrogen atom to which they are attached, to form a 4- to 8-membered monocyclic ring containing from 0 to 2 additional heteroatoms selected from N, O and S; and each $R^{10}$ is independently H or $C_1$-$C_6$ alkyl;

the process comprising a) coupling a compound of structural formula IA with a compound of structural formula IB to form a compound of structural formula IC

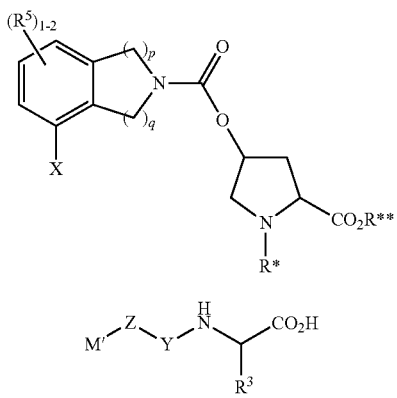

IA

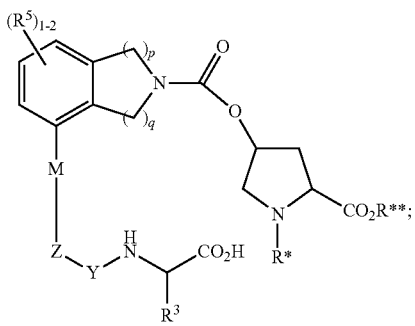

IB

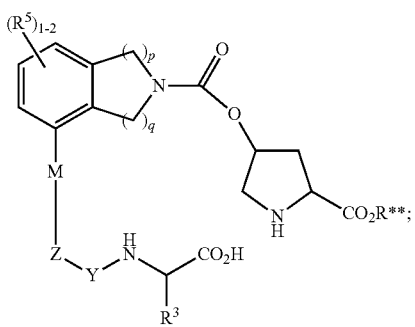

IC wherein
R* is selected from the group consisting of carbobenzyloxy, tert-butyloxycarbonyl, and 9H-fluoren-9-yl-methoxycarbonyl;
R** is selected from the group consisting of $C_1$-$C_8$ alkyl;
X is selected from the group consisting of halides and sulfonides; and
M' is a $C_2$-$C_{12}$ alkyl group containing from 0 to 2 double bonds and 0 to 1 triple bonds, wherein one of the double bonds or triple bonds is between $C_1$ and $C_2$ of the M' and the $C_2$-$C_{12}$ alkyl group is substituted with from 0 to 2 substituents selected from the group consisting of $C_1$-$C_8$ alkyl, $C_3$-$C_8$ cycloalkyl($C_1$-$C_8$ alkyl), and aryl($C_1$-$C_8$ alkyl); and 2 adjacent substituents of M', if present, are optionally taken together to form a 3- to 6-membered cyclic ring containing from 0 to 3 heteroatoms selected from N, O and S;
b) hydrogenating the compound of structural formula IC to form a compound of structural formula ID

ID

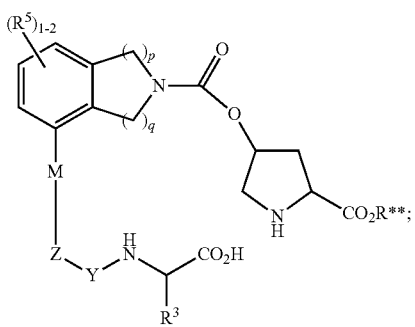

c) cyclizing said compound of structural formula ID to form a compound of structural formula IE

IE

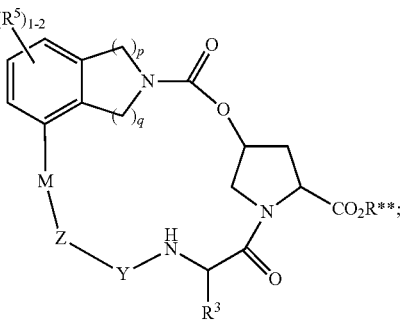

d) hydrolyzing the compound of structural formula IE to provide a compound of structural formula IF

IF

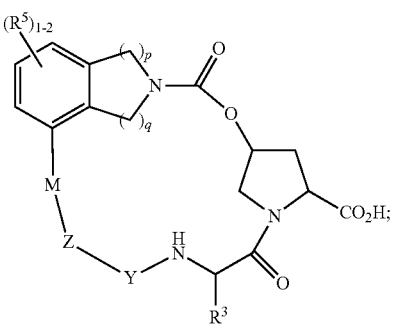

and
e) reacting the compound of structural formula IF with a compound of structural formula IG to provide the compound of Formula I;

IG

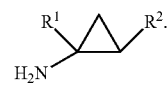

DETAILED DESCRIPTION OF THE INVENTION

Figure 1:
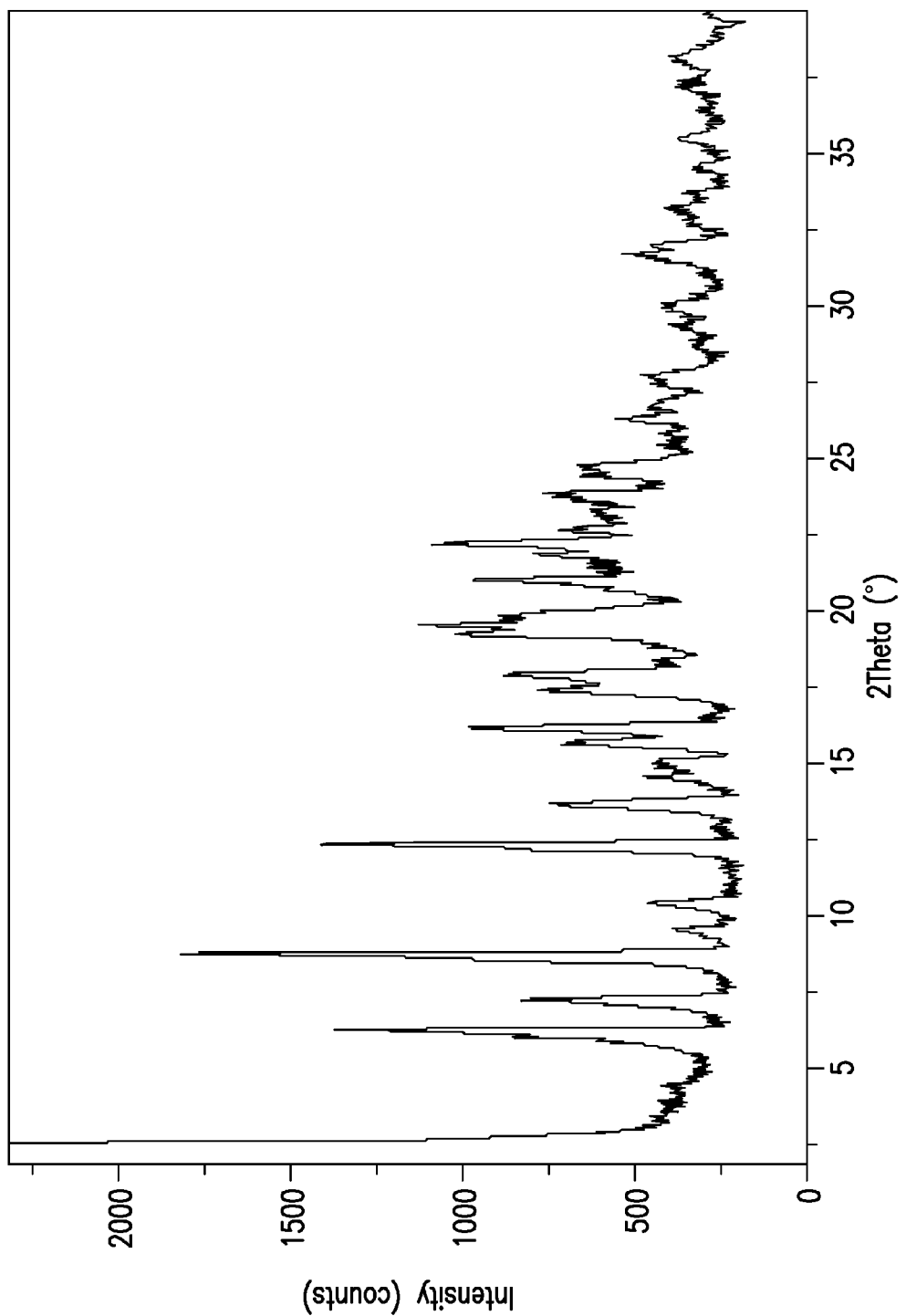
FIG. 1 is the XRPD pattern for ethanol solvate A of a potassium salt of exemplary Compound III-205.

A first embodiment of the invention is directed to processes in which X is selected from the group consisting of chloride, bromide, iodide, methane sulfonate, trifluoromethane sulfonate, and aryl sulfonates. In this embodiment, all other groups are as provided in the general process above.

A second embodiment of the invention is directed to processes in which M' of the compound of structural formula IB contains from 1 to 2 double bonds, wherein one of the double bonds, and the coupling comprises reacting the compound of structural formula IB with the compound of the structural formula IC in the presence of a palladium-based catalyst. In all aspects of this second embodiment, all other groups are as provided in the general process above and/or in the first embodiment.

In a first aspect of the second embodiment of the invention, the palladium-based catalyst is a palladium complex. In instances of the first aspect of the second embodiment, the palladium complex is a palladium-phosphine complex.

In a second aspect of the second embodiment of the invention, the palladium-based catalyst is selected from the group consisting of tetrakis(triphenylphosphine)palladium(0), bis(triphenylphosphine)palladium(II)chloride, bis(triphenylphosphine)palladium(II)acetate, bis(tri-tert-butylphosphine)palladium(0), bis(tricyclohexylphosphine)palladium(0), palladium bis(diphenylphosphinyl ferrocene)dichloride, palladium bis-(di-tert-butylphosphineyl ferrocene)dichloride, palladium(II)acetate, palladium(II)chloride, bis(benzonitrile)palladium(II)chloride, tris(dibenzylideneacetone)dipalladium(0), bis(dibenzylideneacetone)dipalladium, and palladium on carbon.

A third embodiment of the invention is directed to processes in which M' of the compound of structural formula IB contains from 0 or 1 double bond and 1 triple bond, wherein the double triple bond is between $C_1$ and $C_2$ of the M', and the coupling comprises reacting the compound of structural formula IB with a compound of the structural formula IC in the presence of a palladium-based catalyst and a copper salt. In all aspects of this third embodiment, all other groups are as provided in the general process above and/or in the first embodiment.

In a first aspect of the third embodiment of the invention, the palladium-based catalyst is a palladium complex. In particular instances, the palladium-based catalyst is selected from the group consisting of tetrakis(triphenylphosphine)palladium(0), bis(triphenylphosphine)palladium(II)chloride, bis(triphenylphosphine)palladium(II)acetate, bis(tri-tert-butylphosphine)palladium(0), bis(tricyclohexylphosphine)palladium(0), palladium bis(diphenylphosphinyl ferrocene)dichloride, palladium bis-(di-tert-butylphosphineyl ferrocene)dichloride, palladium(II)acetate, palladium(II)chloride, bis(benzonitrile)palladium(II)chloride, tris(dibenzylideneacetone)dipalladium(0), bis(dibenzylideneacetone)dipalladium, 2-dicyclohexyl phosphine-2',4',6'-triisopropyl biphenyl and palladium on carbon.

In a second aspect of the third embodiment of the invention, the copper salt is selected from the group consisting of copper(I) salts. In particular instances, the copper(I) salt is selected from the group consisting of copper(I)bromide, copper(I)chloride, capper(I)iodide and copper(I)trifluoromethane sulfonate. In preferred instances, the copper(I) salt is selected from the group consisting of copper(I)iodide.

A fourth embodiment of the invention is directed to processes in which the hydrogenating of step b comprises reacting the compound of structural formula IC with hydrogen gas in the presence of a catalyst. In a first aspect of this embodiment, the catalyst is palladium on carbon. In a second aspect of this embodiment, the hydrogenating is conducted at a temperature of from 10° C. to 50° C., and the hydrogen gas is provided at a pressure of from 5 psi to 100 psi. In all aspects of this fourth embodiment, all other groups are as provided in the general process above and/or in any of the first through third embodiments above.

A fifth embodiment of the invention is directed to processes in which R* is tert-butyloxycarbonyl, and the hydrogenating of step b comprises reacting the compound of structural formula IC with an acid to produce a compound of structural formula IC'

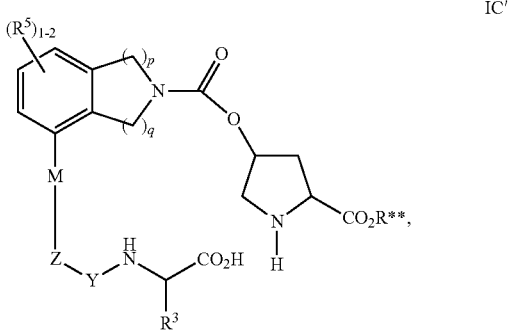

and hydrogenating the compound of structural formula IC' to produce the compound of structural formula ID. In a first aspect of this embodiment, the acid is selected from the group consisting of methanesulfonic acid and TFA. In all aspects of this fifth embodiment, all other groups are as provided in the general process above and/or in any of the first through fourth embodiments above.

A sixth embodiment of the invention is directed to processes in which the cyclizing of step c comprises reacting the compound of structural formula ID with N-(3-dimethylaminopropyl)-N'-ethylcarbodiimide or O-(7-azabenzotriazol-1-yl)-N,N,N',N'-tetramethyluronium dexafluorophosphate. In this sixth embodiment, all other groups are as provided in the general process above and/or in any of the first through fifth embodiments above.

A seventh embodiment of the invention is directed to processes in which p and q are both 1; $R^1$ is $CONR^{10}SO_2R^6$; $R^2$ is $C_1$-$C_6$ alkyl or $C_2$-$C_6$ alkenyl; $R^3$ is $C_5$-$C_6$ cycloalkyl or $C_1$-$C_8$ alkyl substituted with from 0 to 3 halo substitutents; $R^5$ is H, F or Cl; $R^6$ is $C_3$-$C_6$ cycloalkyl; Y is C(=O); Z is O, $CH_2$, NH or N($CH_3$); M is $C_1$-$C_8$ alkylene, wherein the M alkylene is substituted with from 0 to 2 substituents selected from the group consisting of $C_1$-$C_8$ alkyl, $C_3$-$C_8$ cycloalkyl($C_1$-$C_8$ alkyl) or aryl($C_1$-$C_8$ alkyl), and 2 adjacent substituents of M, if present, are optionally taken together to form a 3- to 6-membered cyclic ring containing from 0 to 2 heteroatoms selected from N, O, and S; and $R^{10}$ is H or $C_1$-$C_6$ alkyl. In this seventh embodiment, all other groups are as provided in the general process above and/or in any of the first through sixth embodiments above.

An eighth embodiment of the invention is directed to processes in which the compound of Formula I is selected from the group consisting of

III-5

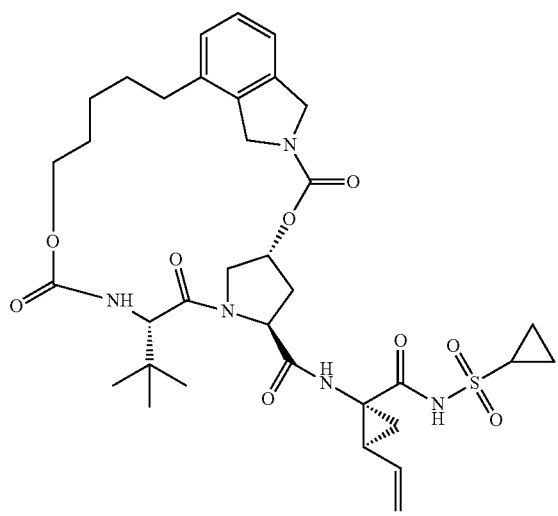

III-6

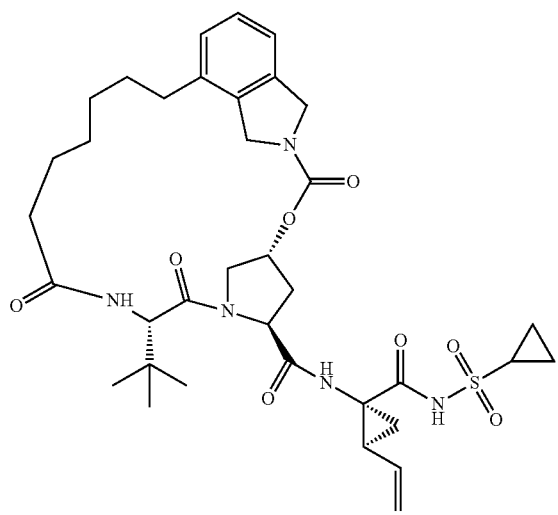

-continued

III-7

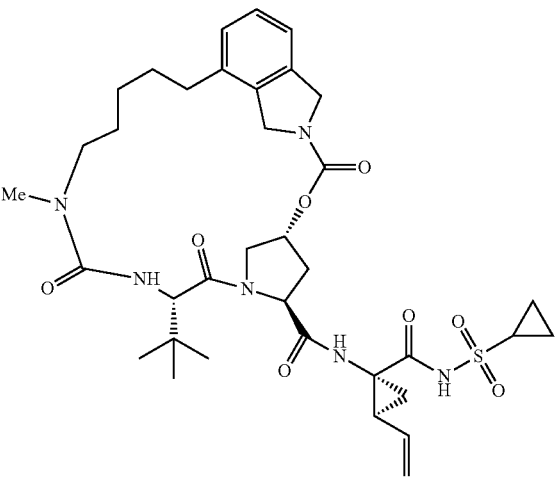

III-35

III-36

III-37
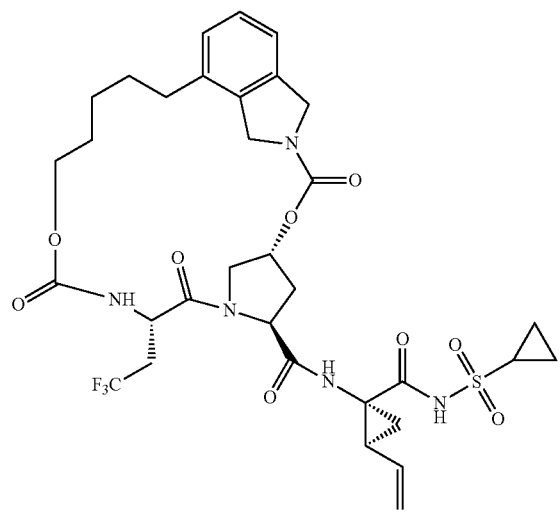
III-38
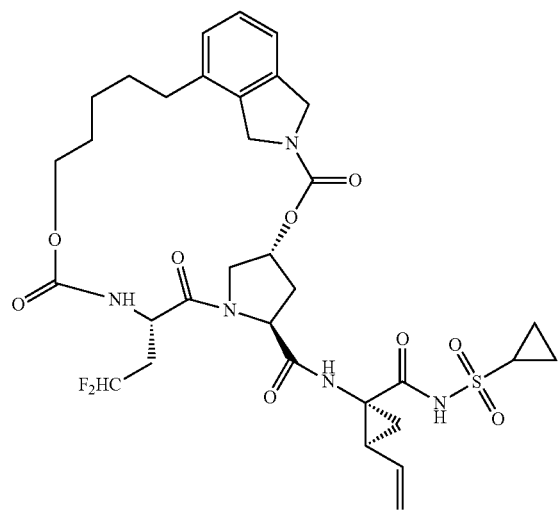
III-39
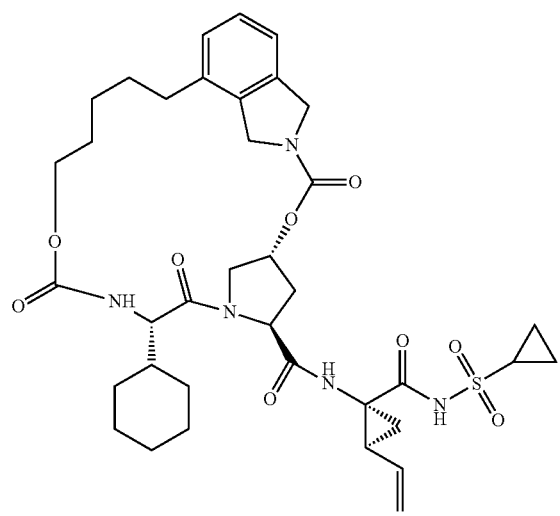
III-40
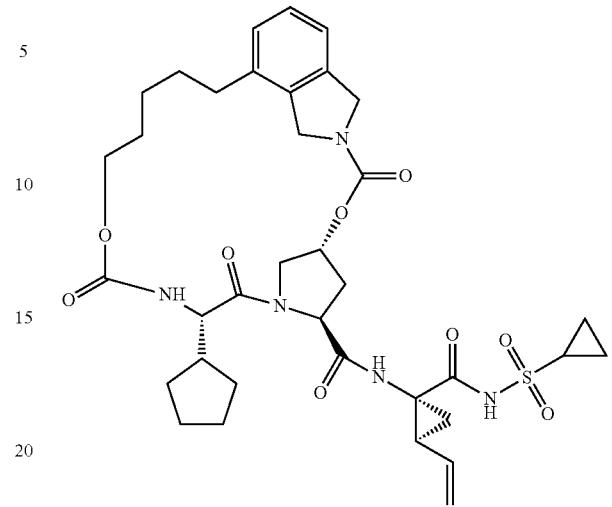
III-41
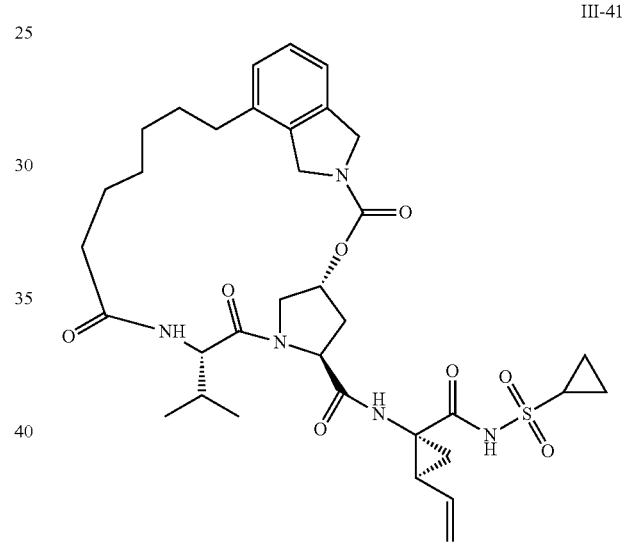
III-42
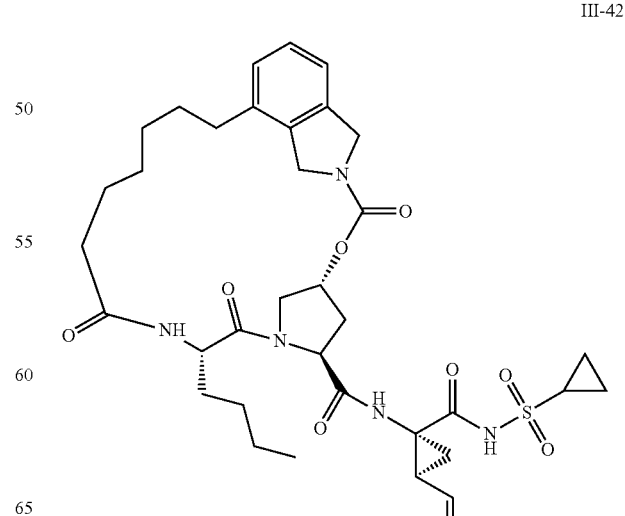

III-43
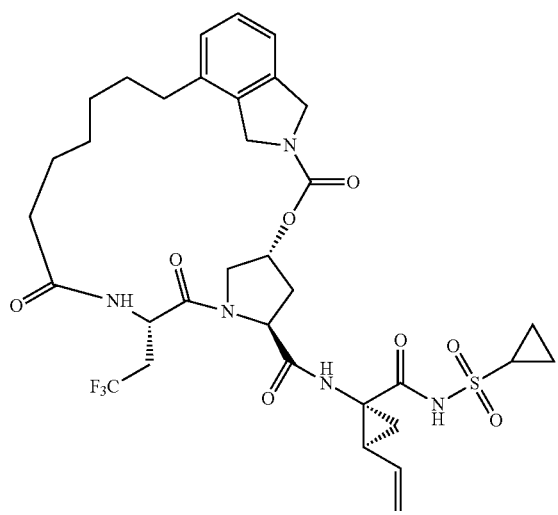
III-46
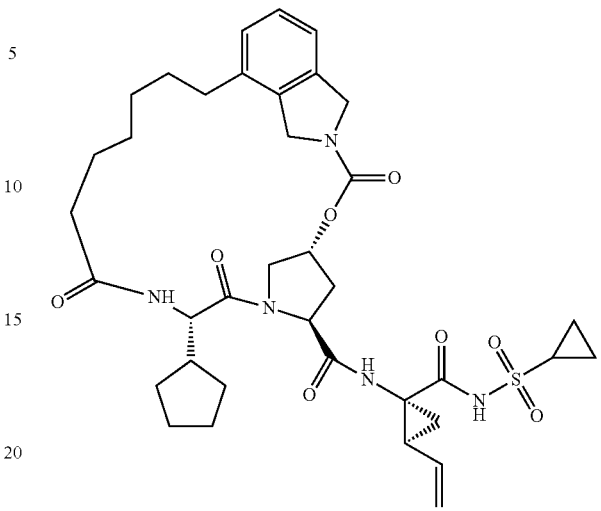
III-44
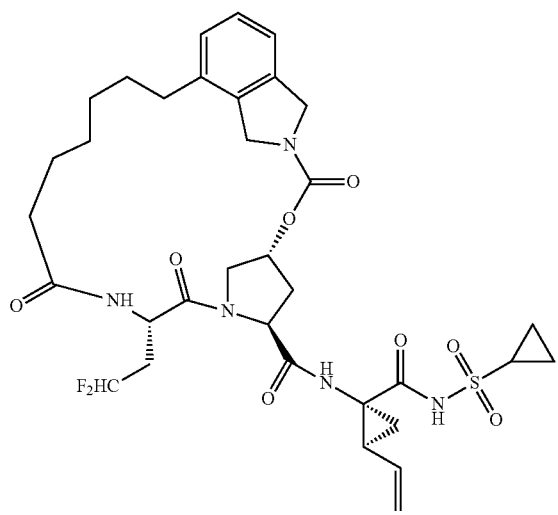
III-47
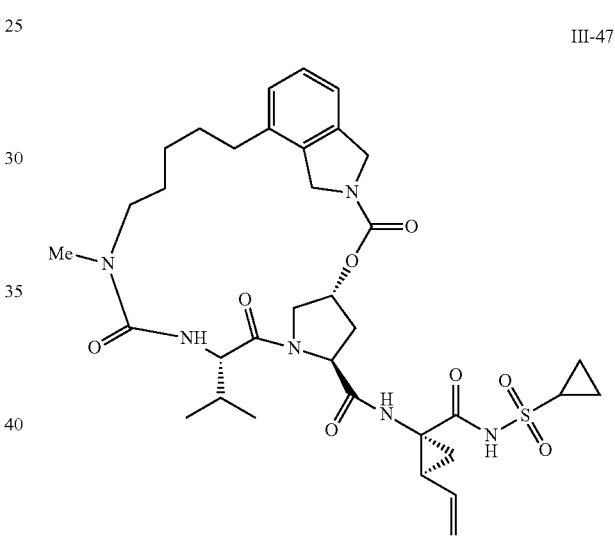
III-45
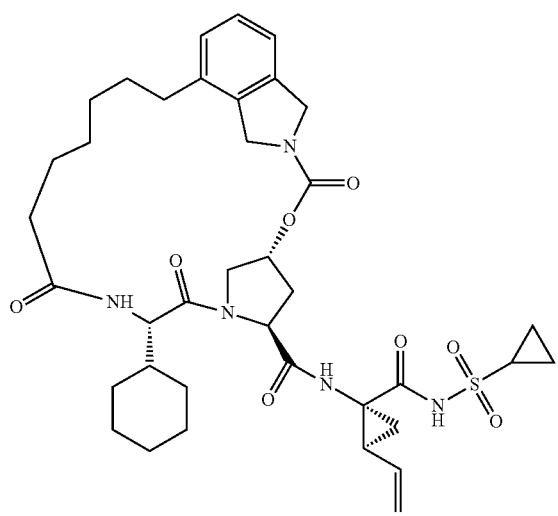
III-48
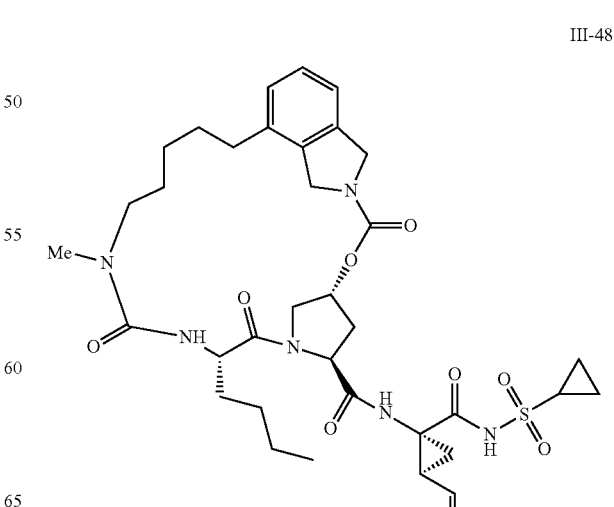

III-49
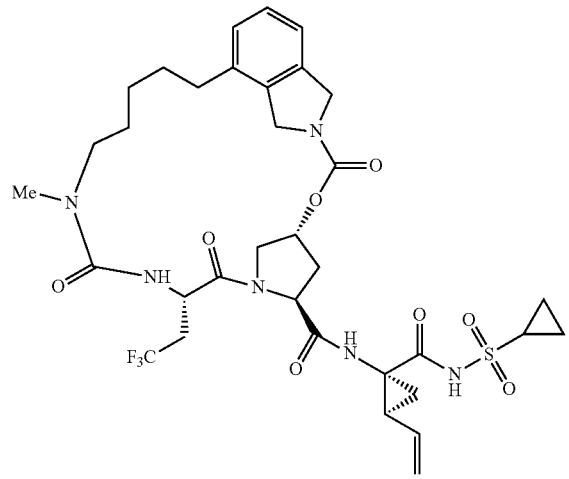
III-52
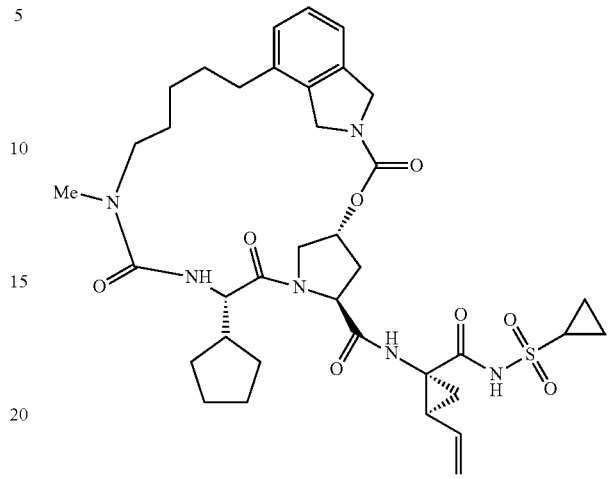
III-50
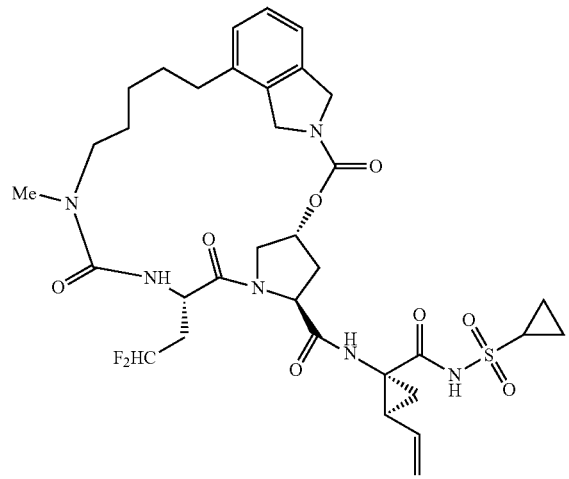
III-71
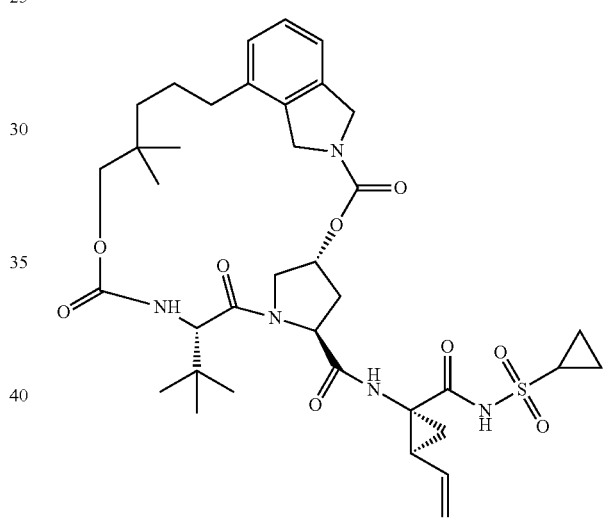
III-51
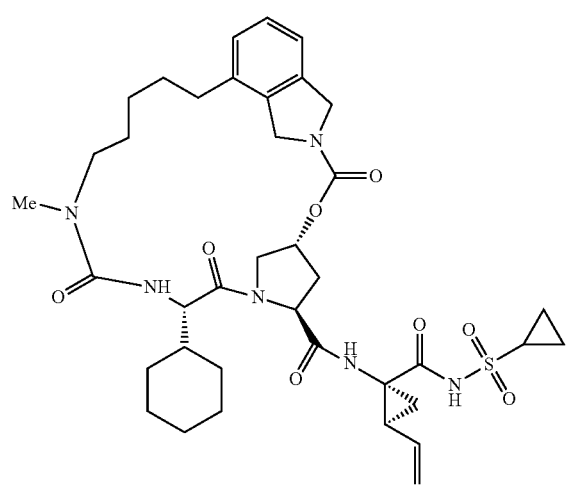
III-72
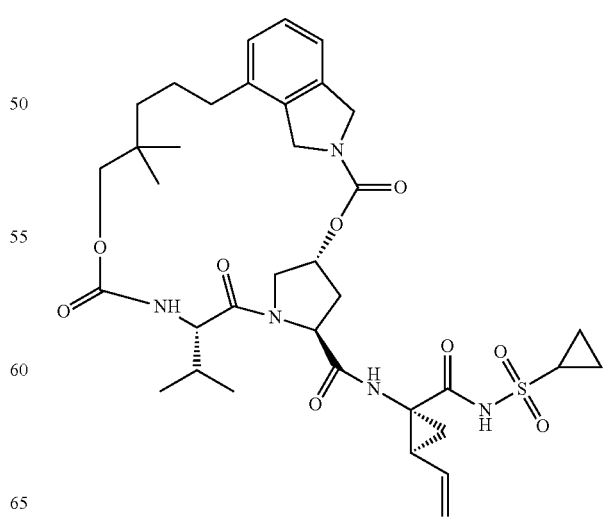

III-73
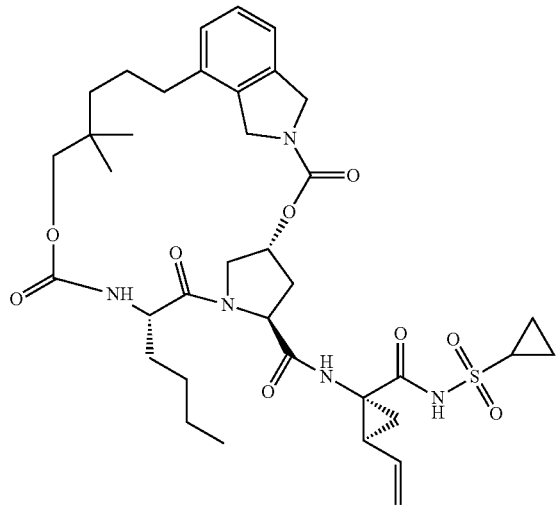
III-76
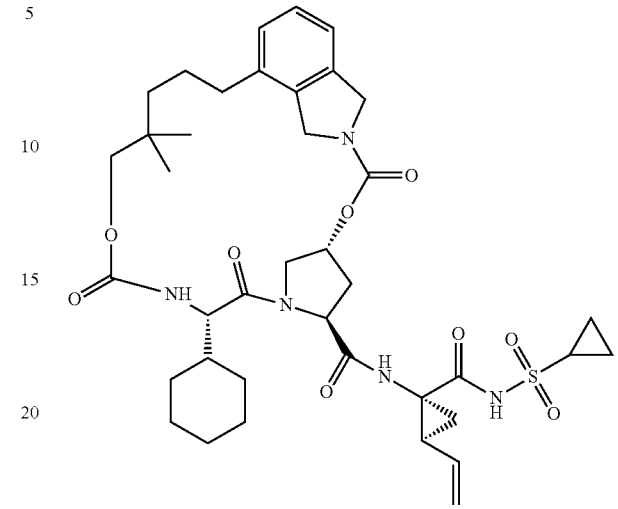
III-74
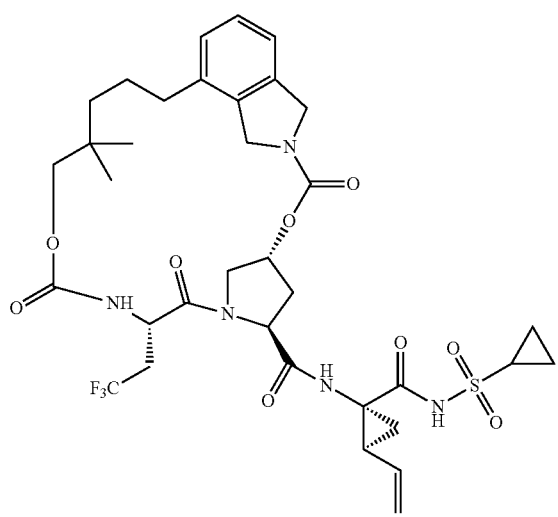
III-77
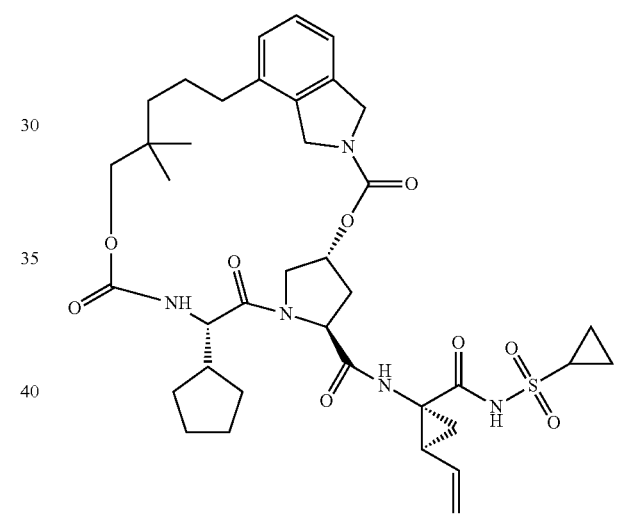
III-75
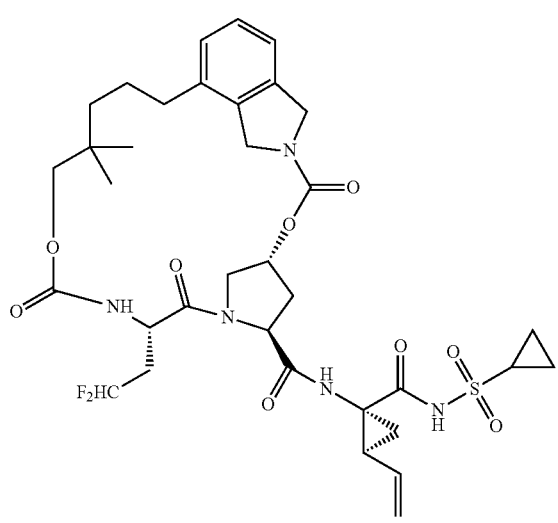
III-78
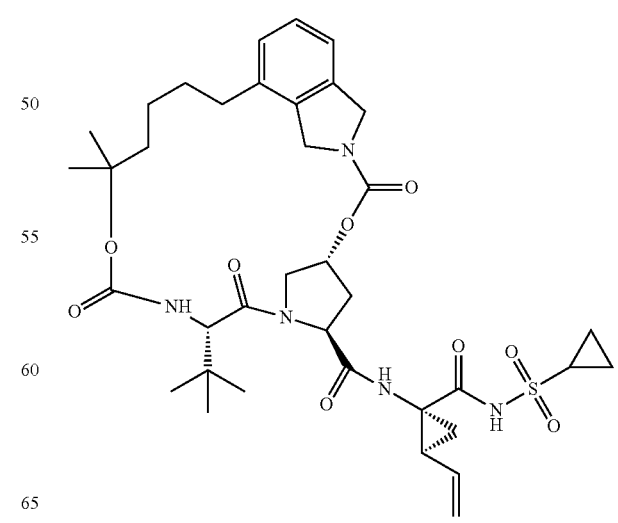

III-79
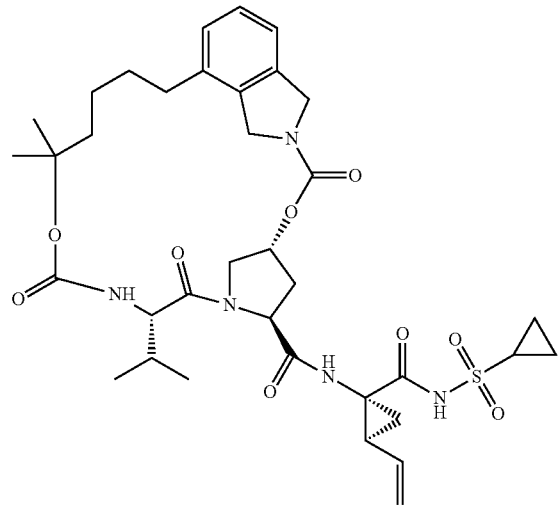
III-82
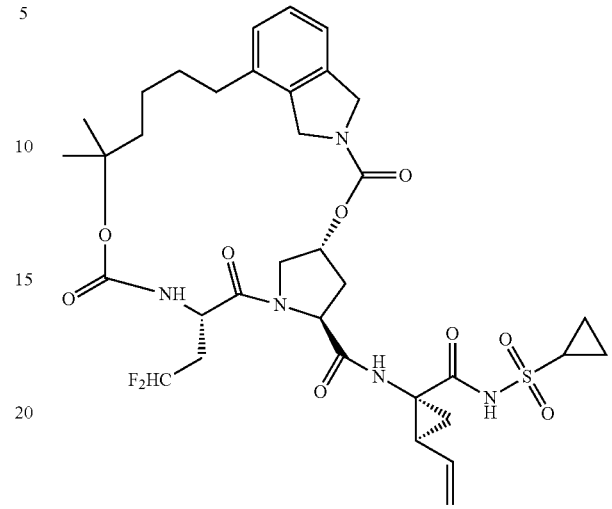
III-80
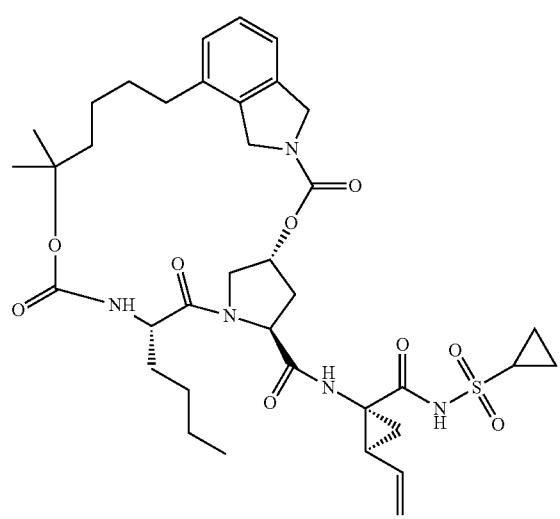
III-83
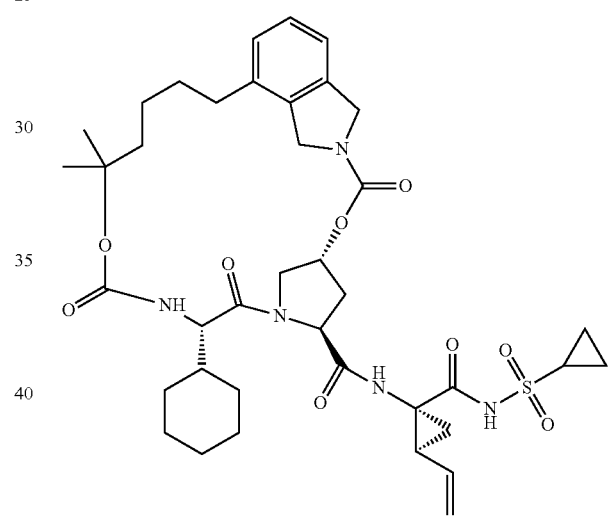
III-81
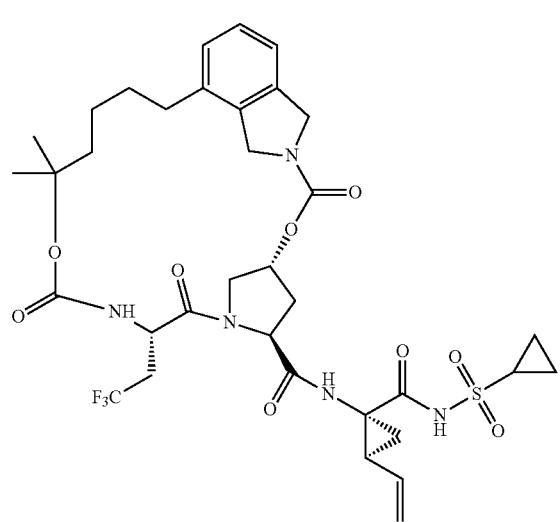
III-84
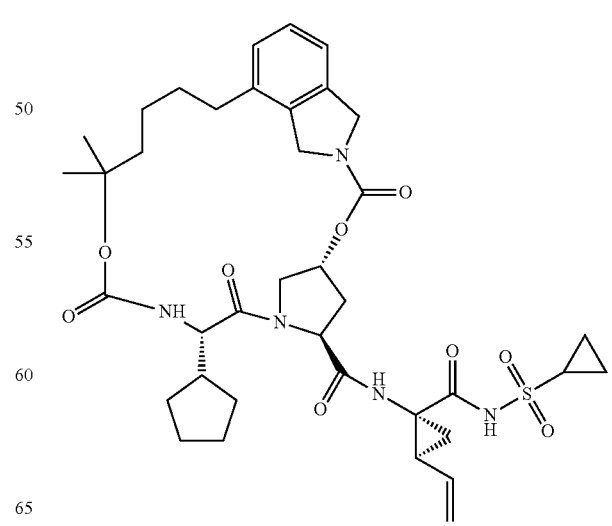

III-85
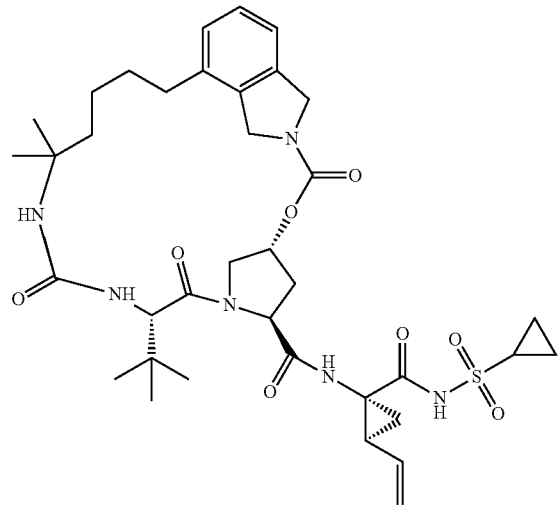
III-88
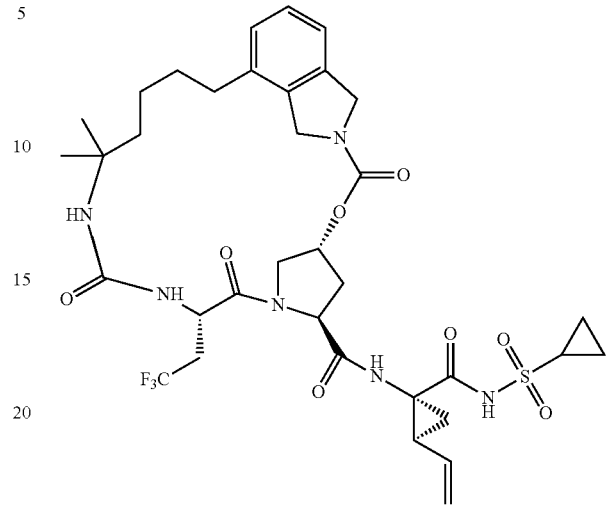
III-86
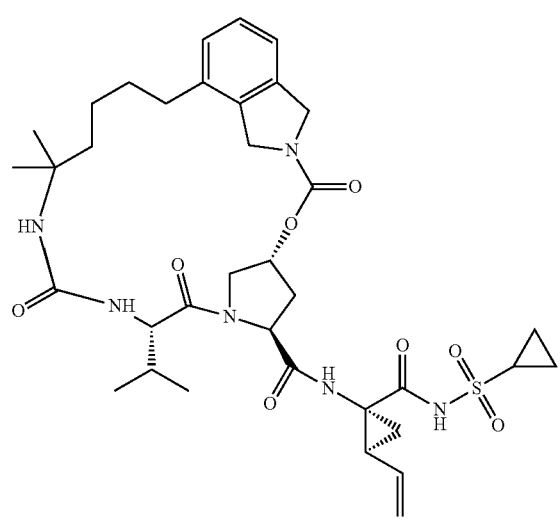
III-89
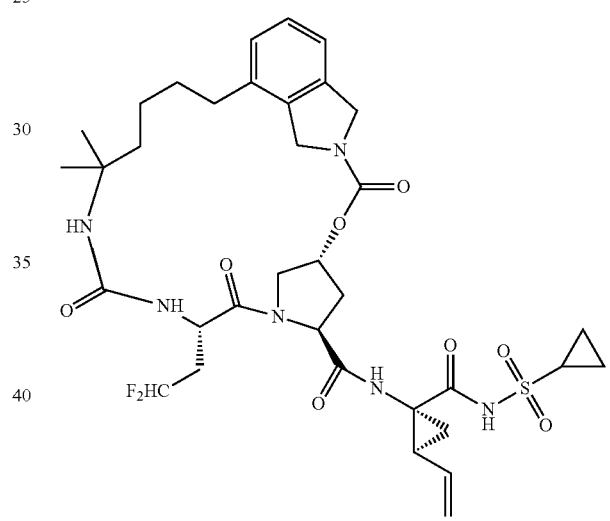
III-87
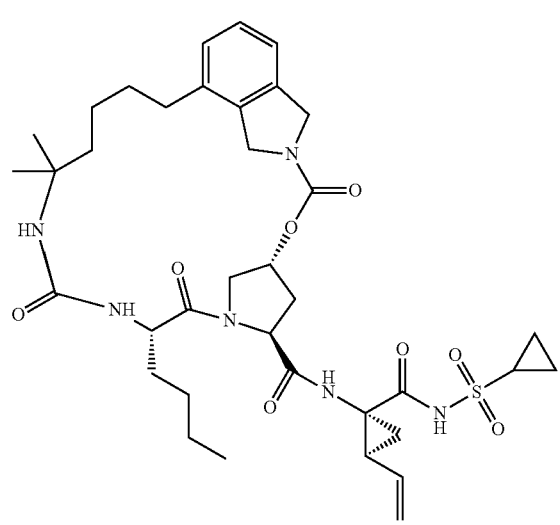
III-90
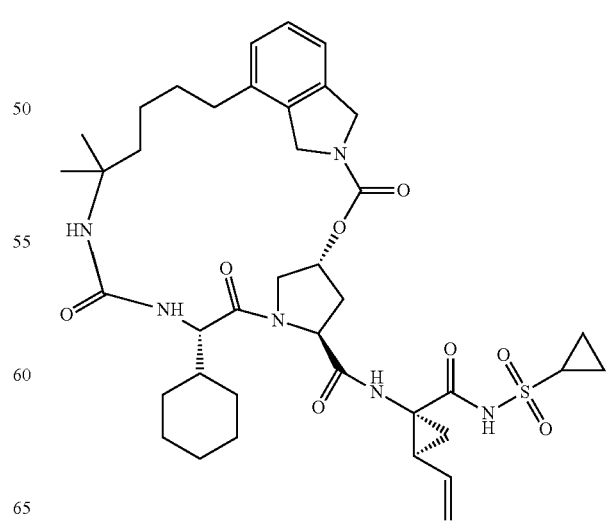

III-91
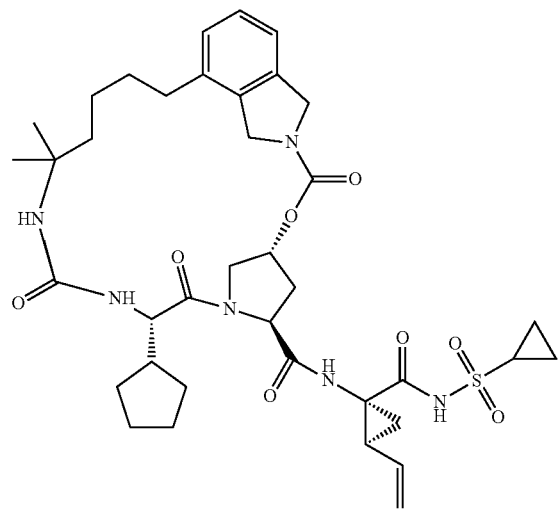
III-113
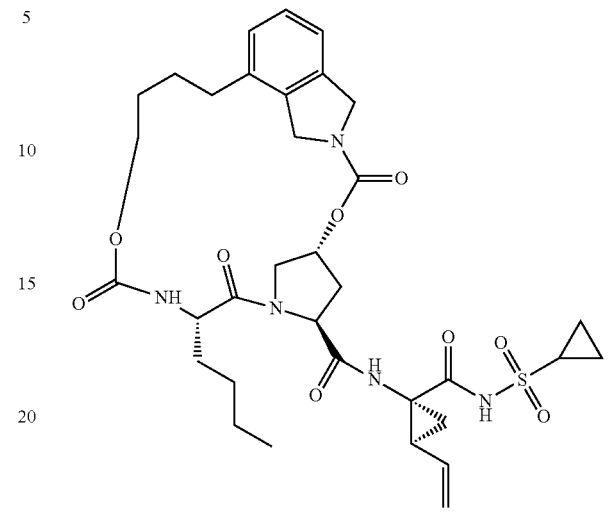
III-111
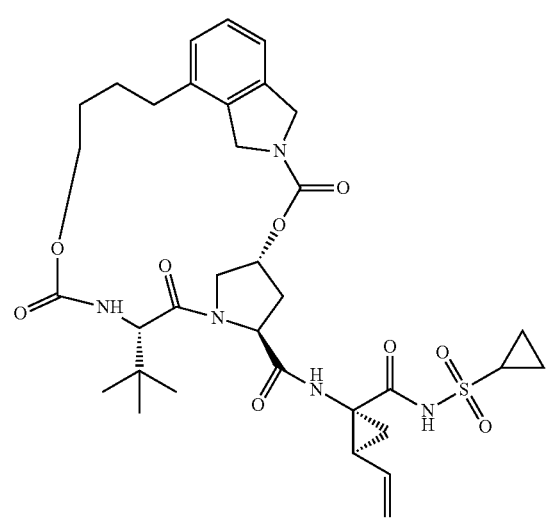
III-114
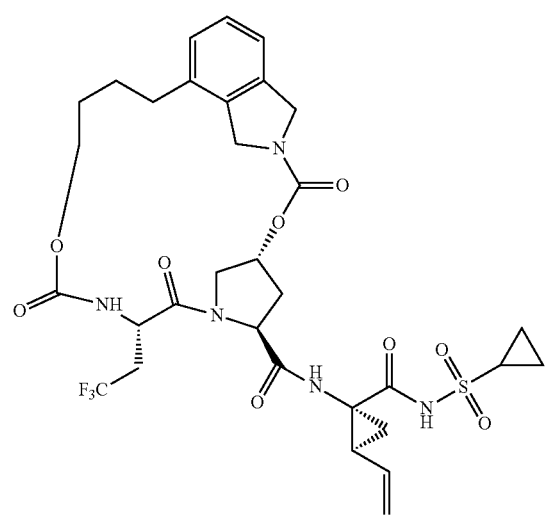
III-112
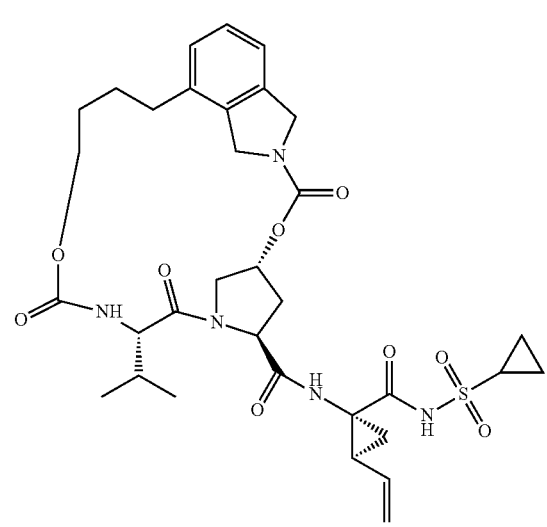
III-115
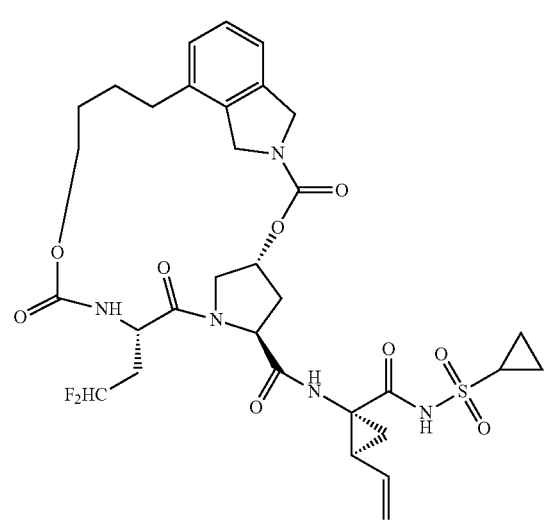

III-116
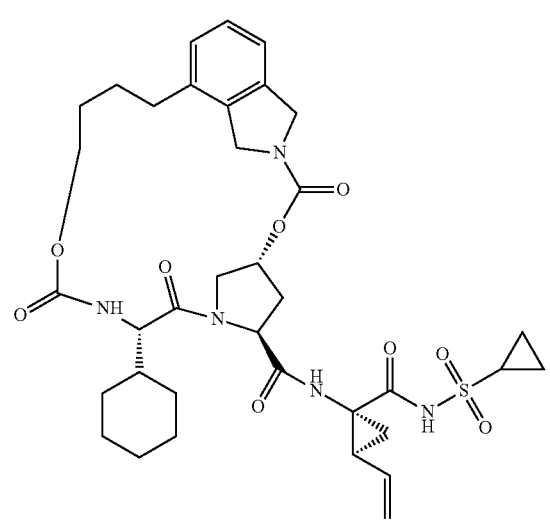
III-117
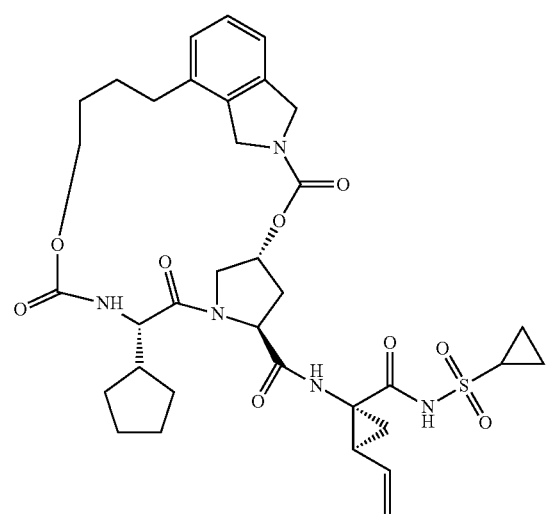
III-118
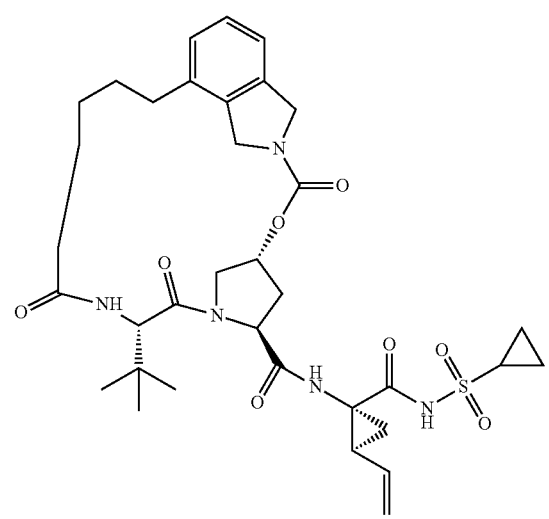
III-119
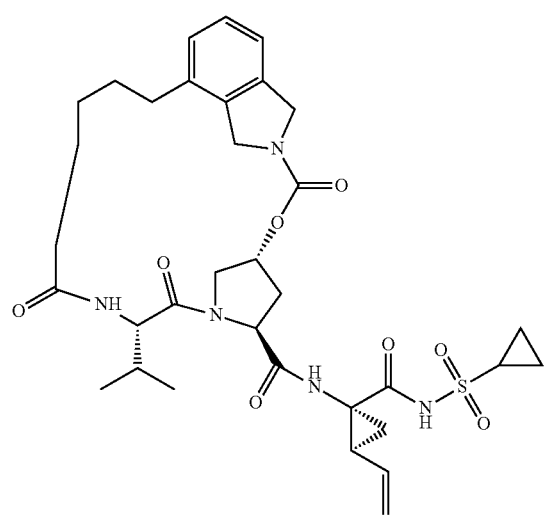
III-120
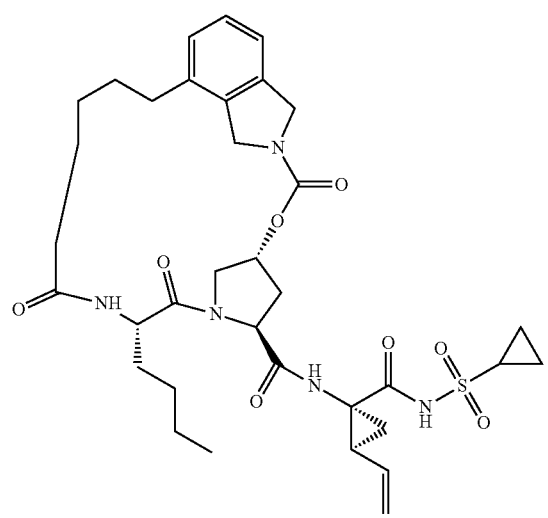
III-121
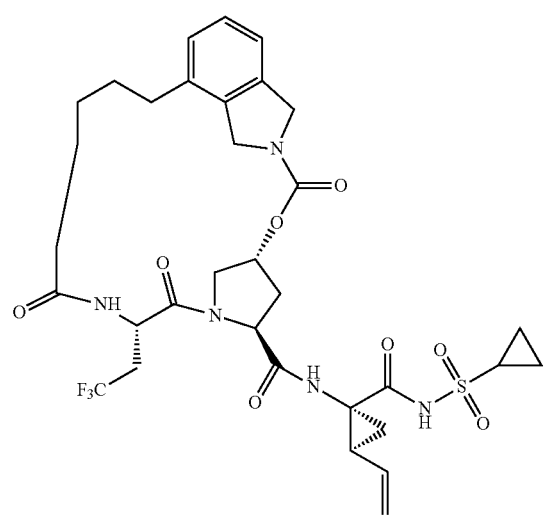

III-122
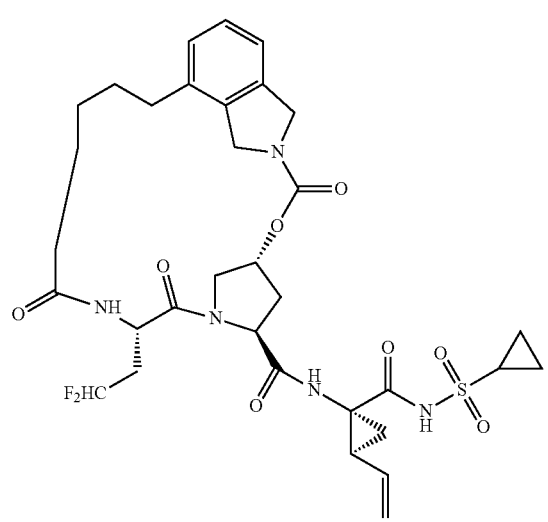
III-123
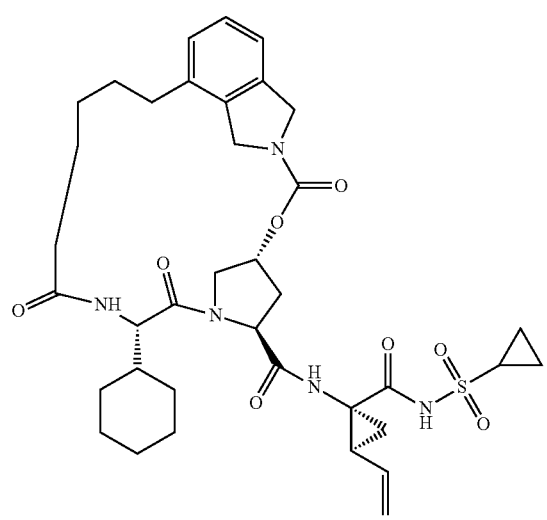
III-124
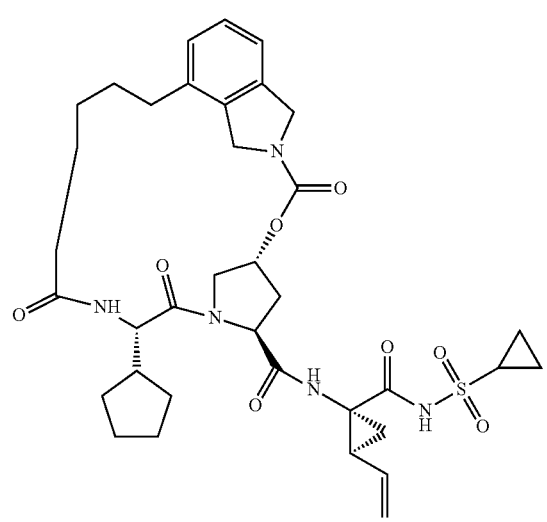
III-125
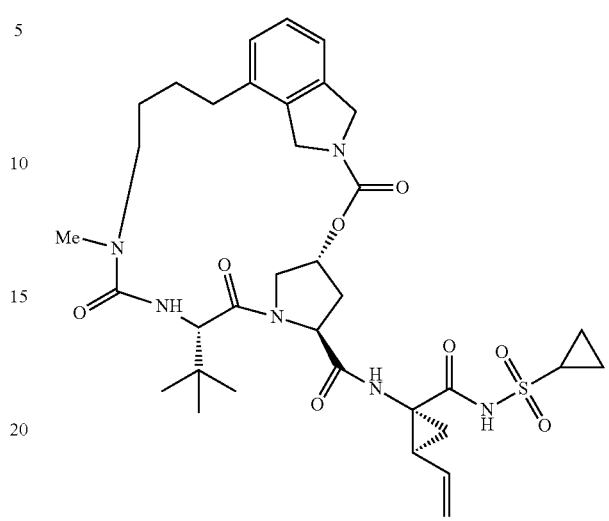
III-126
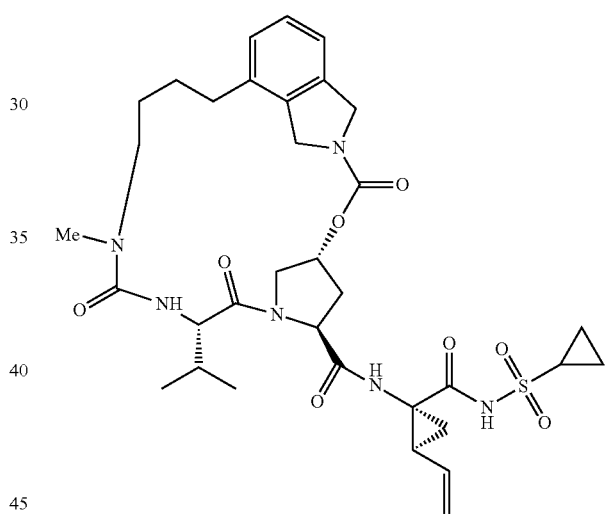
III-127
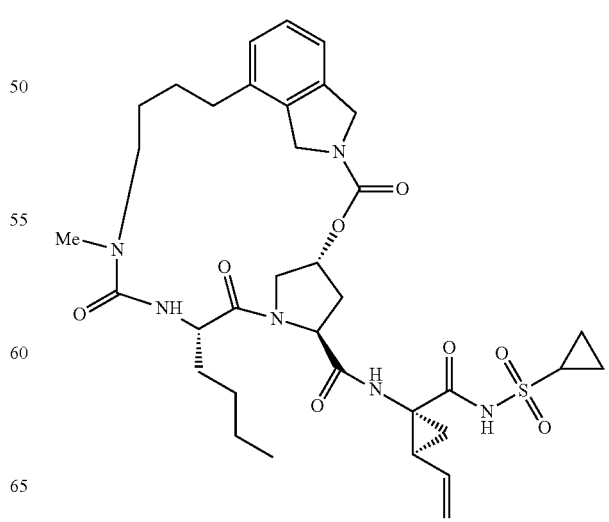

III-128
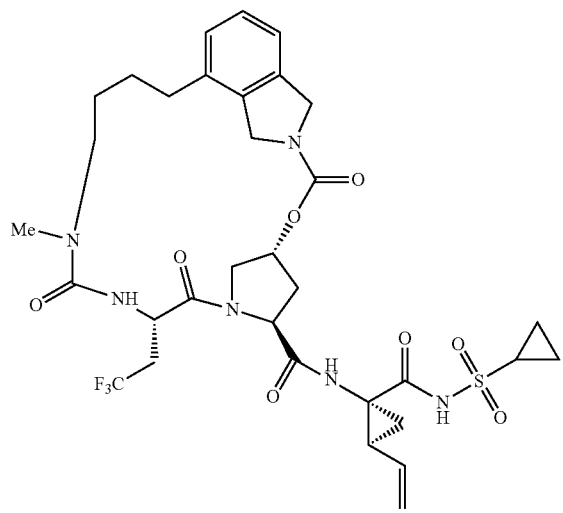
III-129
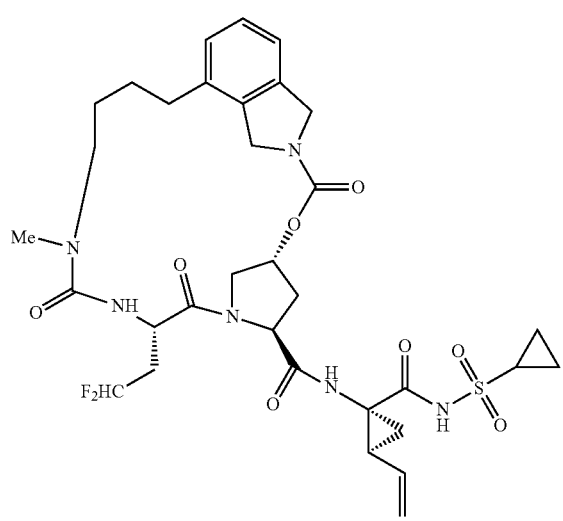
III-130
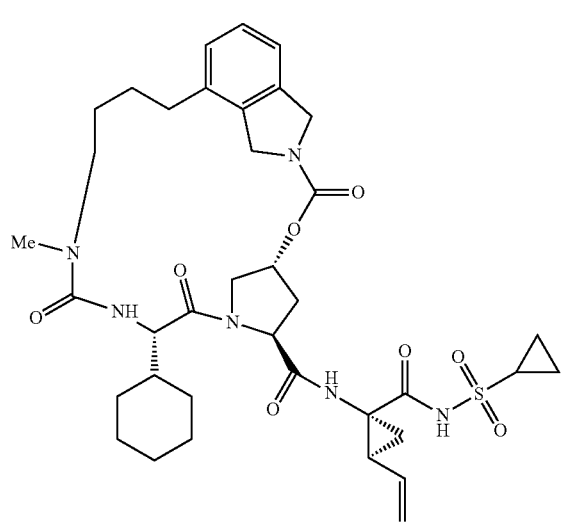
III-131
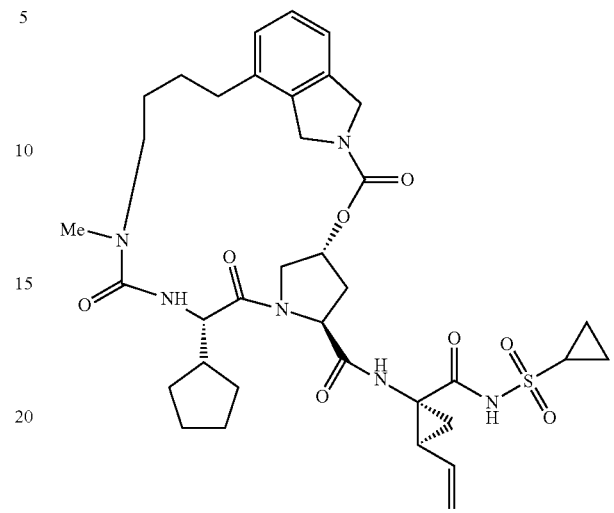
III-152
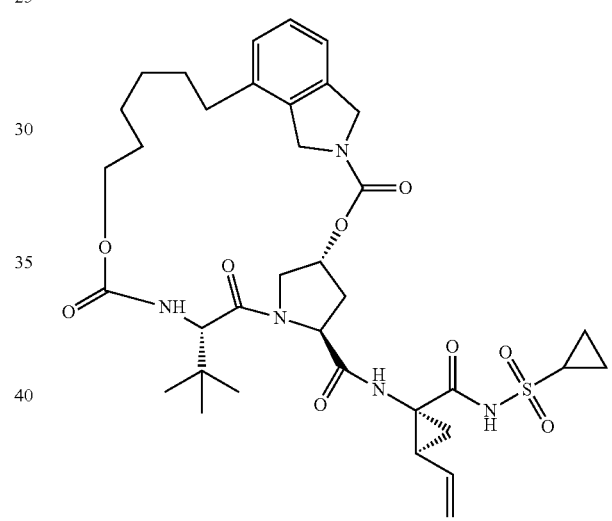
III-153
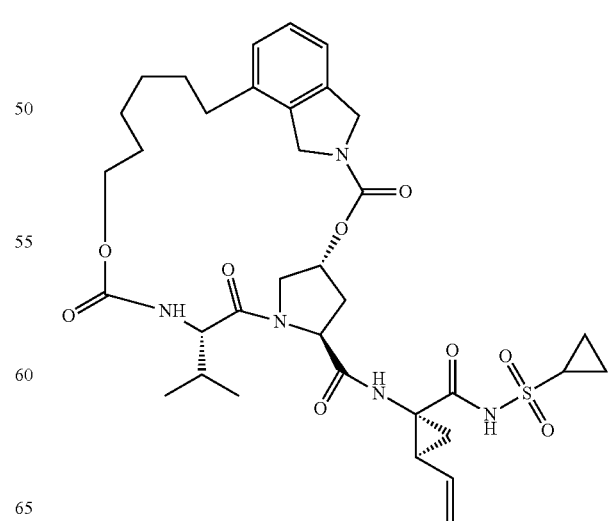

III-154
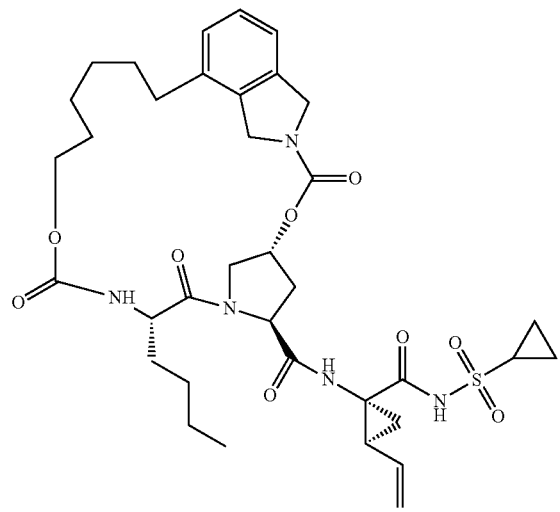
III-155
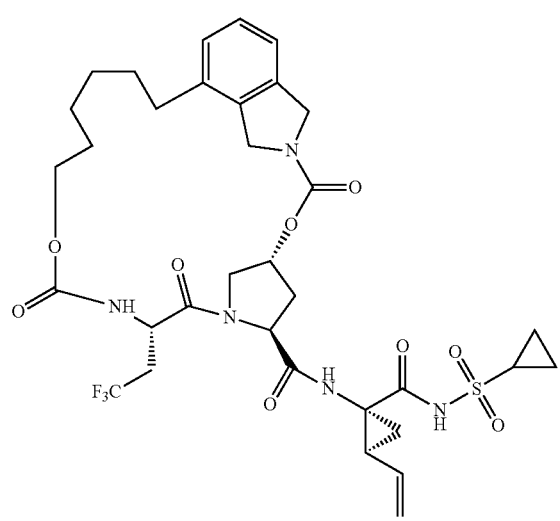
III-156
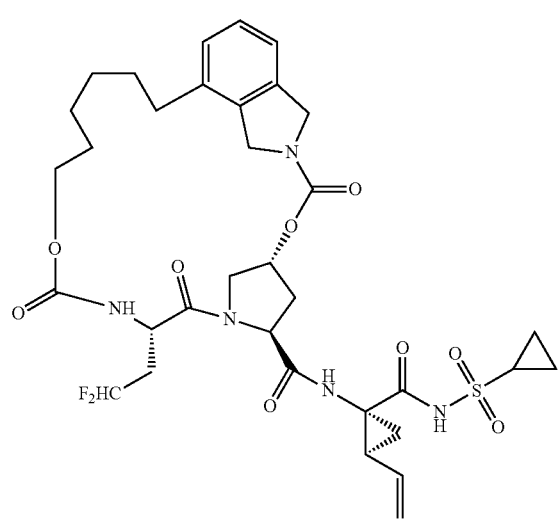
III-157
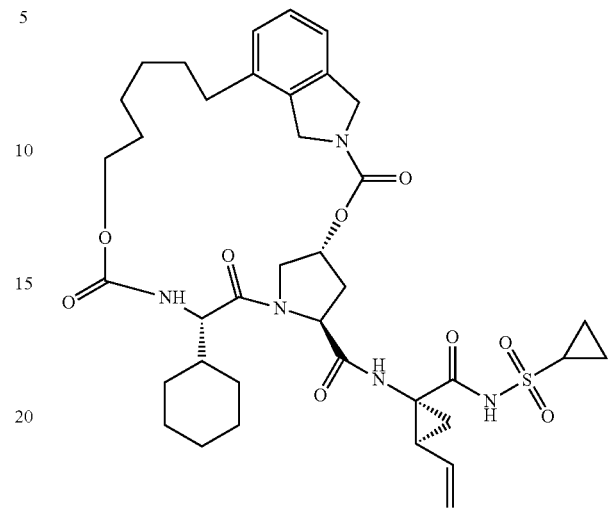
III-158
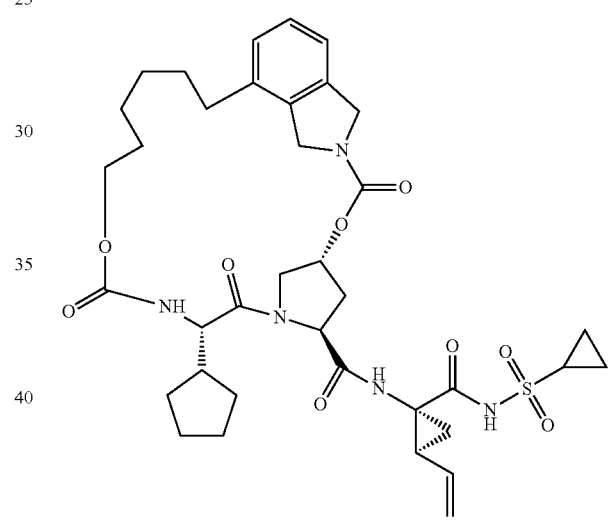
III-159
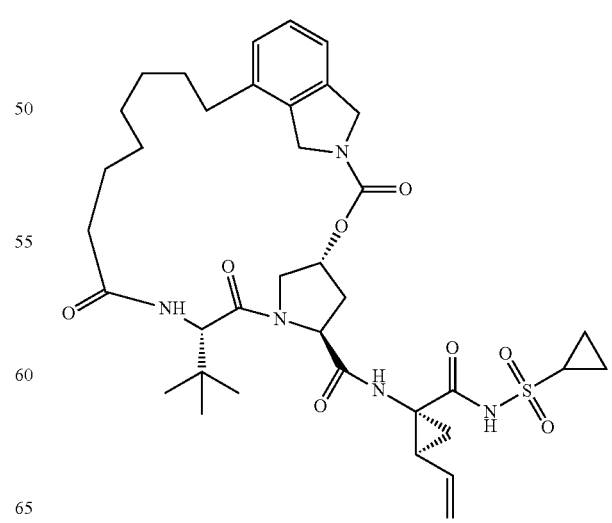

III-160
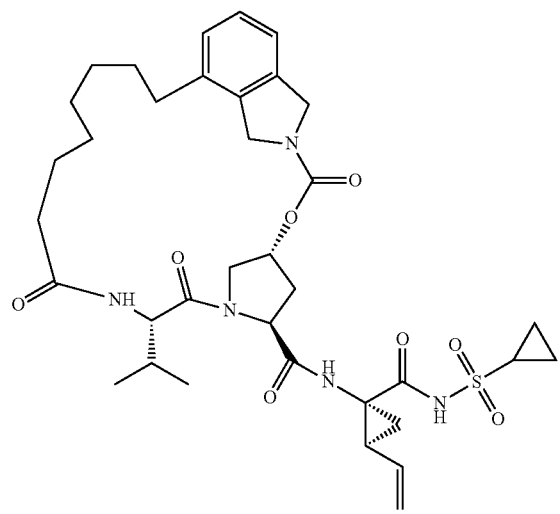
III-161
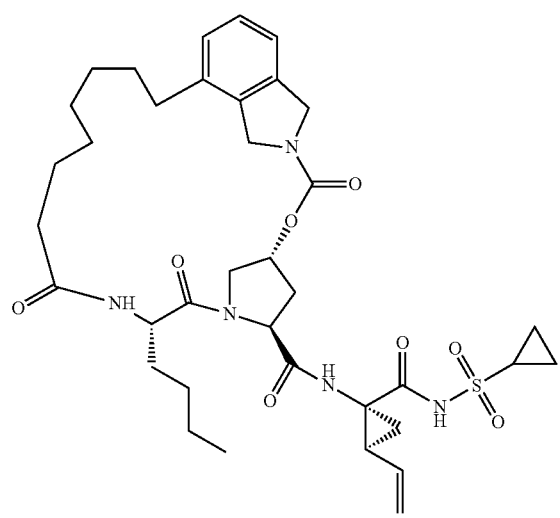
III-162
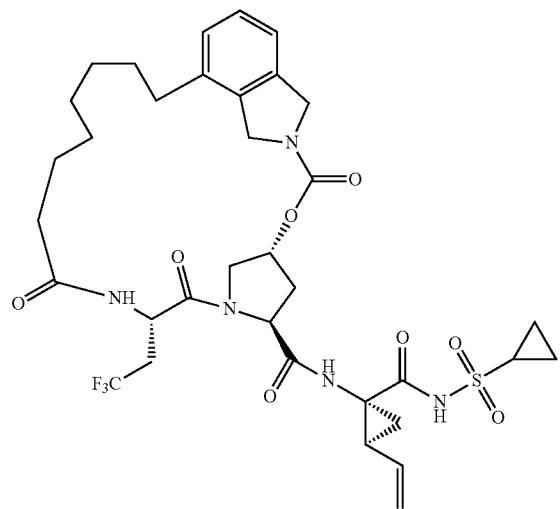
III-163
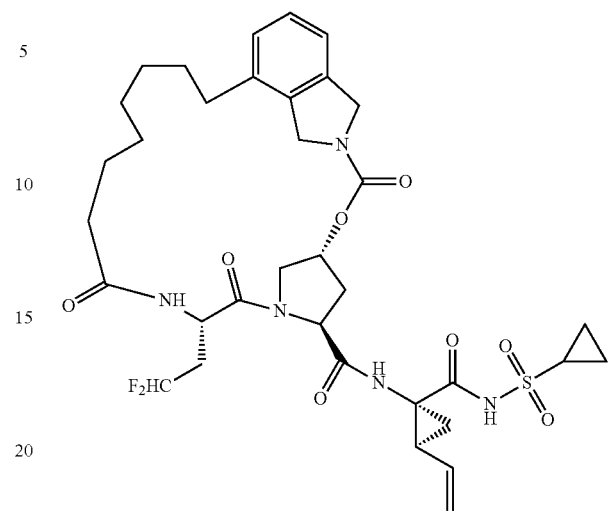
III-164
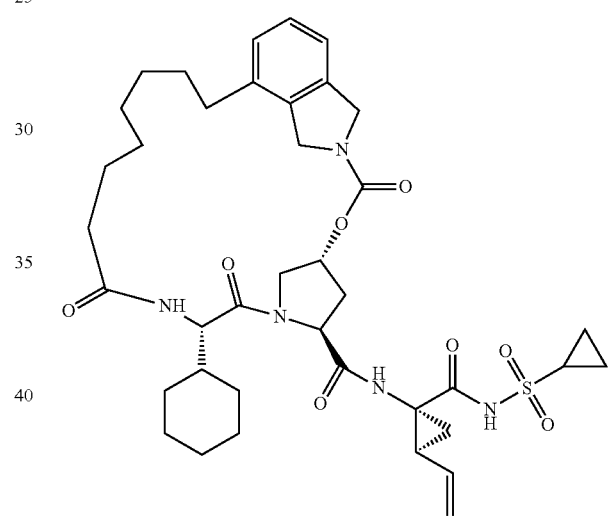
III-165
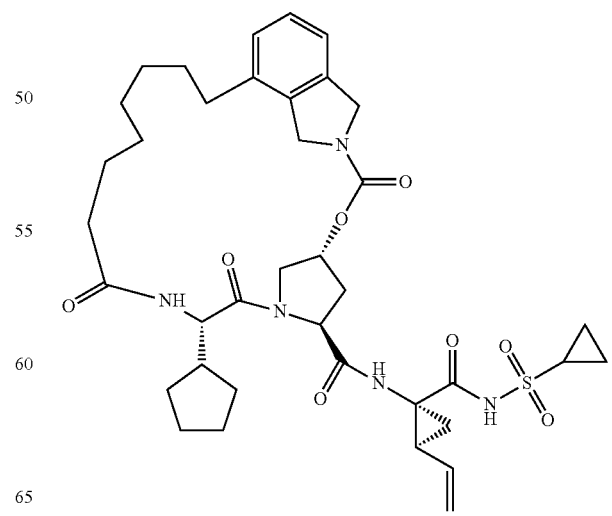

III-166
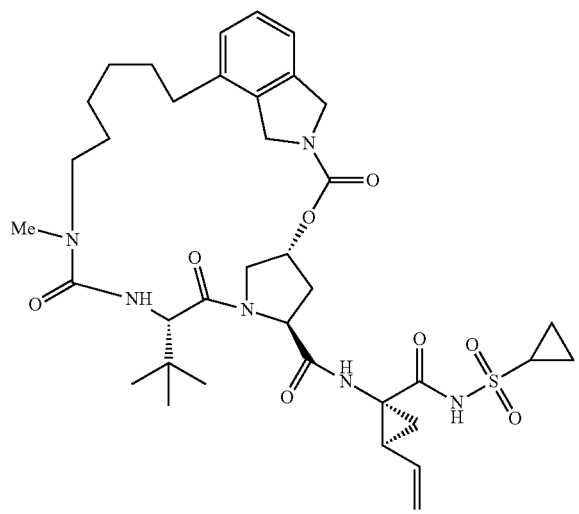
III-169
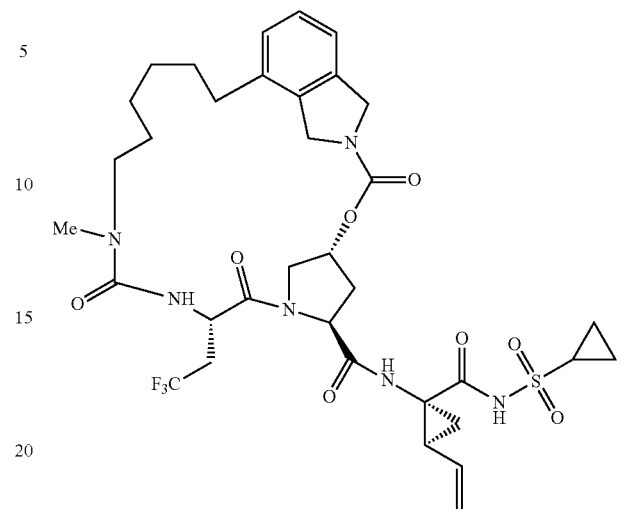
III-167
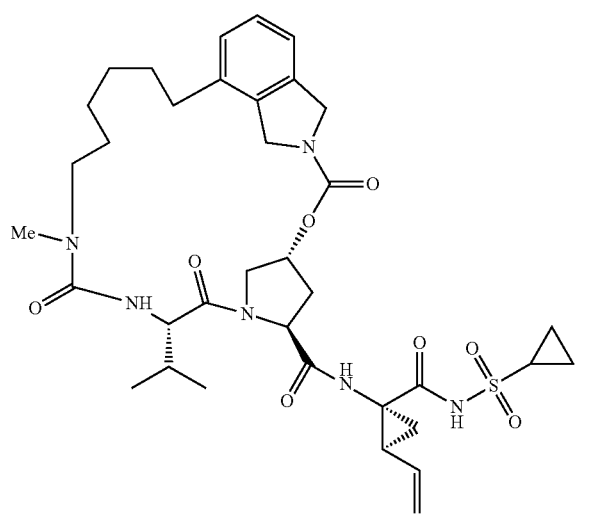
III-170
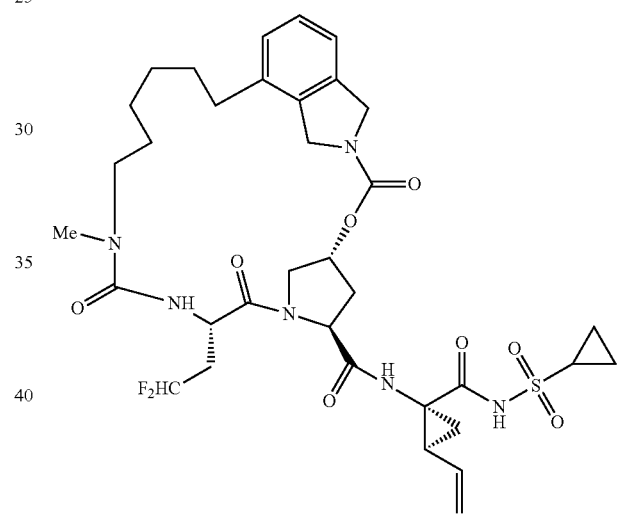
III-168
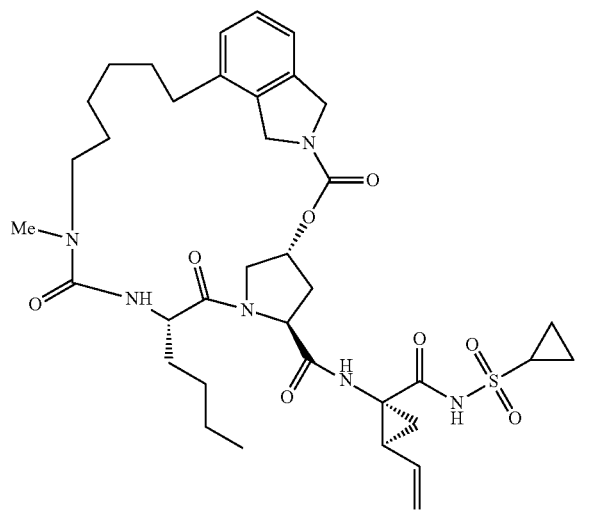
III-171
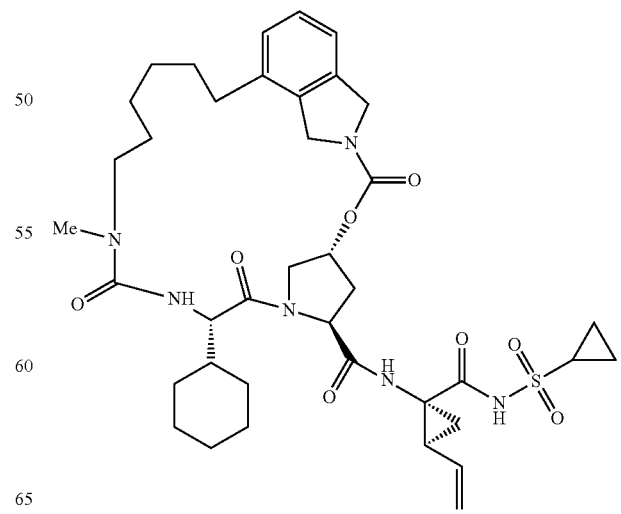

-continued
III-172
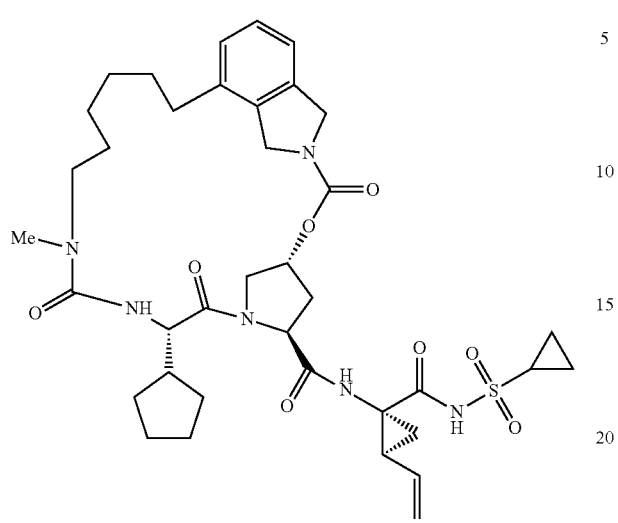
III-200
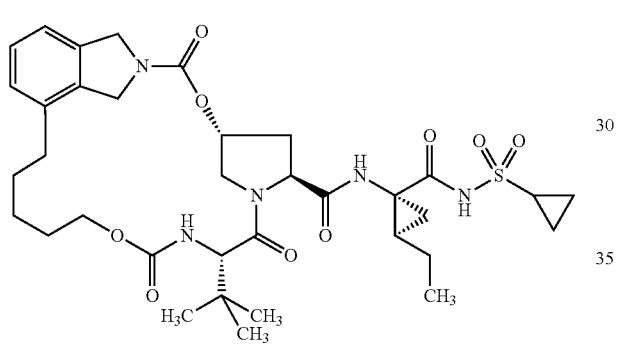
III-201
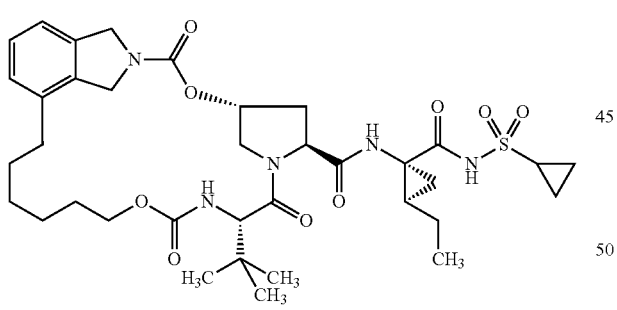
III-202
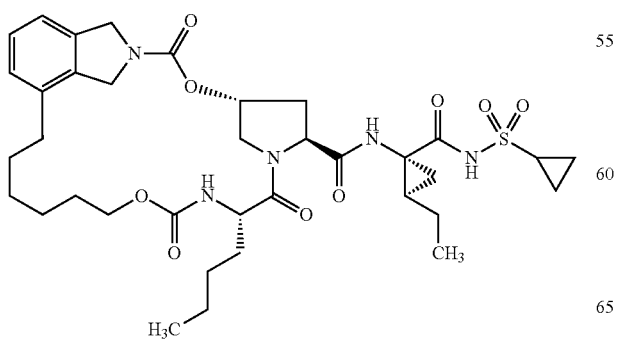
-continued
III-203
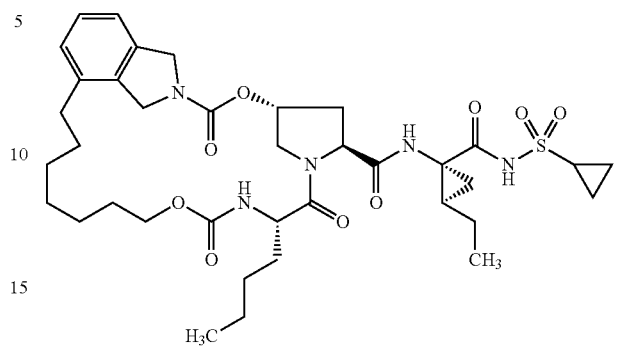
III-204
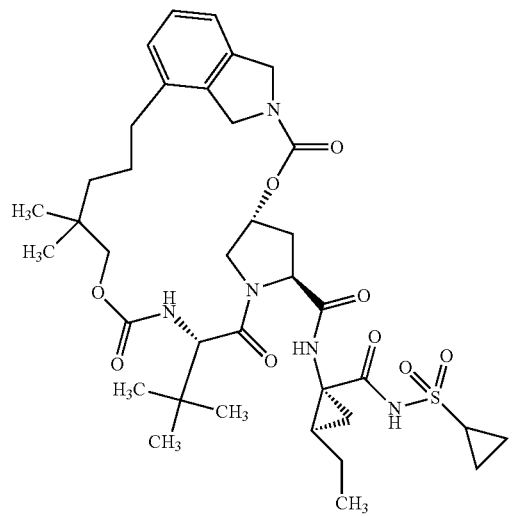
III-205
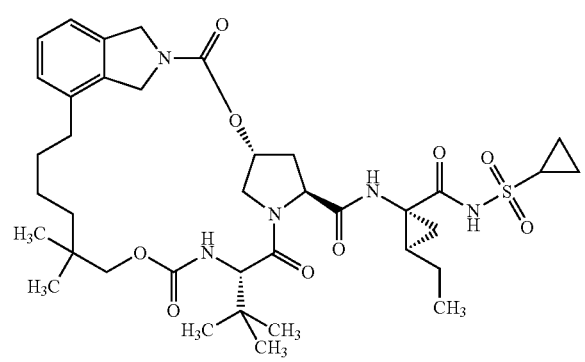

III-206
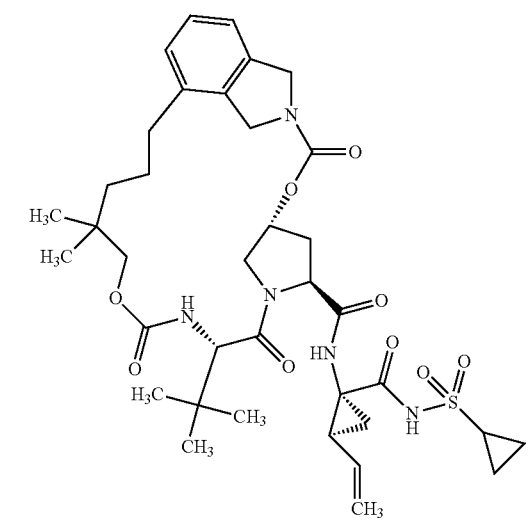
III-210
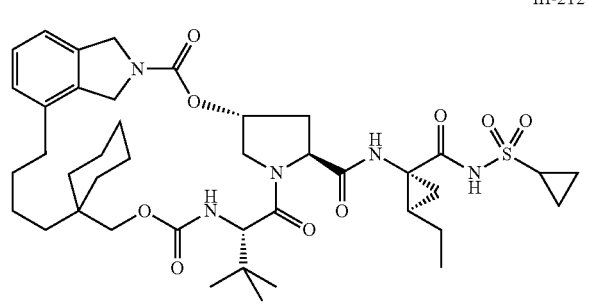
III-212
III-214
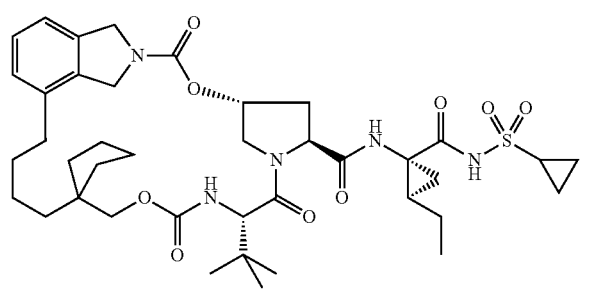
III-216
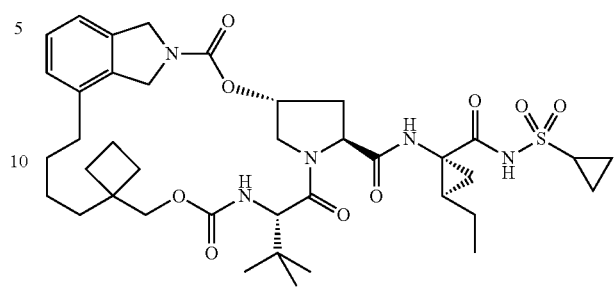
III-218
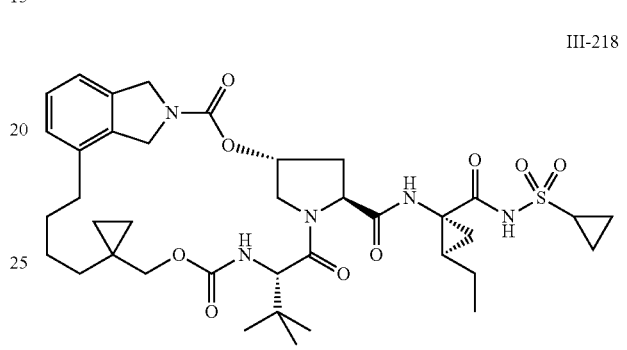
III-220
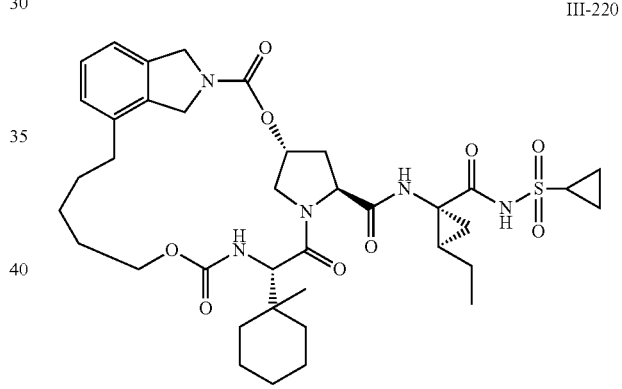
III-222
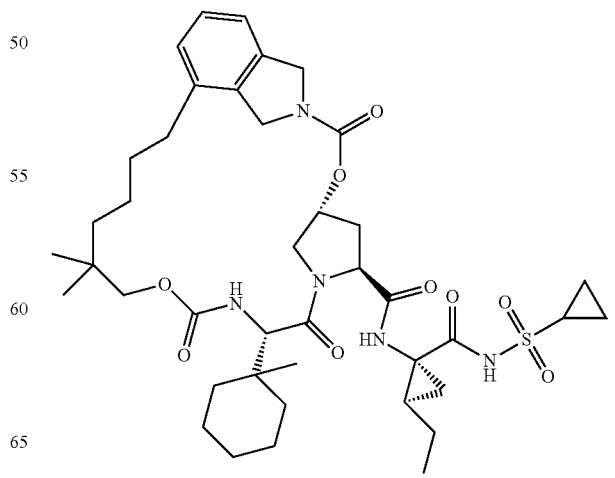

III-224
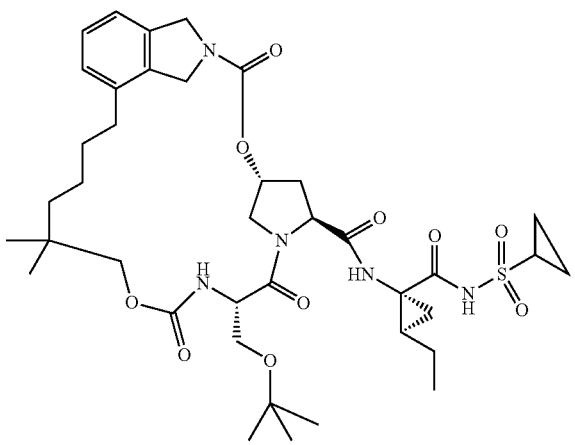
III-226
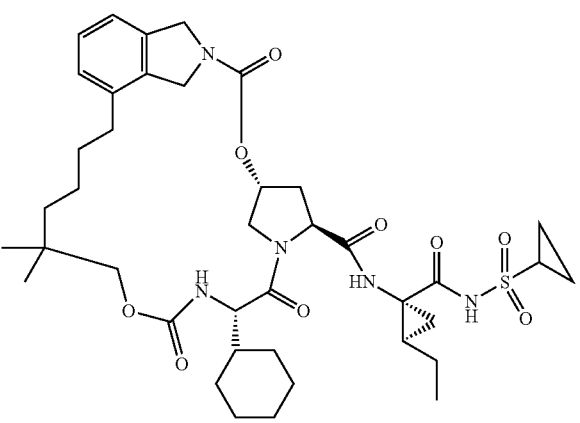
III-229
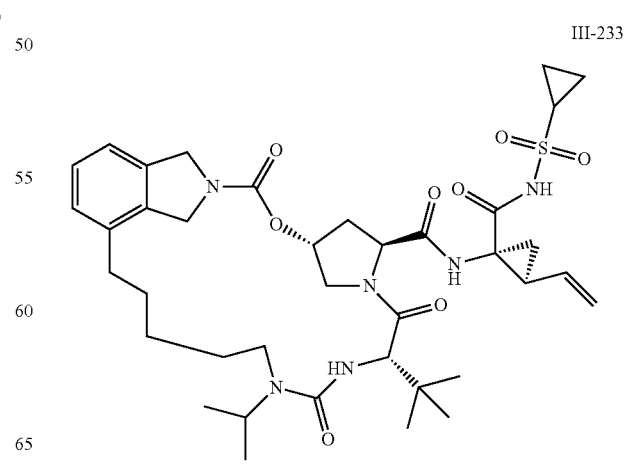
III-230
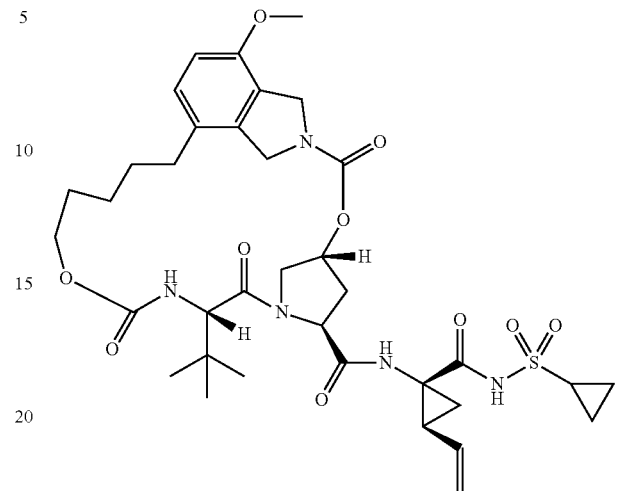
III-231
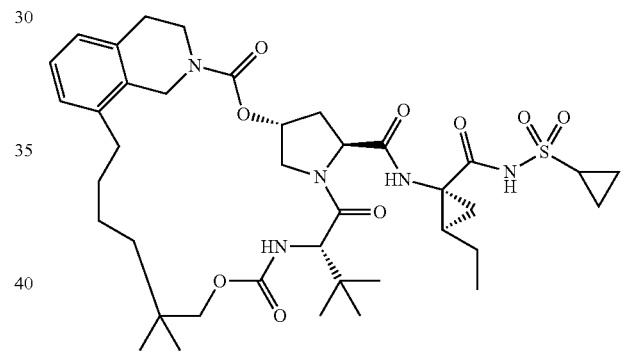
III-233

III-235

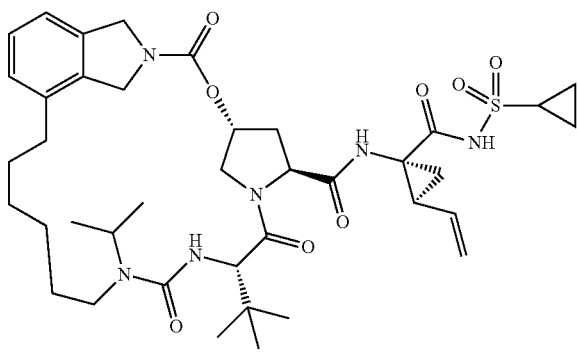

III-237

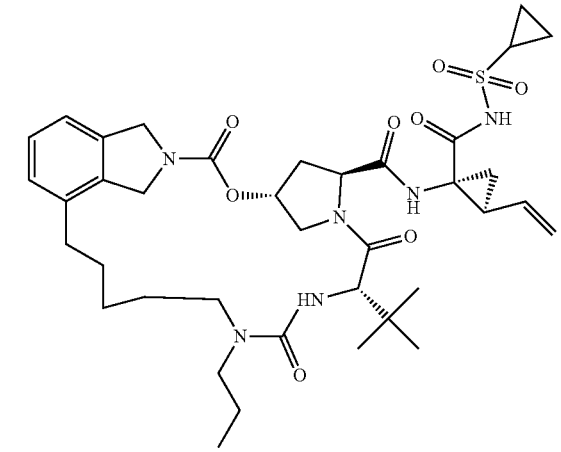

III-238

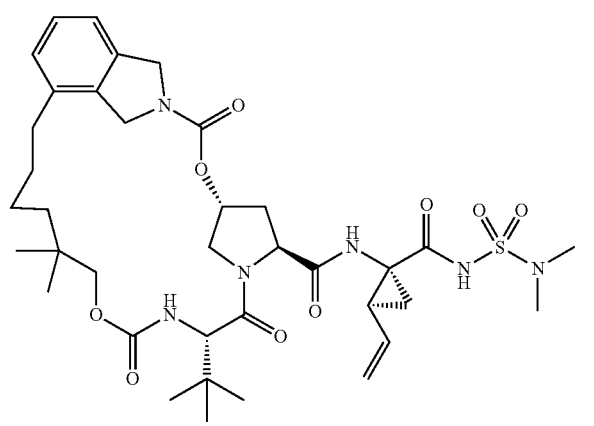

III-239

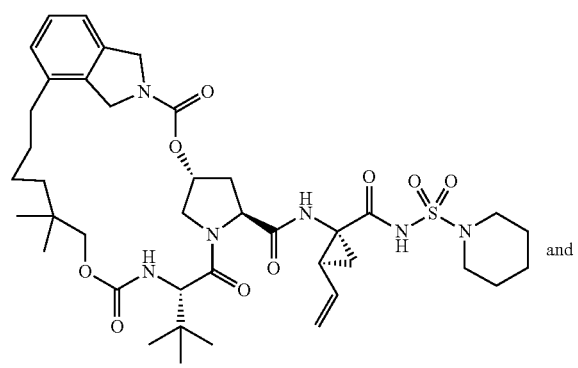

III-240

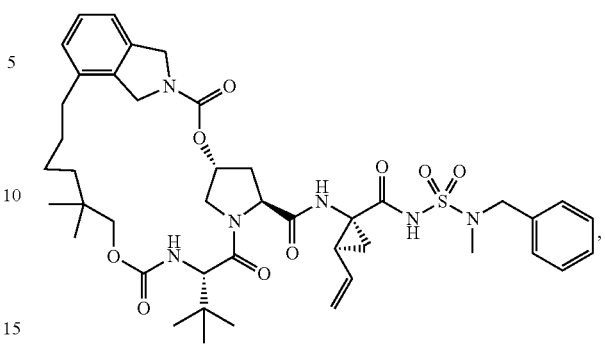

or a pharmaceutically acceptable salt or hydrate thereof. In this eighth embodiment, all other groups are as provided in the general process above and/or in any of the first through seventh embodiments above.

A ninth embodiment of the invention is directed to processes in which the compound of Formula I is a compound of Formula III-205:

III-205

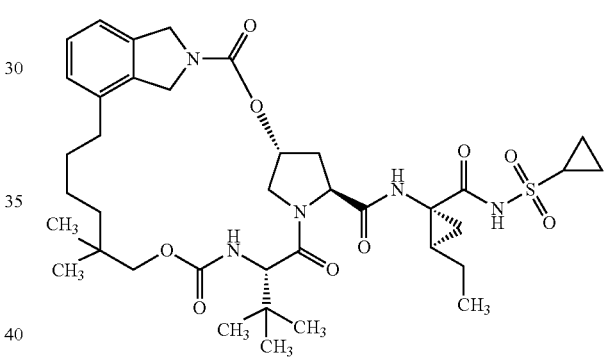

or a pharmaceutically acceptable salt or hydrate thereof. In this ninth embodiment, all other groups are as provided in the general process above and/or in any of the first through seventh embodiments above.

A tenth embodiment of the invention is directed to processes in which the pharmaceutically acceptable salts of the compound of Formula I are selected from the group consisting of aluminum salts, ammonium salts, calcium salts, copper salts, ferric salts, ferrous salts, lithium salts, magnesium salts, manganic salts, manganous salts, potassium salts, sodium salts, zinc salts, salts of primary amines, salts of secondary amines, salts of tertiary amines, salts of substituted amines, salts of cyclic amines, arginine salts, betaine salts, caffeine salts, choline salts, N,N'-dibenzylethylenediamine salts, diethylamine salts, 2-diethylaminoethanol salts, 2-dimethylaminoethanol salts, ethanolamine salts, ethylenediamine salts, N-ethyl-morpholine salts, N-ethylpiperidine salts, glucamine salts, glucosamine salts, histidine salts, hydrabamine salts, isopropylamine salts, lysine salts, methylglucamine salts, morpholine salts, piperazine salts, piperidine salts, polyamine resin salts, procaine salts, purine salts, theobromine salts, triethylamine salts, trimethylamine salts, tripropylamine salts, tromethamine salts, acetic acid salts, benzenesulfonic acid salts, benzoic acid salts, camphorsulfonic acid salts, citric acid salts, ethanesulfonic acid salts, formic acid salts, fumaric acid salts, gluconic acid salts, glutamic acid salts, hydrobromic acid salts, hydrochloric acid salts, isethionic acid salts, lactic acid salts, maleic acid salts, malic acid salts, mandelic acid salts, methanesulfonic acid salts, malonic acid salts, mucic acid salts, nitric acid salts, pamoic acid salts, pantothenic acid salts, phosphoric acid salts, propionic acid salts, succinic acid salts, sulfuric acid salts, tartaric acid salts, p-toluenesulfonic acid salts and trifluoroacetic acid salts. In all aspects of this tenth embodiment, all other groups are as provided in the general process above and/or in any of the first through ninth embodiments above.

In a first aspect of this tenth embodiment of the invention, the pharmaceutically acceptable salt of the compound of Formula I is selected from the group consisting of potassium salts and sodium salts.

In a second aspect of this tenth embodiment of the invention, the pharmaceutically acceptable salt is a sodium or potassium salt of a compound of Formula III-5 through III-7, III-35 through III-52, III-71 through III-91, III-111 through III-131, III-152 through III-172, III-200 through III-206, III-210, III-212, III-214, III-216, III-218, III-220, III-222, III-224, III-226, III-229 through III-231, III-233, III-235, III-237 through III-239 and III-240, as set forth above.

In a third aspect of this tenth embodiment of the invention, the pharmaceutically acceptable salt is a sodium or potassium salt of a compound of Formula III-205, as set forth above.

An eleventh embodiment of the invention is directed to a compound of Formula I or a pharmaceutically acceptable salt thereof, wherein the compound is prepared by the process according to any one of the general process above and/or any one of the first through tenth embodiments. In all aspects of this eleventh embodiment, all groups are as provided in the general process above and/or in any of the first through tenth embodiments above.

A first aspect of the eleventh embodiment is directed to a compound in which p and q are both 1; $R^1$ is $CONR^{10}SO_2R^6$; $R^2$ is $C_1$-$C_6$ alkyl or $C_2$-$C_6$ alkenyl; $R^3$ is $C_5$-$C_6$ cycloalkyl or $C_1$-$C_8$ alkyl substituted with from 0 to 3 halo substitutents; $R^5$ is H, F or Cl; $R^6$ is $C_3$-$C_6$ cycloalkyl; Y is C(=O); Z is O, $CH_2$, NH or $N(CH_3)$; M is $C_1$-$C_8$ alkylene, wherein the M alkylene is substituted with from 0 to 2 substituents selected from the group consisting of $C_1$-$C_8$ alkyl, $C_3$-$C_8$ cycloalkyl($C_1$-$C_8$ alkyl) or aryl($C_1$-$C_8$ alkyl), and 2 adjacent substituents of M, if present, are optionally taken together to form a 3- to 6-membered cyclic ring containing from 0 to 2 heteroatoms selected from N, O, and S; and $R^{10}$ is H or $C_1$-$C_6$ alkyl.

In a second aspect of the eleventh embodiment, the compound of Formula I is selected from the group consisting of Compounds III-5 through III-7, III-35 through III-52, III-71 through III-91, III-111 through III-131, III-152 through III-172, III-200 through III-206, III-210, III-212, III-214, III-216, III-218, III-220, III-222, III-224, III-226, III-229 through III-231, III-233, III-235, III-237 through III-239 and III-240, as set forth above.

A third aspect of the eleventh embodiment is directed to a compound of Formula is a compound of Formula III-205, as set forth above, or a pharmaceutically acceptable salt or hydrate thereof.

In a twelfth embodiment of the invention, a compound of the invention is prepared by process according to any one of the general process above and/or any one of the first through tenth embodiments and is selected from the exemplary species depicted in Examples 1 through 5 shown below.

In a thirteenth embodiment of the invention, a compound of the invention is prepared by process according to any one of the general process above and/or any one of the first through tenth embodiments and is selected from the exemplary stable crystalline forms of the exemplary species depicted in Examples 6 and 7 shown below. The stable crystalline forms are characterized by an X-ray powder diffraction pattern obtained using copper K-ALPHA radiation (i.e., the radiation source is a combination of Cu $K_{\alpha 1}$ and $K_{\alpha 2}$ radiation) which comprises 2Θ values (i.e., reflections at 2Θ values) in degrees as provided. In all aspects of this embodiment and analogous embodiments which follow the term "about" is understood to modify each of the 2Θ values; i.e., the expression "about 17.8, 19.9, 21.0, and 21.8" is short-hand for "about 17.8, about 19.9, about 21.0, and about 21.8". In particular aspects of this embodiment, the compound is selected from the group consisting of:

a stable crystalline ethanol solvate of a potassium salt of Compound III-205 having an x-ray powder diffraction comprising 2Θ values in degrees of about 6.1±0.1, 8.7±0.1 and 12.3±0.1, when copper K-ALPHA radiation is used as the radiation source;

a stable crystalline ethanol solvate of a potassium salt of Compound III-205 having an x-ray powder diffraction comprising 2Θ values in degrees of about 7.4±0.1, 8.2±0.1 and 15.1±0.1, when copper K-ALPHA radiation is used as the radiation source;

a stable crystalline hydrate of a potassium salt of Compound III-205 having an x-ray powder diffraction comprising 2Θ values in degrees of about 6.3±0.1, 8.9±0.1 and 19.6±0.1, when copper K-ALPHA radiation is used as the radiation source;

a stable crystalline hydrate of a potassium salt of Compound III-205 having an x-ray powder diffraction comprising 2Θ values in degrees of about 6.2±0.1, 12.4±0.1 and 14.8±0.1, when copper K-ALPHA radiation is used as the radiation source;

a stable crystalline hydrate of a potassium salt of Compound III-205 having an x-ray powder diffraction comprising 2Θ values in degrees of about 8.7±0.1, 16.2±0.1 and 19.4±0.1, when copper K-ALPHA radiation is used as the radiation source;

a stable crystalline hydrate of a potassium salt of Compound III-205 having an x-ray powder diffraction comprising 2Θ values in degrees of about 8.6±0.1, 16.3±0.1 and 18.9±0.1, when copper K-ALPHA radiation is used as the radiation source;

a stable crystalline hydrate of a potassium salt of Compound III-205 having an x-ray powder diffraction comprising 2Θ values in degrees of about 8.7±0.1, 18.0±0.1 and 18.6±0.1, when copper K-ALPHA radiation is used as the radiation source;

a stable crystalline ethyl acetate solvate of a free acid of Compound III-205 having an x-ray powder diffraction comprising 2Θ values in degrees of about 4.4±0.1, 16.0±0.1 and 17.7±0.1, when copper K-ALPHA radiation is used as the radiation source;

a stable crystalline hydrate of a free acid of Compound III-205 having an x-ray powder diffraction comprising 2Θ values in degrees of about 11.84±0.1, 16.5±0.1 and 18.1±0.1, when copper K-ALPHA radiation is used as the radiation source;

a stable crystalline heptane solvate of a free acid of Compound III-205 having an x-ray powder diffraction comprising 2Θ values in degrees of about 17.0±0.1, 18.3±0.1 and 20.3±0.1, when copper K-ALPHA radiation is used as the radiation source; and a stable crystalline anhydrate of a free acid of Compound III-205 having an x-ray powder diffraction comprising 2Θ values in degrees of about 11.2±0.1, 14.2±0.1 and 20.6±0.1, when copper K-ALPHA radiation is used as the radiation source.

In even more particular aspects of this thirteenth embodiment, the compound is selected from the group consisting of:

a stable crystalline ethanol solvate of a potassium salt of Compound III-205 having an x-ray powder diffraction comprising 2Θ values in degrees of about 6.1±0.1, 7.1±0.1, 8.7±0.1, 10.3±0.1, 12.3±0.1, 13.6±0.1, 16.1±0.1, 20.9±0.1 and 22.1±0.1, when copper K-ALPHA radiation is used as the radiation source;

a stable crystalline ethanol solvate of a potassium salt of Compound III-205 having an x-ray powder diffraction comprising 2Θ values in degrees of about 4.5±0.1, 6.1±0.1, 7.4±0.1, 8.2±0.1, 10.4±0.1, 15.1±0.1, 16.2±0.1, 18.9±0.1 and 20.8±0.1, when copper K-ALPHA radiation is used as the radiation source;

a stable crystalline hydrate of a potassium salt of Compound III-205 having an x-ray powder diffraction comprising 2Θ values in degrees of about 6.3±0.1, 7.3±0.1, 8.9±0.1, 9.7±0.1, 10.6±0.1, 13.9±0.1, 14.6±0.1, 16.0±0.1, 18.0±0.1 and 19.6±0.1, when copper K-ALPHA radiation is used as the radiation source;

a stable crystalline hydrate of a potassium salt of Compound III-205 having an x-ray powder diffraction comprising 2Θ values in degrees of about 6.2±0.1, 7.4±0.1, 12.4±0.1, 14.8±0.1, 17.3±0.1 and 20.4±0.1, when copper K-ALPHA radiation is used as the radiation source;

a stable crystalline hydrate of a potassium salt of Compound III-205 having an x-ray powder diffraction comprising 2Θ values in degrees of about 6.1±0.1, 7.2±0.1, 8.7±0.1, 10.4±0.1, 12.3±0.1, 14.9±0.1, 16.2±0.1, 17.8±0.1, 19.4±0.1 and 24.7±0.1, when copper K-ALPHA radiation is used as the radiation source;

a stable crystalline hydrate of a potassium salt of Compound III-205 having an x-ray powder diffraction comprising 2Θ values in degrees of about 4.7±0.1, 6.3±0.1, 8.1±0.1, 8.6±0.1, 12.4±0.1, 15.2±0.1, 16.3±0.1, 17.2±0.1, 18.9±0.1 and 23.4±0.1, when copper K-ALPHA radiation is used as the radiation source;

a stable crystalline hydrate of a potassium salt of Compound III-205 having an x-ray powder diffraction comprising 2Θ values in degrees of about 8.7±0.1, 9.9±0.1, 11.2±0.1, 12.9±0.1, 13.9±0.1, 14.5±0.1, 18.0±0.1, 18.6±0.1 and 22.4±0.1, when copper K-ALPHA radiation is used as the radiation source;

a stable crystalline ethyl acetate solvate of a free acid of Compound III-205 having an x-ray powder diffraction comprising 2Θ values in degrees of about 4.4±0.1, 11.6±0.1, 11.8±0.1, 13.2±0.1, 13.7±0.1, 14.5±0.1, 16.0±0.1, 16.4±0.1, 17.7±0.1 and 18.4±0.1, when copper K-ALPHA radiation is used as the radiation source;

a stable crystalline hydrate of a free acid of Compound III-205 having an x-ray powder diffraction comprising 2Θ values in degrees of about 9.1±0.1, 11.8±0.1, 12.2±0.1, 14.4±0.1, 16.5±0.1, 18.1±0.1, 18.5±0.1, 18.6±0.1, 22.0±0.1 and 22.7±0.1, when copper K-ALPHA radiation is used as the radiation source;

a stable crystalline heptane solvate of a free acid of Compound III-205 having an x-ray powder diffraction comprising 2Θ values in degrees of about 10.9±0.1, 12.5±0.1, 15.9±0.1, 16.5±0.1, 17.0±0.1, 18.3±0.1, 19.5±0.1, 20.3±0.1, 21.9±0.1 and 22.3±0.1, when copper K-ALPHA radiation is used as the radiation source; and a stable crystalline anhydrate of a free acid of Compound III-205 having an x-ray powder diffraction comprising 2Θ values in degrees of about 2.4±0.1, 3.9±0.1, 11.2±0.1, 14.2±0.1, 16.4±0.1, 17.2±0.1, 19.1±0.1, 20.1±0.1, 20.6±0.1 and 22.1±0.1, when copper K-ALPHA radiation is used as the radiation source.

Other embodiments of the present invention include the following:

(a) A pharmaceutical composition comprising an effective amount of a compound of Formula I and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of HCV protease inhibitors and HCV NS5B polymerase inhibitors.

(d) A pharmaceutical combination, which is (i) a compound of Formula I and (ii) a second therapeutic agent selected from the group consisting of HCV antiviral agents, immunomodulators, and anti-infective agents; wherein the compound of Formula I and the second therapeutic agent are each employed in an amount that renders the combination effective for inhibiting HCV NS3 activity, or for treating HCV infection and/or reducing the likelihood or severity of symptoms of HCV infection, or for inhibiting HCV viral replication and/or HCV viral production in a cell-based system.

(e) The combination of (d), wherein the HCV antiviral agent is an antiviral selected from the group consisting of HCV protease inhibitors and HCV NS5B polymerase inhibitors.

(f) A method of inhibiting HCV NS3 activity in a subject in need thereof, which comprises administering to the subject an effective amount of a compound of Formula I.

(g) A method of treating HCV infection and/or reducing the likelihood or severity of symptoms of HCV infection in a subject in need thereof, which comprises administering to the subject an effective amount of a compound of Formula I.

(h) The method of (g), wherein the compound of Formula I is administered in combination with an effective amount of at least one second therapeutic agent selected from the group consisting of HCV antiviral agents, immunomodulators, and anti-infective agents.

(i) The method of (h), wherein the HCV antiviral agent is an antiviral selected from the group consisting of HCV protease inhibitors and HCV NS3 polymerase inhibitors.

(j) A method of inhibiting HCV viral replication and/or HCV viral production in a cell-based system, which comprises administering to the subject an effective amount of a compound of Formula I.

(k) The method of (j), wherein the compound of Formula I is administered in combination with an effective amount of at least one second therapeutic agent selected from the group consisting of HCV antiviral agents, immunomodulators, and anti-infective agents.

(l) The method of (k), wherein the HCV antiviral agent is an antiviral selected from the group consisting of HCV protease inhibitors and HCV NS5B polymerase inhibitors.

(m) A method of inhibiting HCV NS3 activity in a subject in need thereof, which comprises administering to the subject the pharmaceutical composition of (a), (b), or (c) or the combination of (d) or (e).

(n) A method of treating HCV infection and/or reducing the likelihood or severity of symptoms of HCV infection in a subject in need thereof, which comprises administering to the subject the pharmaceutical composition of (a), (b), or (c) or the combination of (d) or (e).

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (n) above are understood to include all embodiments of the compounds and/or salts, including such embodiments as result from combinations of embodiments.

The present invention also includes a compound of the present invention for use (i) in, (ii) as a medicament for, or (iii) in the preparation of a medicament for: (a) inhibiting HCV NS3 activity, or (b) treating HCV infection and/or reducing the likelihood or severity of symptoms of HCV infection, or (c) use in medicine. In these uses, the compounds of the present invention can optionally be employed in combination with one or more second therapeutic agents selected from HCV antiviral agents, anti-infective agents, and immunomodulators.

Additional embodiments of the invention include the pharmaceutical compositions, combinations and methods set forth in (a)-(n) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

As used herein, the term "alkyl" refers to any linear or branched chain alkyl group having a number of carbon atoms in the specified range. Thus, for example, "$C_{1-6}$ alkyl" (or "$C_1$-$C_6$ alkyl") refers to all of the hexyl alkyl and pentyl alkyl isomers as well as n-, iso-, sec- and t-butyl, n- and isopropyl, ethyl and methyl. Alkyl groups may be substituted as indicated.

The term "halogenated" refers to a group or molecule in which a hydrogen atom has been replaced by a halogen. Similarly, the term "haloalkyl" refers to a halogenated alkyl group. The term "halogen" (or "halo") refers to atoms of fluorine, chlorine, bromine and iodine (alternatively referred to as fluoro, chloro, bromo, and iodo).

The term "alkoxy" refers to an "alkyl-O—" group. Alkoxy groups may be substituted as indicated.

The term "cycloalkyl" refers to any cyclic ring of an alkane or alkene having a number of carbon atoms in the specified range. Thus, for example, "$C_{3-8}$ cycloalkyl" (or "$C_3$-$C_8$ cycloalkyl") refers to cyclopropyl, cyclobutyl, cyclopentyl, cyclohexyl, cycloheptyl, and cyclooctyl. The term "cycloalkoxy" refers to a "cycloalkyl-O—" group. Cycloalkyl groups may be substituted as indicated.

The term "aryl" (or "aryl ring system") refers to aromatic mono- and poly-carbocyclic ring systems wherein the individual carbocyclic rings in the polyring systems are fused or attached to each other via a single bond. As used herein, the term aryl includes aromatic mono- and poly-carbocyclic ring systems that include from 0 to 4 heteroatoms (non-carbon atoms) that are independently chosen from N, O and S. Suitable aryl groups include phenyl, naphthyl, biphenylenyl, pyridinyl, pyrimidinyl and pyrrolyl, as well as those discussed below. Aryl groups may be substituted as indicated. Aryl ring systems may include, where appropriate, an indication of the variable to which a particular ring atom is attached. Unless otherwise indicated, substituents to the aryl ring systems can be attached to any ring atom, provided that such attachment results in formation of a stable ring system.

The term "carbocycle" (and variations thereof such as "carbocyclic") as used herein, unless otherwise indicated, refers to (i) a $C_5$ to $C_7$ monocyclic, saturated or unsaturated ring, or (ii) a $C_8$ to $C_{10}$ bicyclic saturated or unsaturated ring system. Each ring in (ii) is either independent of, or fused to, the other ring, and each ring is saturated or unsaturated. Carbocycle groups may be substituted as indicated. When the carbocycles contain one or more heteroatoms independently chosen from N, O and S, the carbocycles may also be referred to as "heterocycles," as defined below. The carbocycle may be attached to the rest of the molecule at any carbon or nitrogen atom that results in a stable compound. The fused bicyclic carbocycles are a subset of the carbocycles; i.e., the term "fused bicyclic carbocycle" generally refers to a $C_8$ to $C_{10}$ bicyclic ring system in which each ring is saturated or unsaturated and two adjacent carbon atoms are shared by each of the rings in the ring system. A fused bicyclic carbocycle in which both rings are saturated is a saturated bicyclic ring system. Saturated carbocyclic rings are also referred to as cycloalkyl rings, e.g., cyclopropyl, cyclobutyl, etc. A fused bicyclic carbocycle in which one or both rings are unsaturated is an unsaturated bicyclic ring system. Carbocycle ring systems may include, where appropriate, an indication of the variable to which a particular ring atom is attached. Unless otherwise indicated, substituents to the ring systems can be attached to any ring atom, provided that such attachment results in formation of a stable ring system.

Unless indicated otherwise, the term "heterocycle" (and variations thereof such as "heterocyclic" or "heterocyclyl") broadly refers to (i) a stable 5- to 7-membered, saturated or unsaturated monocyclic ring, or (ii) a stable 8- to 10-membered bicyclic ring system, wherein each ring in (ii) is independent of, or fused to, the other ring or rings and each ring is saturated or unsaturated, and the monocyclic ring or bicyclic ring system contains one or more heteroatoms (e.g., from 1 to 6 heteroatoms, or from 1 to 4 heteroatoms) independently selected from N, O and S and a balance of carbon atoms (the monocyclic ring typically contains at least one carbon atom and the bicyclic ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Heterocycle groups may be substituted as indicated, and unless otherwise specified, the substituents may be attached to any atom in the ring, whether a heteroatom or a carbon atom, provided that a stable chemical structure results. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl). Unless expressly stated to the contrary, the term "heteroaryl ring system" refers to aryl ring systems, as defined above, that include from 1 to 4 heteroatoms (non-carbon atoms) that are independently chosen from N, O and S. In the case of substituted heteroaromatic rings containing at least one nitrogen atom (e.g., pyridine), such substitutions can be those resulting in N-oxide formation. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl. Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl and benzo-1,3-dioxolyl.

Unless otherwise specifically noted as only "substituted", alkyl, cycloalkyl, and aryl groups are not substituted. Preferably, the substituents are selected from the group which includes, but is not limited to, halo, $C_1$-$C_{20}$ alkyl, —$CF_3$, —$NH_2$, —$N(C_1$-$C_6$ alkyl$)_2$, —$NO_2$, oxo, —CN, —$N_3$, —OH, —$O(C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) S(O)$_{0-2}$—, aryl-S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2$N—C(NH)—, —$O(C_1$-$C_6$ alkyl)$CF_3$, ($C_0$-$C_6$ alkyl)C(O)—, ($C_0$-$C_6$ alkyl)OC(O)—, ($C_0$-$C_6$alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, aryl, aralkyl, heteroaryl, heterocyclylalkyl, halo-aryl, halo-aralkyl, halo-heterocycle and halo-heterocyclylalkyl.

Unless expressly stated to the contrary, all ranges cited herein are inclusive. For example, a heteroaryl ring described as containing from "0 to 3 heteroatoms" means the ring can contain 0, 1, 2, or 3 heteroatoms. It is also to be understood that any range cited herein includes within its scope all of the sub-ranges within that range. The oxidized forms of the heteroatoms N and S are also included within the scope of the present invention. In addition, the term "or," as used herein, denotes alternatives that may, where appropriate, be combined; that is, the term "or" includes each listed alternative separately as well as their combination.

When any variable (for example, $R^5$ or $R^6$) occurs more than one time in any constituent or in Formula I or in any other formula depicting and describing compounds of the invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom provided such substitution is chemically allowed and results in a stable compound. A "stable" compound is a compound that can be prepared and isolated and whose structure and properties remain or can be caused to remain essentially unchanged for a period of time sufficient to allow use of the compound for the purposes described herein (e.g., therapeutic or prophylactic administration to a subject).

As a result of the selection of substituents and substituent patterns, certain of the compounds of the present invention can have asymmetric centers and can occur as mixtures of stereoisomers, or as individual diastereomers, or enantiomers. All isomeric forms of these compounds, whether isolated or in mixtures, are within the scope of the present invention.

The compounds prepared via the present invention may be chiral as a result of asymmetric centers, chiral axes, or chiral planes as described in: E. L. Eliel and S. H. Wilen, *Stereochemistry of Carbon Compounds*, John Wiley & Sons, New York, 1994, pages 1119-1190), and may occur as single optical isomers or as mixtures of any number of the possible optical isomers, including racemates, racemic mixtures, diastereomers, diastereomeric mixtures, enantiomers, and enantiomeric mixtures. In certain instances, the compounds disclosed may exist as tautomers and all tautomeric forms are intended to be encompassed by the scope of the invention, even though only one tautomeric structure is depicted. That is, for the purposes of the present invention, a reference to a compound of Formula I is a reference to the compound per se, or to any one of its tautomers per se, or to mixtures of two or more tautomers.

It is generally preferable to administer compounds of the present invention in their enantiomerically pure form. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

The compounds of the present invention may be administered in the form of pharmaceutically acceptable salts. The term "pharmaceutically acceptable salt" refers to a salt that possesses the effectiveness of the parent compound and that is not biologically or otherwise undesirable (e.g., is neither toxic nor otherwise deleterious to the recipient thereof). Suitable salts include acid addition salts that may, for example, be formed by mixing a solution of the compound of the present invention with a solution of a pharmaceutically acceptable acid such as hydrochloric acid, sulfuric acid, acetic acid, trifluoroacetic acid, or benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administering" a compound) in reference to a compound of the invention mean providing the compound or a prodrug of the compound to the individual in need of treatment. When a compound of the invention or a prodrug thereof is provided in combination with one or more other active agents (e.g., antiviral agents useful for treating HCV infection), "administration" and its variants are each understood to include concurrent and sequential provision of the compound or salt (or hydrate) and other agents.

As used herein, the term "composition" is intended to encompass a product comprising the specified ingredients, as well as any product that results, directly or indirectly, from combining the specified ingredients.

By "pharmaceutically acceptable" is meant that the ingredients of the pharmaceutical composition must be compatible with each other and not deleterious to the recipient thereof.

The terms "subject" (alternatively referred to herein as "patient") and "cell-based system", as used herein, refer to an animal, preferably a mammal, most preferably a human, who has been the object of treatment, observation or experiment, The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Particularly preferred are citric, fumaric, hydrobromic, hydrochloric, maleic, phosphoric, sulfuric, and tartaric acids.

The compounds afforded by the instant invention are useful intermediates in the production of HCV NS3 inhibitor compounds or are themselves HCV NS3 inhibitor compounds useful for treating conditions caused by HCV infection or which can be ameliorated by inhibition of HCV infection, and/or reduction of the likelihood or severity of symptoms of HCV infection, alone or in combination with other active agents. For example, the compounds of this invention are useful in treating infection by HCV after suspected past exposure to HCV by such means as blood transfusion, exchange of body fluids, bites, accidental needle stick, or exposure to patient blood during surgery. Treatment is effected by administration of the final product obtained from the disclosed processes to a mammal in need of such treatment. In addition, these compounds are useful as ingredients in pharmaceutical compositions alone or in combination with other active agents.

The following schemes and examples are illustrative of the processes encompassed by the present invention. As will be readily apparent to those in the field, the substituents and substitution patterns on the substrates exemplified herein may be modified without undue experimentation by the choice of readily available starting materials, reagents, and conventional procedures or variations. As used below and throughout this disclosure, "room temperature" or "RT" indicates that the reaction was performed at ambient temperature without the use of any means for cooling or heating. "Room temperature" is about 25° C.

The illustrative examples below, therefore, are not limited by the compounds listed or by any particular substituents employed for illustrative purposes. Substituent numbering as shown in the schemes does not necessarily correlate to that used in the claims and often, for clarity, a single substituent is shown attached to the compound in place of multiple substituents allowed under the definitions of Formula I defined above.

The processes of the instant invention are useful in the preparation of compounds of Formula I. The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above. The following reaction schemes and examples serve only to illustrate the invention and its practice.

Abbreviations
% ee or % EE Percent enantiomeric excess
A % Area percent
ACE-Cl 1-Chloroethyl chloroformate
AY Assay yield
BBI Bromobenzyl isoindoline
BHT Butylated hydroxytoluene (2,6-di-t-butyl-4-methylphenol)
$BnNH_2$ Benzylamine
Boc, boc or BOC t-Butyloxycarbonyl
$Bz_2O_2$ Benzoyl peroxide
Cbz or CBZ Carbobenzyloxy
CDI N,N'-Carbonyl diimidazole
$CH_2O$ Formaldehyde
$Cs_2CO_3$ Cesium carbonate
DBU 1,8-Diazabicyclo[5.4.0]undec-7-ene
DCHA Dicyclohexylamine
DiBAl—H Diisobutylaluminum hydride
DIPEA Diisopropylethylamine
DMAP 4-Dimethylamino pyridine
DMF Dimethylformamide
DMPU N,N'-dimethyl-N,N'-trimethylene urea
DMSO Dimethyl sulfoxide
EDC N-(3-Dimethylaminopropyl)-N'-ethylcarbodiimide
GC Gas chromatography
$H_2$ Hydrogen or hydrogen atmosphere
$H_3PO_4$ Phosphoric acid
HATU O-(7-Azabenzotriazol-1-yl)-N,N,N',N'-tetramethyluronium hexafluorophosphate
HBr Hydrobromic acid
HCl Hydrochloric acid
Hg Mercury
HOBt 1-Hydroxy benzotriazole
HOPO 2-Hydroxypyridine N-oxide
HPLC High performance liquid chromatography
iPAc Isopropyl acetate
$K_2HPO_4$ Potassium phosphate dibasic
KF Karl-Fisher Water Titration
KOH Potassium hydroxide
KOt-Bu Potassium tert-butoxide, also potassium t-butoxide
LiOH Lithium hydroxide
Me Methyl
MeCN or $CH_3CN$ Acetonitrile
MeCy Methylcyclohexane
MeOH or $CH_3OH$ Methanol
$MeSO_3H$ or MsOH Methane sulfonic acid
$MgSO_4$ Magnesium sulfate
ML loss Mother liquor loss
MTBE Methyl t-butyl ether
$N_2$ Nitrogen or nitrogen atmosphere
$Na_2CO_3$ Sodium carbonate
$NaHCO_3$ Sodium hydrogen carbonate (sodium bicarbonate)
NaOH Sodium hydroxide
NaOMe Sodium methoxide
NBS N-bromosuccinimide
NMP N-Methyl pyrrolidinone
NMR Nuclear magnetic resonance spectroscopy
$Pd(tBu_3P)_2$ Palladium bis-(tri-t-butylphosphine)
Pd/C Palladium on carbon
$PdCl_2(CH_3CN)_2$ Palladium dichloride acetonitrile complex
$Pd(OAc)_2$ Palladium acetate
PhCHO Benzaldehyde
PhCl Chlorobenzene
PhMe Toluene RH Relative humidity
RT Room temperature, approximately 25° C.
Ru/C Ruthenium on carbon
tBu$_3$P Tri-t-butyl phosphine
TEA or NEt$_3$ Triethylamine
TFA Trifluoroacetic acid
TG Thermogravitric analysis
THF Tetrahydrofuran
TsOH or PTSA p-Toluene sulfonic acid
X-Phos    2-Dicyclohexylphosphino-2',4',6'-triisopropyl biphenyl
XRPD X-ray powder diffraction Intermediates Intermediates A
Intermediate A1

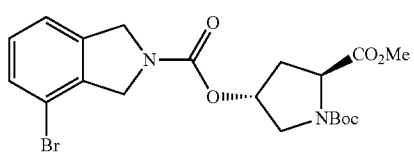 [SMILES: COC(=O)[C@@H]1C[C@@H](OC(=O)N2Cc3cccc(Br)c3C2)CN1C(=O)OC(C)(C)C]

Step 1

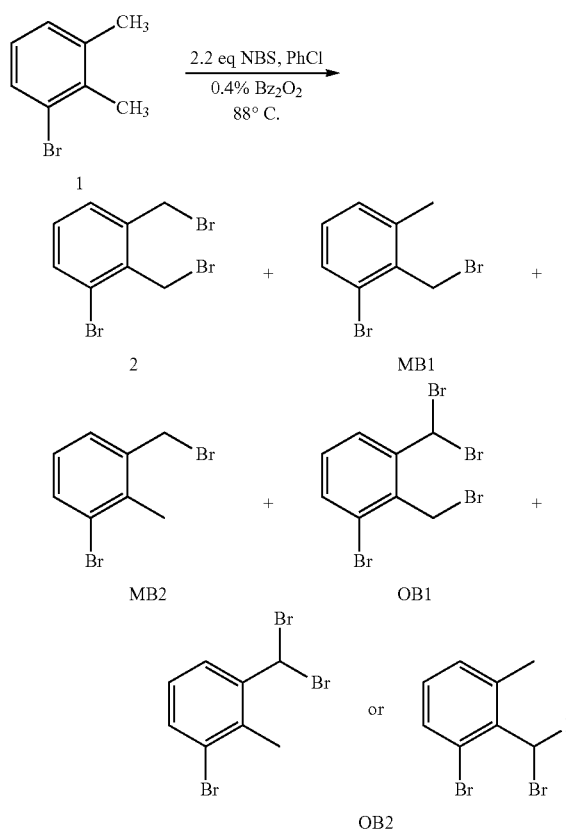

To a 100-L round-bottom glass vessel with steam-heating pot under N$_2$ was added 3-bromo-o-xylene (99%, 7 kg, 37.8 mol), PhCl (70 L), NBS (11.9 kg) and Bz$_2$O$_2$ (18.2 g). The reaction mixture was heated to 88° C. The batch was stirred at the same temperature for 15 hours. The second portion of NBS (2.2 kg) and Bz$_2$O$_2$ (9.1 g) were added, the batch was stirred at 88° C. for 2-3 hours. After the last portion of NBS (0.7 kg) and Bz$_2$O$_2$ (9.1 g) were added, the batch was stirred at 88° C. for 1.5-2 hours.

The reaction was monitored by HPLC assay, and typically the conversion at this stage reached 95%. The batch was cooled to 30° C. and transferred to 200 L extractor. Water (30 L) was added, the mixture was stirred vigorously for 10 minutes. After the layers were separated, the bottom organic layer was washed with water (2×30 L), and the solution of α,α'-dibromo-o-xylene 2 was ready (75% yield, 28.35 moles, 120 mg/mL, 81 L total) for the next step reaction without further purification.

Step 2

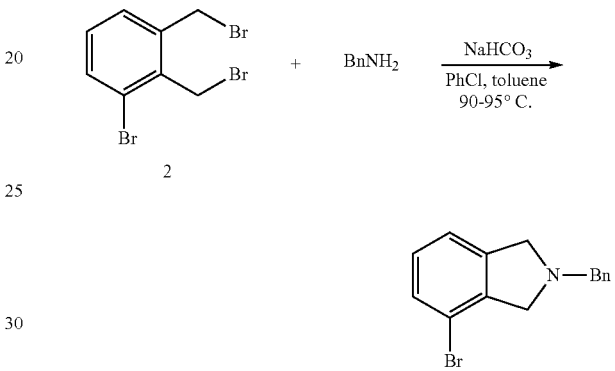

To a 100 L round-bottom glass vessel with steam-heating pot under N$_2$ was added α,α'-dibromo-o-xylene 2 in PhCl (27 L, 120 g/L, 3.24 kg assay), PhMe (41 L) and NaHCO$_3$ (1.75 kg). The reaction mixture was degassed by bubbling N$_2$ at RT for 5 minutes. BnNH$_2$ (1.03 L) was added last at RT. The batch was then heated to 95° C., and the temperature was maintained at 90-95° C. for 8 hours. Second portion of BnNH$_2$ (0.11 L) was then added, and reaction mixture was stirred at 90-95° C. for 3-5 hours. After the last portion of BnNH$_2$ (0.1 L) was added, the batch was stirred for another 3-5 hours at 90-95° C. The reaction was monitored by HPLC assay, and typically the conversion reached 95-97% by mole (the response factor of N-benzylated product 3 and dibromoxylene 2 is 1:1.1 by mole).

The batch was cooled to 25° C. and quenched with water (25 L), transferred to an extractor, and the layers separated. The upper organic layer was ready for the next step salt formation without further purification. The typical assay yield of BBI 3 in PhMe-PhCl solution (70 L) at this stage was 70-73%.

Step 3

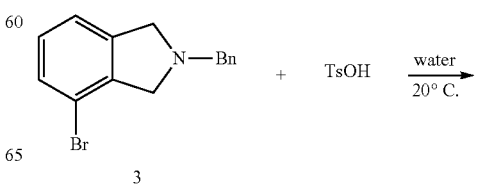

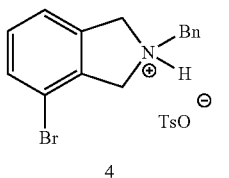

4

To a 200 L extractor, BBI (6.6 moles) in PhMe-PhCl solution (70 L) and 1M H₃PO₄ (40 L) were added. The mixture was stirred vigorously for 10 minutes. The layers were cut; the organic layer was extracted with 1M H₃PO₄ (40 L). Both extracted organic and aqueous layers were analyzed by HPLC assay, more 1M H₃PO₄ extraction might be needed if necessary to transfer all products from organic to aqueous layer.

The combined aqueous layer treated with TsOH monohydrate (2.26 kg) by portion-wise addition. The solid salt formed gradually; the slurry was stirred at 20-25° C. for 2-3 hours, filtered, and the wet cake was rinsed with water (2×12 L). The cake was dried under reduced pressure with N₂ sweep to give product 4 as white solid (2.7 kg, 99% wt) with 90% isolated yield.

Step 4

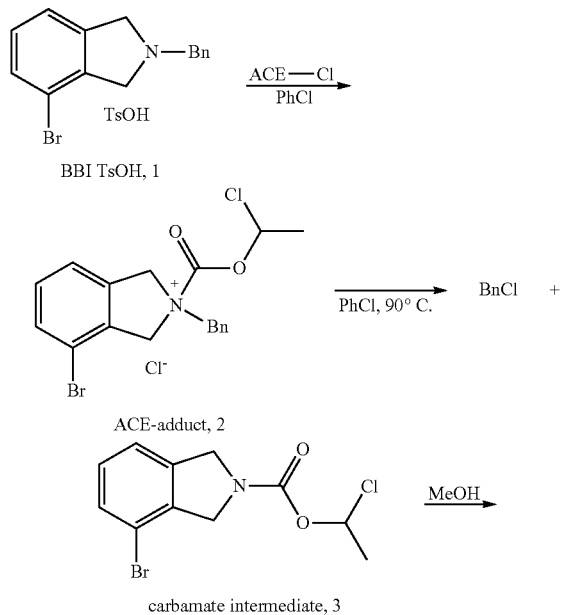

To a 50 L extractor was charged iPAc (39 L), 5 N NaOH (8.0 L, 2.19 eq), and water (32.0 L). With stirring, BBI-TsOH salt (8.424 kg, 1.0 eq) was added at RT. The BBI-TsOH salt is white, but is dark orange in solution and usually breaks up fairly quickly. After one hour, the pH of the aqueous layer was determined to be about 7. Additional 10N NaOH (2.5 L) was added, and the solid completely dissolved within 5 minutes. The final pH of the aqueous layer was 12. The layers were cut, and the organic layer washed with water (40.0 L). The pH of the water wash was 7. HPLC of washes showed <0.05% BBI in basic layer and <0.05% BBI in water wash.

20 L of the BBI solution was fed into a 50 L, 4-neck round-bottom flask, equipped with N₂ line, thermocouple, and batch concentrator. The solution was distilled at 30-33° C., 27-28 inches Hg, maintaining constant volume by feeding in the remaining BBI solution. The mixture was then flushed with iPAc (30 L) and allowed to concentrate down to 10 L. The iPAc distillation is used to azeotropically remove water. The final KF was 129.2 µg/mL. The mixture was solvent switched to chlorobenzene by continued distillation using 20 L of PhCl (sieve dried, KF 40 µg/mL). ¹H NMR of the batch showed no iPAc remained. The final KF of the batch was 83 µg/mL. Pellet molecular sieves (4A, 8-12 mesh) were added to the solution, and the mixture was allowed to stir for 30 minutes. The reaction was inerted with N₂ and ACE-Cl (2.6 L, 1.3 eq) added dropwise over 40 minutes. The reaction was heated to 90° C. and held for 3.5 hours. Reaction is exothermic (~15° C. increase). The reaction was aged at RT for 20 minutes until the exotherm had slowed before heating. The initial orange solution becomes a thick yellow slurry on formation of the ACE-adduct 2, which gradually dissolves in a dark greenish-brown solution as the carbamate intermediate 3 is formed. The reaction conversion is monitored by conversion of the ACE-adduct 2 to the carbamate intermediate 3.

The reaction was cooled to ambient. The batch was filtered through Solka Flok to remove the molecular sieves and transferred into a clean 50-L round-bottom flask. MeOH (8.8 L, 11.9 eq) was used to rinse the flask and filter cake, and the filtrate was added to the reaction flask. A slight exotherm was observed (5° C. increase). The reaction was aged for 15 minutes until the exotherm slowed. A reflux condenser was attached, and the batch was heated under nitrogen to 65° C. for 2 hours. The reaction did not go to completion, so additional MeOH (4 L, 5.4 eq) was added, and the mixture was refluxed for an additional 30 minutes. During the reaction, the solution turned dark purple, and large white crystals began to form; crystallization began shortly after reaching reflux. The reaction conversion was measured by the ratio of carbamate intermediate 3 to benzyl chloride and should be >99.5%. The reaction is normally complete in 2 hours. The solid was isolated by filtration, using mother liquors to complete the transfer. The cake was washed with 3:1 MeCN/MeOH (2×4.5 L) and dried on the filter under N₂ tent for 2 days. The product was obtained as a light pink, crystalline solid (3.76 kg, 96.6 wt %, >99.5 A %) in 87.7% yield, uncorrected. HPLC assay of the mother liquors and MeCN/MeOH washes showed 0.11 g/L loss (0.08%) and 0.0264 g/L loss (<0.05%), respectively.

Step 5

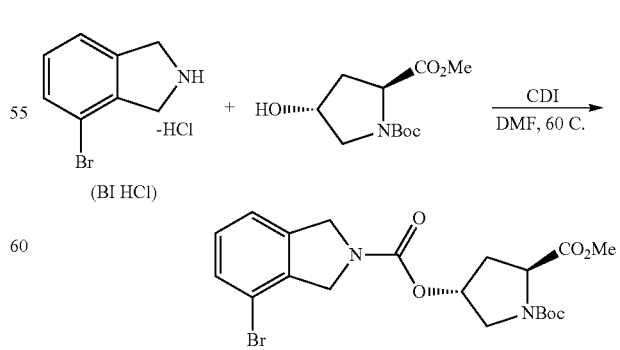

To a 50-L, 4-neck round-bottom flask, with mechanical stirrer, reflux condenser, thermocouple and N₂/vacuum line, was charged DMF (13 L), Boc-L-hydroxyproline methyl ester (2.86 kg, 11.67 mol) and CDI (1.88 kg, 11.62 mol). The reaction was inerted with vacuum/$N_2$ cycle and heated to 60-65° C. The addition of CDI was endothermic, resulting in a temperature drop to 0° C. The initial slurry dissolved on warming. The reaction to intermediate was confirmed by $^1$H NMR. Bromoindoline HCl (2.60 kg, 11.09 mol) was added to the reaction mixture and aging at 60-65° C. continued. The mixture was initially a slurry, which dissolved as the reaction proceeded. The final reaction was a homogeneous reddish-orange solution. After 4 hours, the reaction showed >99.5% conversion.

To the end of reaction solution, 13 L of DMF was added. Water (26 L) was added to crystallize the product. The mixture was seeded after 2.6 L of water and again after 4 L was added. The water addition after seeding was done very slowly in order to allow a good seed bed to form. After 5 L of water was added, the mixture became very thick and eventually became unstirrable after ~10 L added. $N_2$ was bubbled into the mixture to maintain agitation. The last 16 L of water was added very quickly in order to provide enough volume to get adequate mixing. The final mixture was a very thick pink slurry; the product was needles by microscopy. The solid was isolated by filtration at 30° C. The cake was washed with 1:1 DMF/water (2×9 L, displacement) then water (2×10 L, displacement, then 24 L, slurry). The cake was dried under $N_2$. After 1 day, the cake was washed with heptane (10 L, slurry) to help remove water. The cake was dried on the filter under $N_2$ for 5 days and then transferred to trays and dried in the vacuum oven with $N_2$ bleed at 45° C. for 1 day then 55° C. for 2 days until constant weight. The product was obtained as a pale pink solid (4.75 kg) in 91.2% yield.

Intermediate A2

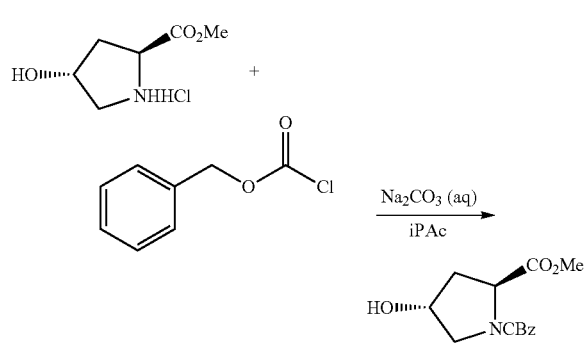

Step 1

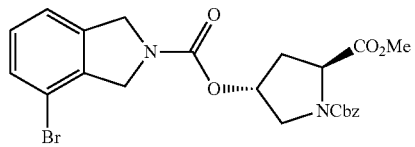 [SMILES: COC(=O)[C@@H]1C[C@@H](OC(=O)N2Cc3cccc(Br)c3C2)CN1C(=O)OCc1ccccc1]

In a 1 L round-bottom flask, hydroxyproline methyl ester (37.8 g, 208.1 mol) was dissolved in 300 mL of 1 M $Na_2CO_3$. 300 mL of iPAc was added, and the mixture cooled to 10° C. The CBZ-Cl (29.5 mL, 207.5 mmol) was added slowly via addition funnel over 30 minutes. The resulting biphasic mixture was stirred overnight to completion. The layers were separated, and the organic layer washed with 150 mL water. The organic layer was dried over $MgSO_4$ and concentrated to a crude colorless oil (54.33 g, 94% yield), which was used without further purification.

Step 2

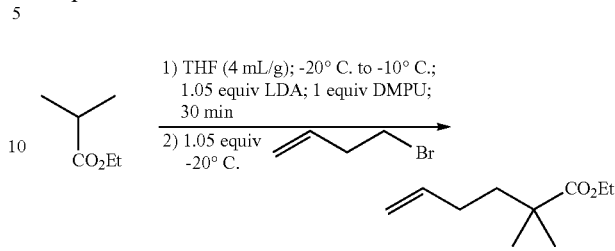

To a 3-L, 4-neck round-bottom flask, with mechanical stirrer, thermocouple and $N_2$/vacuum line, was charged DMF (190 mL), Cbz-L-hydroxyproline methyl ester (54.33 g, 194.5 mmol) and CDI (30.40 g, 187.5 mmol). The reaction was inerted with vacuum/$N_2$ cycle and heated to 65-70° C. After 1 hour, reaction showed 97% conversion to intermediate.

Bromoindoline HCl (41.42 g, 176.6 mmol) was added to the reaction mixture and aging at 65-70° C. continued. The mixture is initially a slurry that dissolves as the reaction proceeds. The final reaction is a homogeneous reddish-orange solution. After 6 hours, the reaction showed >99% conversion. To the end of reaction solution, 190 mL of MeCN was added. Water (380 mL) was added to crystallize the product. The mixture was seeded after 60 mL of water was added, and aged to develop a seed bed. The water addition after seeding was done very slowly in order to allow a good seed bed to form. During the addition the slurry becomes very thick, and vigorous stirring is necessary. The solid was isolated by filtration. The cake was washed with 1:1 DMF/water (200 mL) then water (2×200 mL). The cake was dried on the filter under $N_2$ and then for 6 hours in the vacuum oven at 50° C. The product was obtained as a pale pink solid (80.60 g) in 91% yield.

Intermediates B
Intermediate B1

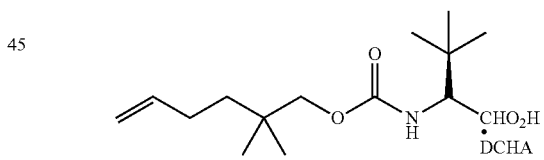

Step 1

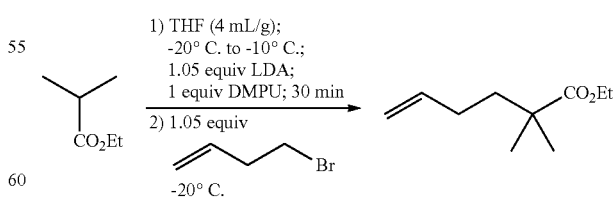

A 50-L round-bottom flask was charged with THF (10 L), diisopropylamine (3.25 L, 2.35 kg, 23.2 moles), and was cooled to around −20° C. Hexyllithium (2.3M/Hexane, 9.65 L, 22.2 moles) was added over 30 minutes at −20 to −10° C., and was aged for an additional 15 minutes after completion of the addition. Ethyl isobutyrate (2.84 L, 2.46 kg, 21.1 moles) was added over 15-30 minutes keeping the temperature between −10 and −20° C. At the end of the addition, DMPU (2.53 L, 21.1 moles) was added over a couple minutes, and the resulting solution was aged at −10 to −20° C. for 15 minutes. 4-Bromo-1-butene (2.255 L, 3.0 kg, 22.2 moles) was then added dropwise over 15-30 minutes, keeping the temperature around −20° C. The resulting solution (slurry: LiBr) was aged for 30 minutes at −20° C., allowed to warm to RT, aged for another hour, and partitioned between MTBE (21 L), and (1.5N) aqueous HCl (17 L, 25.3 moles). Layers were separated; the organic layer was washed with water (2×17 L), and concentrated (3.31 kg assay, 92% yield) to an oil, which was dissolved in PhMe (6 L), and concentrated again to "dryness" to give 4.85 kg of crude oily product (65 wt %, 3.16 kg assay, 88% isolated yield), which was used as is in the next step without further purification.

Step 2

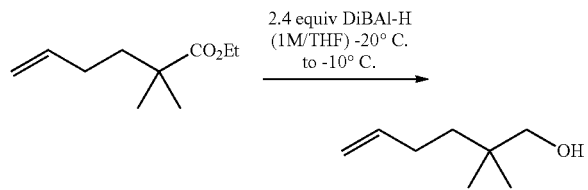

A 72-L round-bottom flask was charged with a 1M THF solution of DiBAl—H (30.7 L, 30.7 moles) and was cooled to around −20° C. Crude ester (2.9 kg, 75 wt %, 2.18 kg assay, 12.8 moles) was added over 30 minutes, keeping the temperature around −10° C. The batch was aged for 30 minutes and was reverse added over 30 minutes into a biphasic solution cooled to 0° C. made of MTBE (22 L) and a 1.5M aqueous Rochelle's salts solution. The resulting mixture was aged at 5-10° C. for 1 hour, and was allowed to warm to RT, aged 2 hours. Upon quenching, a very mild exotherm was observed. The solution was stirred at around 0° C., and starts to thicken up with some exothermic activity that was controlled by cooling. The biphasic mixture loosened up upon aging.

The layers were separated, and the organic layer was washed with (1N) aqueous HCl (17 L, 17 moles), with water (2×17 L), and concentrated to give 3.2 kg of crude oily product (51 wt %, 1.64 kg assay, 100% assay yield), which was used as is in the next step without further purification.

Step 3

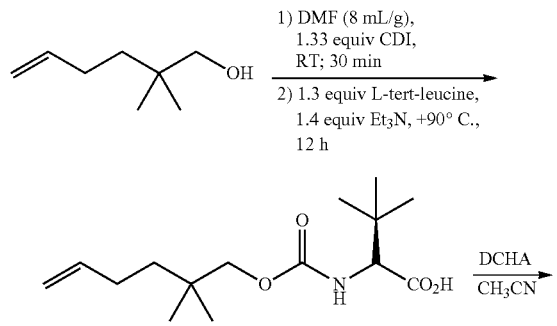

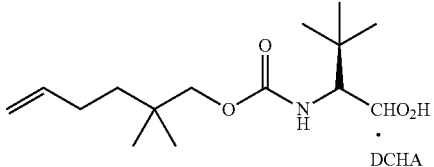

A 50-L round-bottom flask was charged with DMF (13 L), with the crude alcohol (3.21 kg, 51 wt %, 1.64 wt %, 12.8 moles), and was cooled to around +5° C. CDI (2.67 kg, 16.5 moles) was added portion-wise over 15 minutes. The resulting homogeneous mixture was aged at RT for 30 minutes.

A first portion of CDI (2.075 kg, 12.8 moles) was added, and the reaction was checked by $^1$H-NMR (CH$_2$O.CDI adduct/CH$_2$OH: δ 4.1 ppm, and 3.25 ppm). More CDI was added until δ 3.25 ppm disappeared. The reaction was exothermic, and temperature rose to 20-30° C. over 15 minutes. L-tert-leucine (2.16 kg, 16.5 moles) was added to the reaction mixture in one portion followed by the addition of TEA (2.5 L, 17.9 moles). The resulting slurry was heated to +90° C. for 12 hour, and allowed to cool to RT. The slurry turned into an homogeneous solution at +90° C. upon aging.

The solution was partitioned between MTBE (15 L), and a (0.5N) aqueous NaOH solution (19 L). Layers were separated, and the organic was discarded. To the DMF aqueous basic layer was added MTBE (24 L) and neutralize to pH~1-2 with (6N) aqueous HCl solution (about 11 L). Layers were separated, and the organic layer was washed with water (2×15 L). The organic solution was concentrated, switched to MeCN (about 50 L final, KF<1000 ppm, typically KF~500 ppm), and heated to +45° C. DCHA (0.5 L, 2.23 moles) was added over 1 hour. The salt crystallized, the solution was aged at +45° C. for 6 hour, and the slurry was allowed to cool to RT, aged a couple hours, filtered, and rinsed with MeCN (10 L). The resulting white salt was dried at +40° C. in the oven for 48 hour to give 5.1 kg of product (85% overall yield).

Intermediate B2

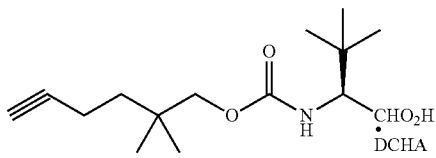

Step 1

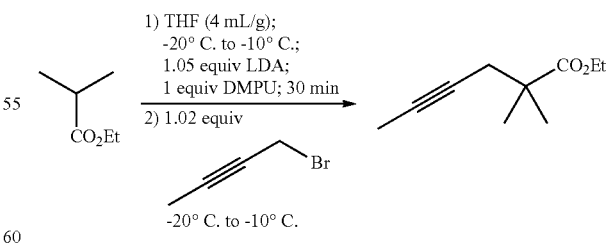

A 2-L round-bottom flask was charged with THF (520 mL), diisopropylamine (121.4 g/168.2 mL, 1.2 moles), and was cooled to around −20° C. Hexyllithium (2.3M/Hexane, 500 mL, 1.14 moles) was added over 30 minutes at −20 to −10° C., and was aged for an additional 15 minutes after completion of the addition. Ethyl isobutyrate (127.8 g/147.8 mL, 1.1 moles) was added over 30 minutes, keeping the temperature between −10 and −20° C. At the end of the addition, DMPU (132.5 mL, 1.1 mole) was added over a couple minutes, and the resulting solution was aged at −10 to −20 C for 15 minutes. 1-Bromo-2-butyne (149.2 g, 1.12 moles) was then added dropwise over 30 minutes, keeping the temperature below −10 to −5° C. At the end of the addition, the solution was aged 15 minutes and reverse added into a biphasic quench made of MTBE (1.1 L), and (1.5N) aqueous HCl (910 mL, 1.36 mole). Layers were separated, the organic layer was washed with water (2×910 mL), and concentrated to an oil, which was dissolved in PhMe (220 mL), and concentrated again to "dryness" to give the crude as an oil, which was used as is in the next step without further purification. Assay yield: 95% (176 g assay).

Step 2

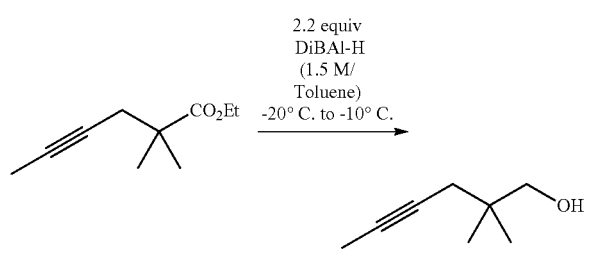

A 5-L round-bottom flask was charged with a (1.5M) PhMe solution of DiBAl—H (1.5 L, 2.3 moles), and was cooled to around −20° C. Crude ester (176 g assay, 1.05 moles) was added over 30 minutes keeping the temperature around −10° C. The batch was aged for 30 minutes, and was reverse added over 1 hour into a (3N) aqueous HCl solution cooled to −10° C. (1.6 L, 4.8 moles) keeping the temperature below 25° C. during the course of the addition.

The reaction was instantaneous at temperatures between −20 and −10° C. as judged by GC. The quench was exothermic, and was controlled by the rate of addition and cooling of the solution. Temperature of the resulting biphasic solution was kept around 20° C. pH~3.

The resulting mixture was aged at RT for 1 hour, and the layers were separated. The organic layer was washed with water (2×1.4 L), and concentrated to give the crude product as an oil (about 75 wt % by NMR, 126 g assay, 95% isolated yield), which was used as is in the next step without further purification.

Step 3

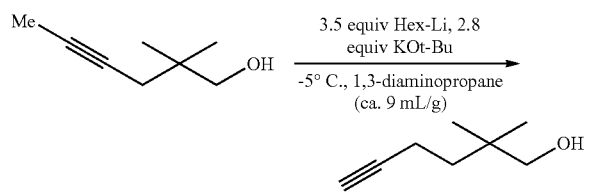

A 3-L round-bottom flask was charged with solid KOt-Bu (99 g, 0.84 mole) followed by 355 mL of 1,3-diaminopropane. The slurry was degassed, and cooled to around −5° C. (1,3-diaminopropane freezes at −10° C.). To the cooled reaction mixture was added dropwise hexyllithium (2.3M/hexane, 456 mL, 1.05 moles) at such a rate (about 45 min) that the internal temperature is maintained below 0° C. During the course of the addition the formation of a white tacky solid (Li salt of 1,3-diaminopropane) was observed. This salt turned over to the corresponding K salt, which is soluble. At the end of the addition, the batch was allowed to warm to +10° C. during a 30 minutes post-addition age. Hexane was removed by batch concentration (<25° C.). The reaction mixture was then cooled to −5° C., and the alkyne alcohol (75 wt % in PhMe, 50.5 g, 37.85 g assay, 0.3 mole) was then added keeping the temperature between −5 and +8° C. The reaction mixture was then allowed to warm to RT and aged for 2.5 hour.

The reaction mixture was then slowly reverse quenched into a cold biphasic mixture made of 850 mL of water and 530 mL of MTBE. The resulting biphasic mixture was aged at RT for 20 minutes, and the layers were separated. The organic layer was then washed with 250 mL of (6N) HCl, and with 250 mL of water, and concentrated to an oil, which was dissolved in PhMe (100 mL), and concentrated again to "dryness" (KF<250 ppm) to give the crude alcohol as an oil, which was used as is in the next step without further purification. Assay yield: 87 g of crude product at 34 wt % [NMR Assay, 29.9 g (80%)].

Step 4

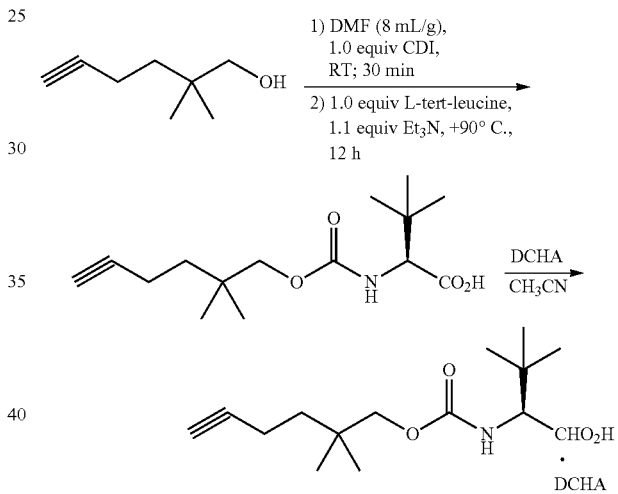

A 2-L round-bottom flask was charged with the DMF (0.5 L) solution of the crude alcohol (63.1 g assay, 0.5 moles), and was cooled to around +10° C. CDI (81.1 g, 0.5 moles) was added portion wise over 10 minutes. The resulting homogeneous mixture was aged at RT for 30 minutes. The reaction was checked by ¹H-NMR(CH₂O.CDI adduct/CH₂OH: δ 4.17 ppm, and 3.35 ppm). More CDI was added if needed until δ 3.35 ppm disappeared. An endothermic was observed when CDI was added, then upon reaction between alcohol and CDI, an exotherm occurred. Temperature rose to around 20° C. over 15 minutes.

L-tert-leucine (65.6 g, 0.5 moles) was added in one portion followed by the addition of TEA (76.7 mL, 0.55 moles). The resulting slurry was heated to +90° C. for 12 hour, and allowed to cool to RT. The slurry turned into a homogeneous solution at +90° C. upon aging. The solution was partitioned between n-heptane (1 L), and water (0.5 L). Layers were separated, and the organic was discarded.

The DMF aqueous basic layer was partitioned with MTBE (1.5 L) and was neutralized to pH~1-2 with (12N) conc. HCl solution (about 0.15 L). Layers were separated, and the organic layer was washed with water (2×1 L). The organic solution was concentrated, switched to MeCN (about 1 L final, KF~200 ppm). DCHA (89.7 mL, 0.45 moles) was added over 1 hour to crystallize the salt. The slurry was aged at RT for a couple hours and filtered. The resulting white salt was dried at +45° C. in the oven for 24 hours to give 150 g of product (72% overall yield).

Intermediates C

Intermediate C1

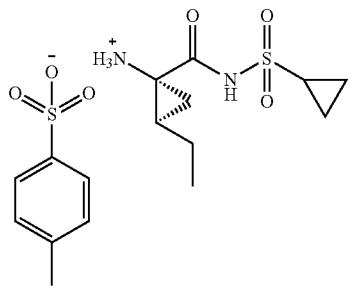

Step 1

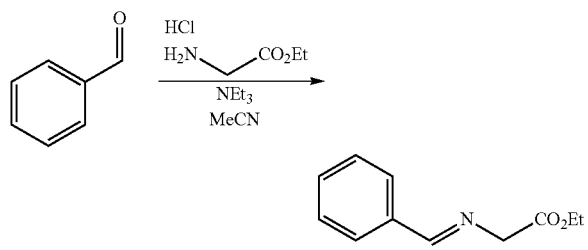

To a slurry of glycine ethyl ester HCl and NEt₃ in 9 L MeCN at 21° C., PhCHO was added over 30 minutes, and an exotherm to 38° C. was observed. The slurry was aged for 1.5 hours, and complete reaction was judged by HPLC and NMR (>98%). The slurry was filtered, and the cake was washed 2×20 L of PhMe. The filtrate was then vacuum-transferred into an extractor and diluted with 13 L of water. The phases were separated, and the organic phase was concentrated on to 20 L and taken directly into the next step. The organic layer was assayed at 6.0 kg of the imine (97% yield).

Step 2

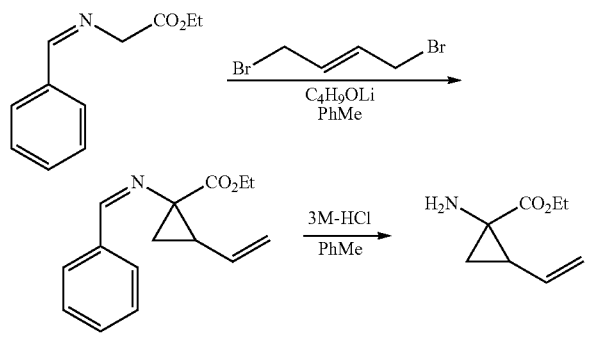

A homogeneous solution of 1,4-dibromo-2-butene in 10-L PhMe was poured into a homogeneous solution of imine in approximately 20 L of PhMe, from above. This combined solution was added, over 30 minutes maintaining a temperature of <40° C., into a slurry of lithium tert-butoxide in 30 L PhMe cooled to 10° C. Complete conversion was judged by HPLC (99%) after <3 hours.

The thin, red slurry was cooled to 15° C., and 23 L of 3M HCl was added over 30 minutes, maintaining <30° C., to get pH 0.25. The aqueous phase was vacuum transferred into a 50-L extractor, and the organic phase was washed 1× with 6 L water to recover residual amine and combined with the 3M HCl quench. The organic can be discarded after assay. The aqueous was washed 1× with 9 L PhMe to remove residual PhCHO and discarded after assay.

The aqueous was cooled to 5° C. and 50 wt % NaOH was vacuum-transferred in over 10 minutes, maintaining a temperature of <30° C., to get pH 11 and diluted with 14 L iPAc. The phases were separated, and then the aqueous was extracted again with 6 L iPAc to collect the remaining 3% of the free amine; the first extract contained 98% of the free amine. The aqueous can be discarded after assay, while the organic phase (3100 g product present; 65% yield) was ready for the Boc-protection step as is.

Step 3

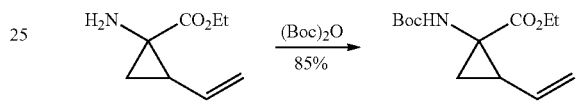

Di-tert-butyl dicarbonate was poured into a homogeneous solution of amine in iPAc, from the previous step, and stirred for 8 hours at ambient temperature; a slow exotherm to 35° C. along with low to moderate bubbling were observed. When 97% conversion was observed by HPLC, the reaction was quenched with 9 L water. The aqueous phase was then diluted with 5 L brine (sat.) and back extracted with 15 L iPAc to recover residual material. The combined organics were concentrated to an oil (4300 g; 85% yield) that was ready for resolution. No additional manipulation was needed.

Step 4

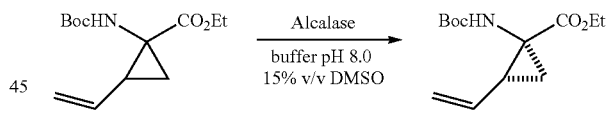

To 50 L 0.1M K₂HPO₄ (prepared by dissolving 0.87 kg in 50 L water) was added 12 L ALCALASE (NOVOZYMES) and a solution of 4.2 kg 1-tert-butoxycarbonylamino-2-vinyl-cyclopropanecarboxylic acid ethyl ester in 12 L DMSO (10° C. exotherm). The reaction was heated to 40° C., the pH was maintained at 8.0 by continuous addition of 5N NaOH (approx. 2.3 L) using a pH control unit.

After completion of the resolution (approx. 6 days) based on chiral GC assay of the 1-tert-butoxycarbonylamino-2-vinyl-cyclopropanecarboxylic acid ethyl ester, which indicated >99% EE for the desired ester enantiomer, the reaction was cooled to RT, and the pH was adjusted to pH 8.5 using 5N NaOH (approx. 0.5 L). Isopropyl acetate (50 L) was added. The aqueous layer was drained and 20 L brine added. After settling of the aqueous brine, the emulsion in the organic layer broke down under low speed agitation. The organic phase was concentrated under vacuum. 3.5 kg of a crude oil was obtained. The assay for 1-tert-butoxycarbonylamino-2-vinyl-cyclopropanecarboxylic acid ethyl ester indicated 1.96 kg were present (46.7% yield; >99% ee).

Step 5

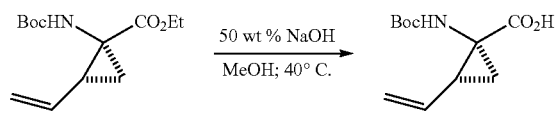

The crude, resolved ethyl-ester was diluted with 131 mL of MeOH and 27 mL of 50 wt % NaOH, and the solution was heated to 40° C. for 1 hour to get 100% conversion, by HPLC, to the acid. The homogeneous reaction was cooled to ambient temperature and diluted with 327 mL of iPAc and 327 mL of water. The phases were separated, and the organic phase was washed 1× with 163 mL water to recover remaining acid. The aqueous phases were combined, diluted with 327 mL iPAc and acidified to pH 2 with 54 mL 12M HCl. The organic phase was collected, and the aqueous phase was extracted 1× with 163 mL iPAc. The organic phases were combined and concentrated to get a red-orange oil.

Step 6

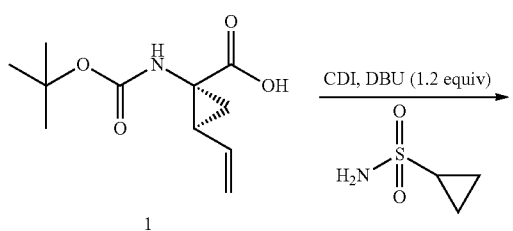

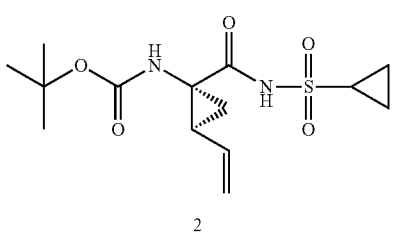

To a 150-mL round-bottom flask equipped with an overhead stirrer, a thermocouple and a condenser was charged 1 (10.3 g, 45.3 mmoles), iPAc (100 mL, ~10 V), followed by CDI (8.1 g, 49.9 mmoles, 1.1 eq). The slurry was aged at 40° C. over 1 hour. Complete formation of intermediate was confirmed by HPLC of NaOMe/MeOH quench. When conversion reached 98%, the reaction mixture was cooled to 15° C., and DBU (8.3 g, 8.1 mL, 1.2 eq) was charged followed by cyclopropanesulfonamide (6.05 g, 49.9 mmol, 1.1 eq). Batch was aged at 40° C. over 90 minutes and sampled for HPLC, 99% conversion was obtained. 3N HCl (60 mL) was charged slowly to the batch at 15° C. Layers separated, aq pH=2 to 3. Assay yield 92%. The organic layer was concentrated to 40 mL, and 120 mL of heptane was added over 10 minutes. The slurry was filtered when supernatant concentration is below 5 mg/g. The cake was washed with 50 mL of heptane. 14.6 g of slightly wet solid (2) was collected. ML loss was 4.3%.

Step 7

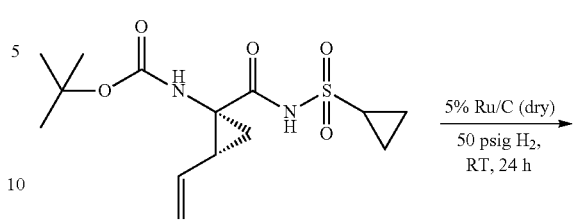

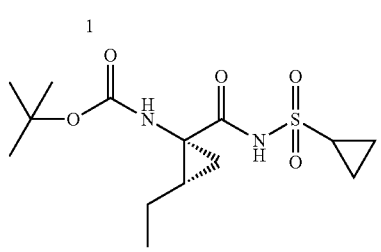

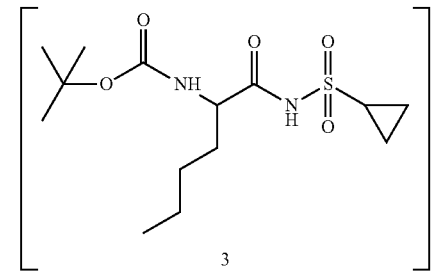

A hydrogenation vessel was charged with a solution of 1 (1.8 kg, 5.7 moles) in 10.8 L (6 V) of MeOH, followed by Ru/C (140 g, 7.5 wt %). The vessel was placed under $N_2$ (20 psig) and vented to atmospheric pressure three times to remove residual oxygen. The vessel was then placed under $H_2$ (50 psig). The reaction was characterized by an initiation period of about 30 minutes. After initiation, $H_2$ consumption was rapid and accompanied by a 6° C. exotherm. The reaction was complete in <5 hours based on $H_2$ consumption. The hydrogenation end of reaction mixture containing catalyst was stable at RT for at least 12 days (HPLC).

After 20 hours, the vessel was vented to atmospheric pressure. The reaction slurry was then transferred out of the reaction and filtered through SOLKA FLOK to yield a clear, light brown solution. The SOLKA FLOK was rinsed with MeOH (3.6 L, 2V). Filtrate injected on HPLC shows greater than 98 A % conversion to 2. The MeOH was removed under reduced pressure to recover solid product 2 (90% yield, 99.0% ee), which was used in the subsequent deprotection step.

Step 8

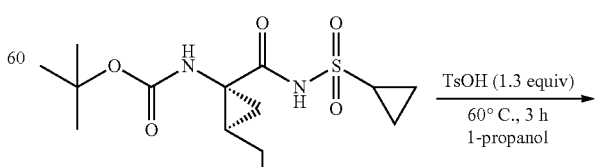

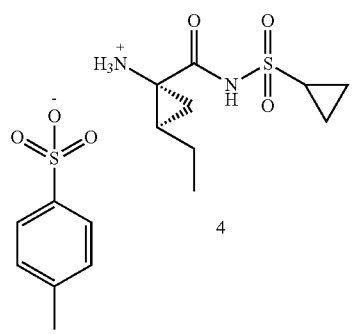

4

To a 100-L round-bottom flask equipped with an over-head stirrer, a thermocouple and a condenser was charged 2 (1.8 kg, 5.4 moles) followed by 1-propanol (32 L, 18V). To the slurry at RT was added PTSA (1.3 kg, 6.9 moles, 1.3 eq), and the slurry was aged at 60° C. over 3 hour. The batch becomes a clear solution as it is heated to 50° C. and after 1 hour at 60° C., batch forms heavy slurry (good stirring is required). The batch was allowed to cool to 45° C., and heptanes (9 L, 5 V) was added over 10 minutes, and slurry was allowed to cool to 20° C. Batch sampled for HPLC shows greater than 97% conversion. The batch was filtered and cake was washed with heptanes (7 L, 4 V), and left under vacuum at RT over 1 hour. The white solid was transferred to a tray and left to dry in a vacuum oven at 40° C. overnight. 1.6 kg (4 moles, 74%) of solid 4 (99.9 A %, 99.0% ee) was collected. Amount of ring-opened impurity was reduced to 0.08 A %. ML loss was ~12%.

EXAMPLES

Examples 1-5

Processes for Preparing Exemplary Compounds Having Structural Formula III-205

III-205

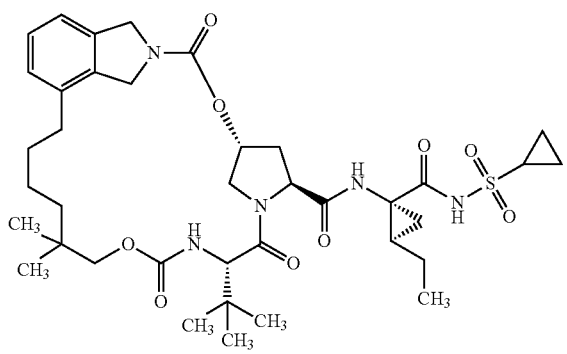

Example 1

Step 1

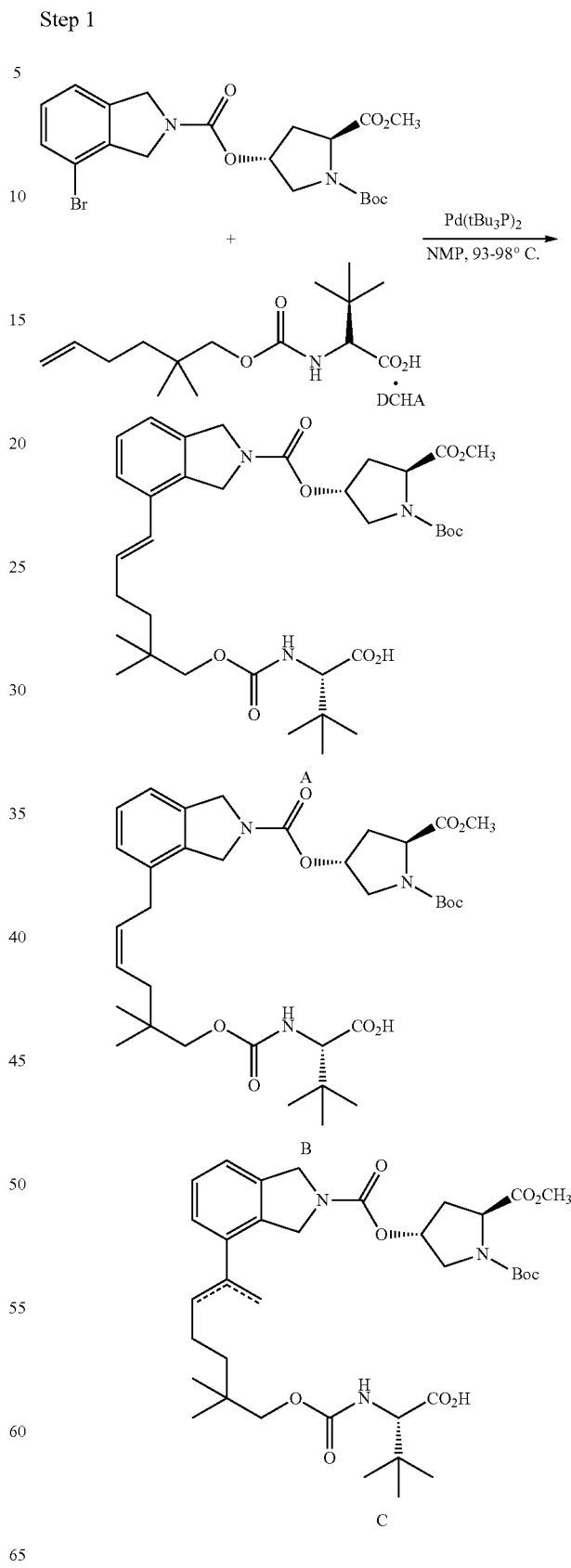

Into a clean 100-L Buchi vessel was charged 20 L of NMP followed by the solid of 3.00 kg of Intermediate A1 and 4.03 kg of Intermediate B1. Another 10 L of NMP was used to rinse the separation funnel. The resulting slurry was brought up to 100° C. in 1 hour, and the internal temperature gradually stabilized at 93-94° C. When the temperature reached ~60° C., the slurry turned into a light brown solution, and the batch was degassed and backfilled with N₂ 3×. Once the temperature stabilized at 93-94° C., the batch was again degassed and backfilled with N₂ 2×. At this time, internal temperature should fluctuate between 93-99° C.

Under the protection of N₂, the hot batch was charged with 81.2 g of Pd(tBu₃P)₂ through a funnel. Immediately after the catalyst charging, the batch was vigorously degassed and backfilled with N₂ 2×. After 20 minutes, the reaction became cloudy, and DCHA.HBr salt started to precipitate.

The reaction was sampled at 80 minutes after catalyst charging, and HPLC showed complete conversion of the bromide. The batch was cooled to 10° C. before it was filtered with filter pot. The reaction vessel was further rinsed with 24 L of iPAc, and the rinse was combined with the original filtrate. The clear brown organic filtrate was slowly pumped into 150-L extraction vessel containing 90 L of 1N HCl solution (made from 7.5 L of concentrated HCl and 82.5 L of water) with vigorous stirring. After the layer is cut, sampling of the aqueous layer showed <0.1 g/L of products.

The aqueous layer was pumped back into the extraction vessel and extracted again with 24 L of iPAc. After the layer was cut, the organic layers were combined and washed twice with 50 L of 1N HCl solution (made from 4 L of concentrated HCl and 46 L of water) followed by washing twice with 50 L of water. The wet iPAc layer was pumped into 100-L round-bottom flask and treated with 1173 g of Darco G60 at RT with stirring for 30 minutes before the slurry was filtered through Solka Flok (~1 kg), followed by washing with another 4 L of iPAc.

Total weight of 38.1 kg of solution was collected (d=0.900 g/mL), and the product solution in iPAc was transferred to Buchi vessel and chilled to −15° C. The batch was degassed and backfilled with N₂ 3× before standing at −15° C.

Step 2

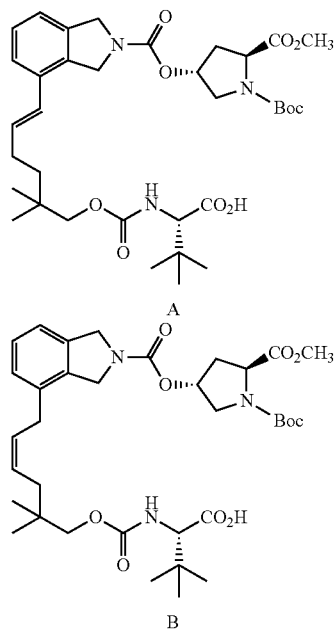

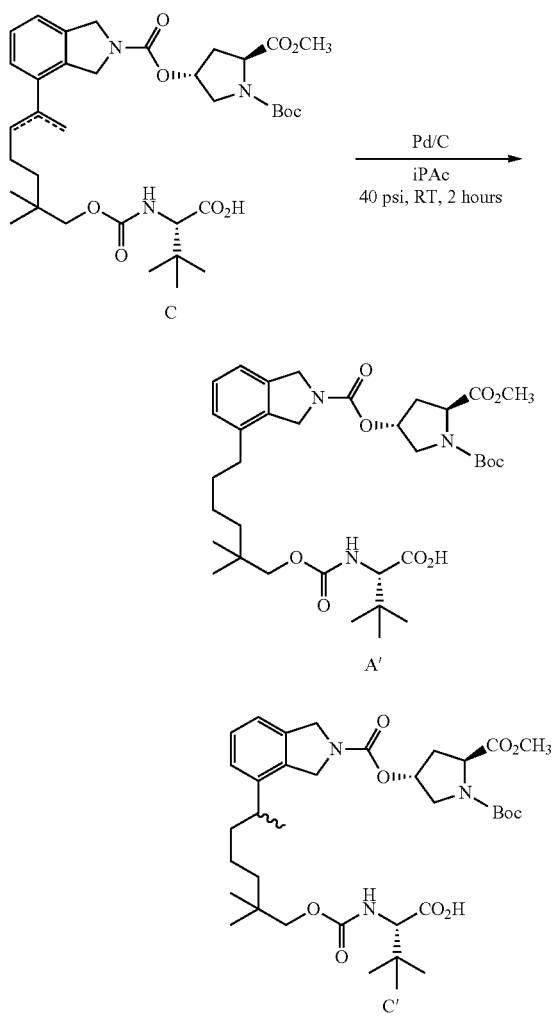

The cold batch of products from step 1 stored in Buchi vessel was split into two bathes of 18.7 kg (batch one) and 19.2 kg (batch two). Each batch was transferred into 10-G (10 gallon) Hastelloy hydrogenation vessel. 1.00 kg of 10% Pd/C was slurred with 4 L of iPAc and transferred into the hydrogenation vessel. Hydrogenation condition: 40 psi, RT.

Sampling of the first batch at 127 minutes showed >99% conversion and sampling of the second batch at 120 minutes showed 98.6% conversion. The second batch was further hydrogenated for another 30 minutes, and >99% conversion was eventually achieved. The batch was transferred into carboys, and Hastelloy hydrogenation vessel was rinsed with 20 L of iPAc.

The two batches were filtered (under the protection of N₂ to prevent combustion of Pd/C catalyst) through Solka Flok followed by rinsing the cake with two carboys of iPAc rinse. Final rinse of cake with 2 L of iPAc further took the concentration of product in end stream down to <0.5 g/L. The filtrates were collected and transferred into the Buchi vessel through 1-μm inline filter. The batch was chilled to −15° C. and degassed and backfilled with N₂ 3× before storage. Assay Yield: 96% for steps 9 and 10.

Step 3

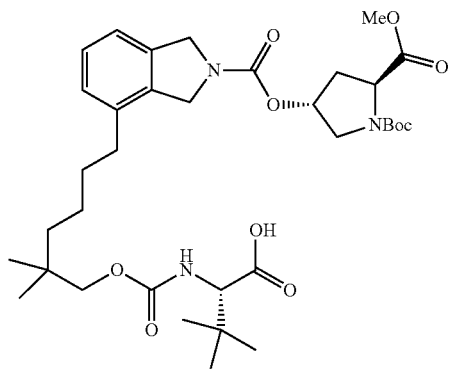

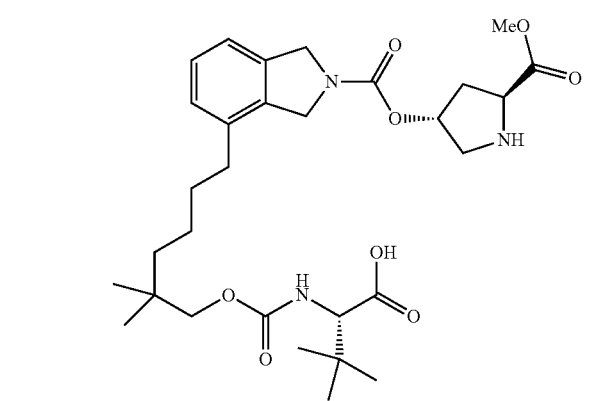

The solution of saturated Boc-acid in iPAc (74.98 kg, 53.8 g/kg, 4033.7 g substrate, 5.97 mol) was fed into a 50-L, 4-neck round-bottom flask, with mechanical stirrer, batch concentrator, thermocouple and $N_2$/vacuum line with distillation at 25-30° C., 28-29 inches Hg, maintaining constant volume of ~20 L. After the batch transfer was complete, an additional 30 L of iPAc was fed distilled to azeotropically remove water. The saturated Boc-acid is unstable at 60° C. or for prolonged time at RT in the presence of air. Care should be taken not to overheat the reaction. The final batch KF was 250 μg/mL. The batch was maintained and stored under $N_2$ at all times.

To the batch 10 L of iPAc was added (total volume was 30 L). The batch was heated to 30° C. and placed under vacuum to obtain a slow distillation. MsOH (1695.5 g, 17.64 mol) was diluted with 5 L of iPAc and slowly fed into the batch over 30 minutes with continued slow distillation. The reaction was aged for 2 hours at 30-35° C. The reaction went to 99% conversion. The batch was then concentrated at 20-25° C., 29-30 inches Hg to ~15 L and transferred into a poly jug for transport. The transfer was completed using iPAc (1 L).

The amino acid solution was used directly in the next step. The solution was not assayed; the yield was calculated based on 100% conversion after accounting for sampling throughout the sequence. The final solution of amino acid with MsOH in iPAc was unstable at RT and over prolonged times in the freezer, generating up to 4-5% of the diacid from hydrolysis.

Step 4

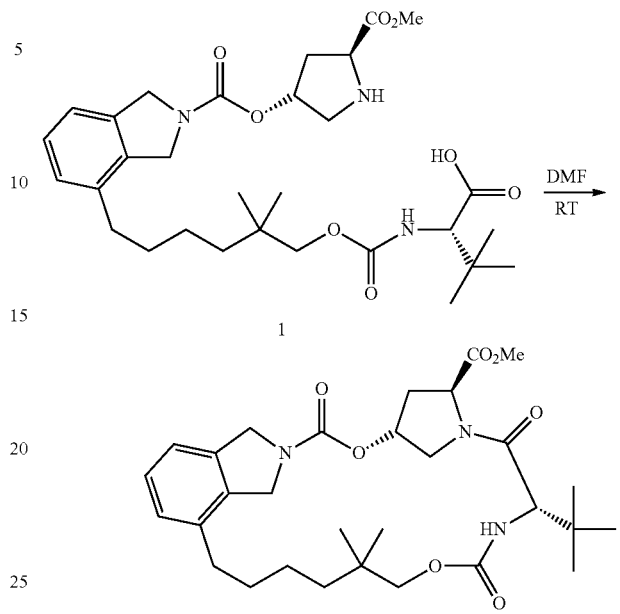

At 20° C., a 500-G vessel was charged with DMF (400 L), DMAP (0.330 kg, 2.95 mol), and DIPEA (2.9 kg, 22.4 mol). The solution was set stirring, and the iPAc solution of pre-macrocycle 1 (5.9 mol, 0.369 mol/kg) was added after the DMAP has dissolved (~10 minutes). An exotherm of 2° C. was observed upon substrate addition. The DIPEA charge was calculated as follows: 0.8 equivalents plus the number of equivalents of acid used in previous step. At 20° C., HATU (3.15 g, 8.3 mmol) was charged as a solid in one portion. One hour after the HATU charge, the reaction was judged complete by HPLC (>99 A % conversion). To the batch was added water (110 L), keeping the temperature below 25° C., as this addition was strongly exothermic.

A slurry of previously generated seed (1.5 mol % based on assay) was added, and the batch was aged overnight. A visual inspection of the batch revealed that the seed did not hold. Consequently, additional water (75 L) was charged to the batch over two hours. After a 3-hour age, the batch had self-seeded. An additional slurry of seed was also added (1.0 mol %). The remaining water (215 L) was added, and the batch was aged overnight. The batch can be heated to 50° C. after water addition and cooled to 20° C. to improve crystallinity. The solution was filtered and the filter cake was rinsed with water (50 L×2). The resulting wetcake was dried under vacuum with $N_2$ sweep overnight. Yield=59%, 2.88 kg, 68 wt %, 6 A % dimer.

To a 100-L round-bottom flask equipped with over-head stirrer, thermocouple, reflux condesor, and $N_2$ inlet was charged iPAc (6.1 L) and MeCy (8.9 L). After a 5-minute agitation, the ester was added, and the batch was warmed to 50° C. Following a 2-hour age, the remaining MeCy (33.9 L) was added over 1.5 hours, and the white slurry was aged an additional hour, upon which time the batch was allowed to cool to 20° C. and aged overnight. The batch was filtered and dried under reduced pressure in a vacuum oven with a $N_2$ sweep over the weekend. Yield=1.9 kg, 97% recovery, 98.5 wt %, 0.7 A % dimer, 1.5% weight loss by TG.

Step 5

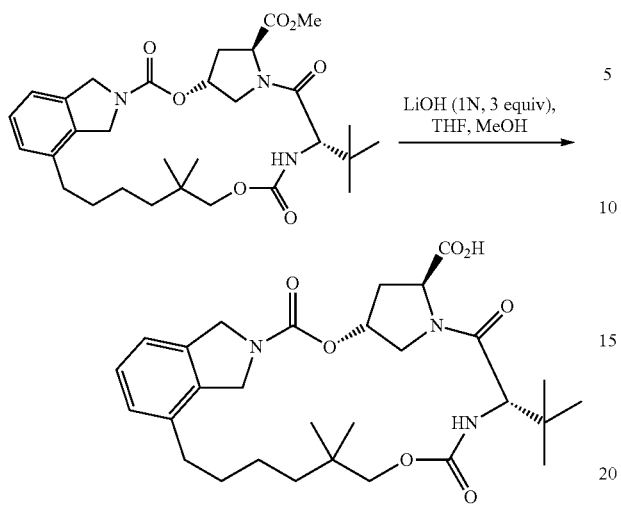

A 100-L extraction vessel equipped with over-head stirrer and thermocouple was charged with a THF solution of ester and cooled to 5° C. An aqueous solution of lithium hydroxide (1N, 9.6 L, 9.6 mol) was added dropwise via addition funnel over 30 minutes keeping the temperature below 15° C. With the same addition funnel, MeOH was added over 10 minutes at 15° C., after which the white, heterogeneous mixture was allowed to warm to RT. Upon warming, the solution became homogeneous. After about 30 minutes, the solution turned from light yellow to dark brown. The reaction, sampled at this time, was judged complete by HPLC analysis (>99.9 A % conversion). The batch was cooled to 5° C. and treated with 1N HCl to quench the excess LiOH. After addition, the solution was warmed to 20° C. and diluted with iPAc (18 L, 10 vol). After agitating for 15 minutes, the layers were allowed to separate and the organic layer was collected (1.7 kg, 98% AY).

The iPAc solution was treated with DARCO KB-G (40 wt %) at 20° C. for 10 minutes, and the solution was filtered through SOLKA FLOK, followed by filtration through a 5 μm in-line filter (1.7 kg, >99% recovery). The iPAc solution was concentrated under reduced pressure, keeping the temperature below 25° C., to 10 L. An additional 10 L of iPAc was added, and the batch was concentrated to 10 L. The acid crystallized from solution as water was azeotropically removed. The solution was diluted with DMF (8 L), and the concentration was continued until the final batch volume was 8 L. The batch was diluted with DMF (2 L) and iPAc (8 L).

Step 6

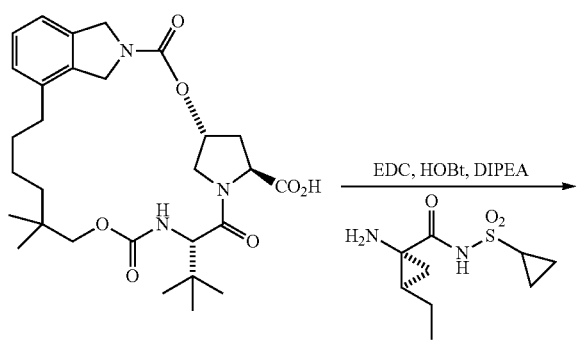

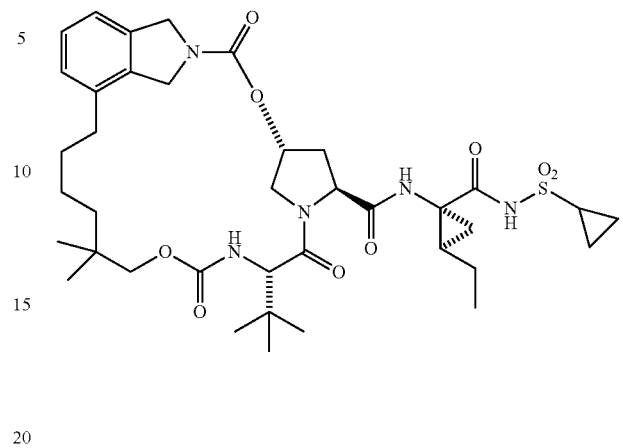

A 100-L vessel equipped with an overhead stirrer, $N_2$ inlet, thermocouple was charged with macrocyclic acid solution. The solution as set stirring, and Intermediate C1 was added as a solid. Upon dissolution (<10 minutes), HOBt was added as a solid. The batch was cooled to 15° C., and DIPEA was added via addition funnel while maintaining the temperature below 20° C. Solid EDC was added. No change in temperature as observed. After 3 hours, the reaction as judged complete by HPLC (>99.8 A % conversion, 91% AY, 2.1 kg).

The batch was transferred to a 100-L extraction vessel, cooled to 10° C., diluted with iPAc (16.8 L) and water (33.6 L). The mixture was agitated for 10 minutes. The layers were allowed to separate, and the aqueous layer was discarded (pH=6-7). Aqueous HCl was added to the iPAc layer, and the solution was agitated for 10 minutes. The layers were allowed to separate, and the aqueous layer was discarded (pH=1-2). The iPAc solution was then treated with water/brine (15.1 L/1.7 L). After 10 minute agitation, the layers were allowed to phase separate, and the aqueous layer was discarded (pH=2-3). The iPAc solution was concentrated and flushed with ethanol (50 L) until there was 2.5 mol % iPAc in ethanol, as judged by $^1$H NMR spectroscopy. Yield=2.02 kg, 87% AY.

Step 7

The solution in ethanol from previous step was charged to a 75-L round-bottom flask through a one-micron in-line filter, then rinsed with additional 2 L ethanol. 20% KOH wt/v in ethanol (930 g mixed with 7 L ethanol) was added, and the batch was heated to 50° C. KOH in ethanol was added slowly, 1 L first; the batch was seeded with 15 g seed; 1 L KOH in ethanol was added, and the batch was aged for 20 minutes. The batch was allowed to rest over 30 minutes, then rinsed with 2 L ethanol and aged at 50° C. for 1 hour. The batch was then cooled to RT over 3 hours, and aged at RT overnight. The batch was filtered, washed with 3 L ethanol, and air-dried until ethanol was completely removed. Weight of the solid: 2164 g (93% wt. pure K salt, 91% after correcting for purity and the seed).

Example 2

Steps 1&2

Steps 1 and 2 were performed according to Example 1, Steps 1 and 2, above.

Step 3

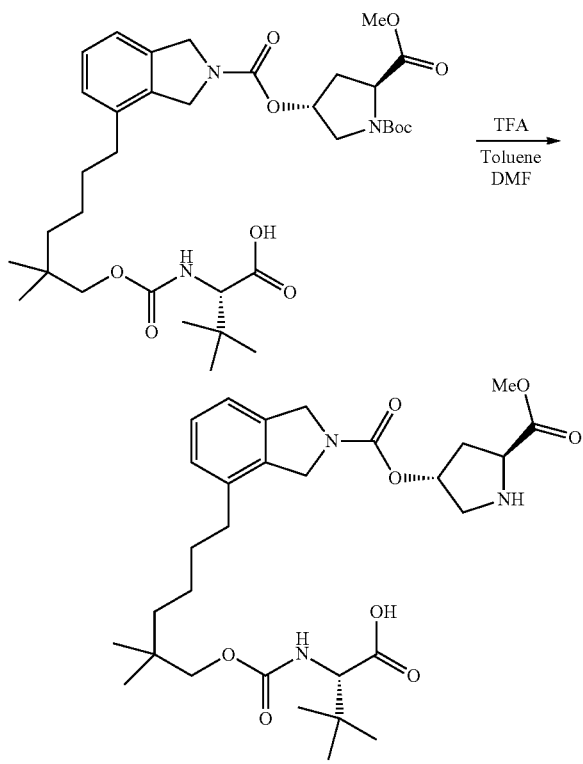

The iPAc solution of the Boc-protected product of Step 2 (approximately 14.2 kg), was charged to a 400-L vessel. The solution was solvent-switched to PhMe by distilling under reduced pressure to volume of 20 L, charging PhMe (116 kg) to the vessel and re-distilling to a volume of 45 L. The volume was made up to 68 L with PhMe, giving an analysis result of KF=90 µg/mL and 0.17% iPAc, and the solution stood at 20° C. overnight.

The batch was cooled to 5° C., and TFA (47.9 kg) charged to the vessel at below 11° C. The mixture was warmed to 23° C. and stirred at this temperature for 80 minutes. HPLC gave reaction complete, <1% starting material present. The mixture was concentrated to a volume of <40 L under reduced pressure at <30° C., toluene (116 kg) charged to the vessel, and this solution was concentrated to a volume of 40 L at <40° C. Analysis of this solution indicated a 1:1 ratio of product: TFA. DMF (132 kg) was charged to the batch, and the batch was concentrated to a volume of 80 L. The solution was used as is in the next step, assuming a quantitative yield of the free amine (12.1 kg).

Steps 4-7

Steps 4-7 were performed according to Example 1, Steps 4-7, above.

Example 3

Step 1

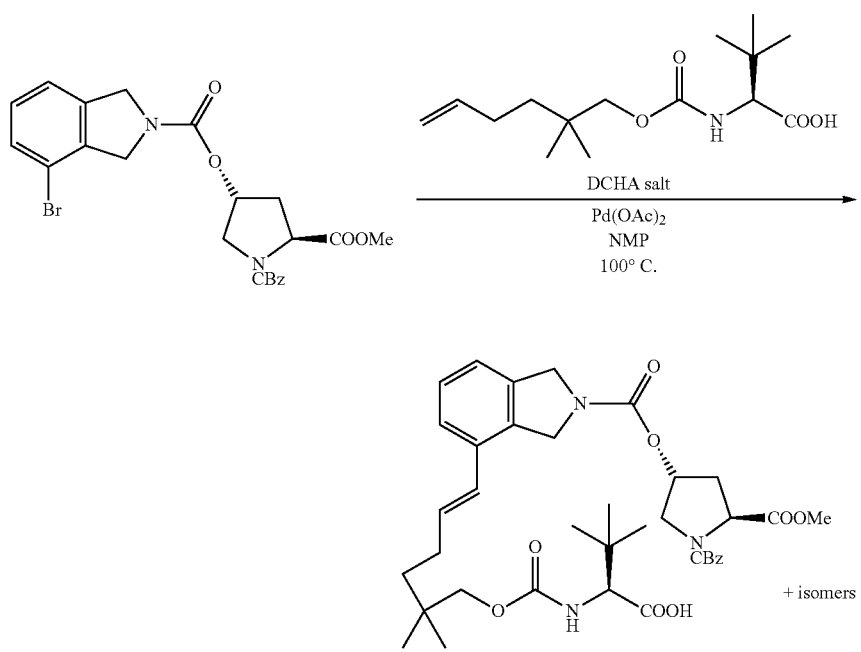

A 3-neck 1000-mL round-bottom flask was charged with Intermediate A2, Intermediate B1, NMP (75 mL), and an over-head stirrer. The stirred heterogeneous solution was warmed to 45° C. Upon dissolution of all solids, the red-orange solution was subjected to 5 N$_2$/vacuum purge cycles (45 seconds N$_2$/45 seconds house vacuum 5×) and placed under N$_2$. Degassing at RT resulted in formation of an intractable foam.

The catalyst, Pd(OAc)$_2$, was weighed out on an analytical balance in the air and then quickly transferred to the reaction solution. After the catalyst charge, the solution was subjected to 3 N$_2$/vacuum purge cycles, placed under N$_2$, and warmed to 100° C. The reaction solution darkened over time after which a black precipitate formed. This coincided with the end of reaction (1.5 hours). After 2 hours, the solution was sampled and judged to be complete by HPLC (>99 A % conversion). Upon cooling, the heterogeneous reaction was charged with BHT and transferred to the hydrogenation vessel. The original reaction vessel was rinsed with NMP (10 mL×2) and the NMP was combined with the reaction solution in the hydrogenation vessel. The product was thought to be oxygen sensitive; consequently, a small amount of BHT is always added; the batch was stored at 5° C.

Step 2

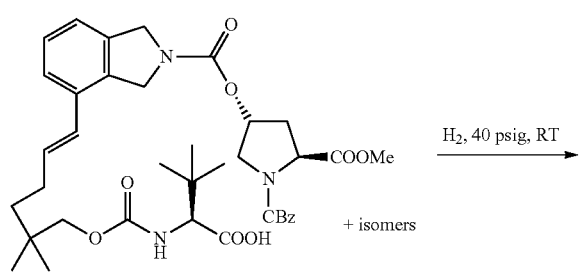

To a solution of the product of Step 1 was added Pd/C. The solution was transferred to a hydrogenation vessel, subjected to five vacuum/N$_2$ purge cycles, and placed under H$_2$ gas (40 psig) at RT. After an overnight age, the solution was vented to atmospheric pressure and placed under N$_2$ gas. The black solution was filtered through a thin layer of S$_{OLKA}$ $_{FLOK}$, and the filter cake was rinsed with DMF (1000 mL). The DMF/NMP solution of product was carried on to the macrocyclization.

Step 3

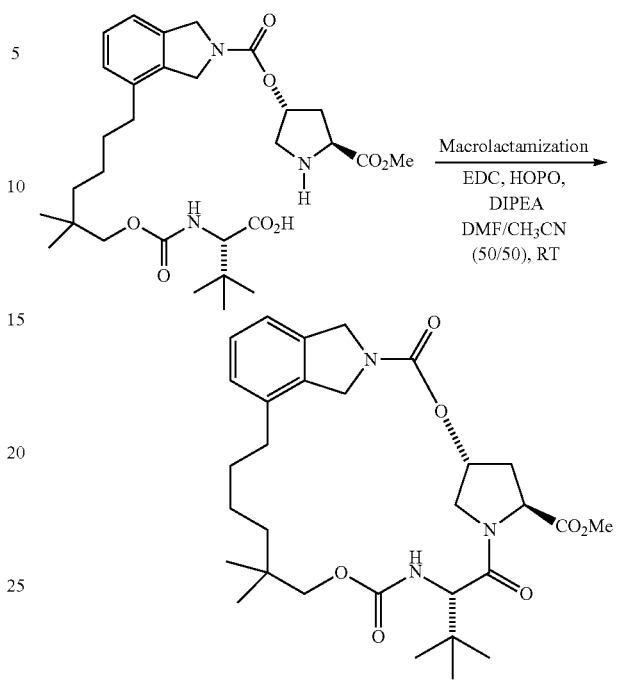

At 20° C., the DMF/NMP solution of pre-macrocycle 1 (87.0 mmol) was added to a 12-L flask containing HOPO (14.5 g, 130.4 mmol). DMF and MeCN were added. After 10 minutes, DIPEA (30.3 mL, 174.0 mmol) was added to the stirred solution followed by EDC.HCl (33.3 g, 174.0 mmol). The mixture was stirred at RT overnight. The reaction was judged complete by HPLC (>99 A % conversion). During the age, DCHA.HCl crystallized from solution. The batch was concentrated on a R$_{OTOVAP}$ under vacuum (~20 Torr) with the bath temperature set to 50° C. Concentration was judged complete when distillate condensation halts.

The solution was then filtered through a thin layer of S$_{OLKA}$ F$_{LOK}$ to remove DCHA.HCl. To the solution was added water (850 g, 30% total charge) over 30 minutes, keeping the solution at 22° C. At this point, previously generated seed (350 mg, 0.7 wt % based on ideal yield) was added, and the batch was aged for 0.5 hour. A visual inspection of the batch revealed that a thin seed bed was present. Additional water (850 g, 30% total charge) was added to the batch over 1 hour. Upon completion, the batch was held for 2 hours, and the remaining water (1.1 kg, 40% total charge) was added to the slurry over 2 hours. The batch was allowed to stir overnight (16 hours). The solution was filtered, and the filter cake was rinsed with water (500 g×3). The resulting wet cake was dried under vacuum with N$_2$ sweep for 20 hours. 53.6 g, 67 wt % (66% isolated yield)

Step 4

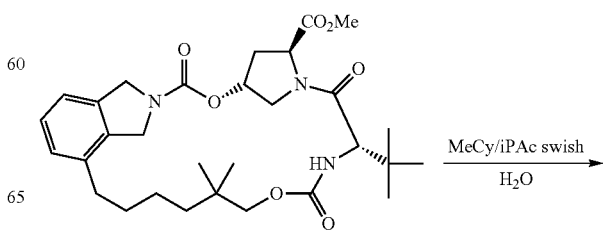

-continued

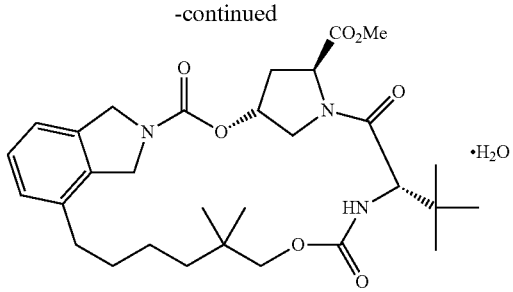

The ester was slurried in iPAc (560 mL) and warmed to 45 DCHA. After 15 minutes, the homogeneous solution was cooled to RT and split into two equal portions.

In the first portion, the solution was concentrated to a macrocyclic ester concentration of 189 mg/g), warmed to 50 DCHA, and water (1.25 mL, 2.25 equiv) was added. After 10 minutes, previously generated seed (85 mg, 0.5 wt %) was added to yield a thin crystalline seed bed. After 30 minutes, methylcyclohexane (470 mL) was added over 1.5 hours, and the batch was allowed to cool to RT over approximately 2 hours. After an overnight age, the solution was filtered, and the light brown filter cake was washed with MeCy/iPAc (98:2 MeCy/iPAc; 50 mL) and dried overnight under vacuum with a $N_2$ sweep. 15.7 g, 92 wt %, 86% recovery.

To the second portion of cooled, homogenized solution was added DARKO-KB-G (20 wt %). After 40 minutes, the solution was filtered through a thin layer of SOLKA FLOK. The filter cake was rinsed with iPAc (33 mL×3). The combined iPAc layers were concentrated until the macrocyclic ester concentration reached 189 mg/g. Then, previously generated seed (85 mg, 0.5 wt %) was added to yield a thin crystalline seed bed. After 30 minutes, MeCy (470 mL) was added over 1.5 hours, and the batch was allowed to cool to RT over approximately 2 hours. After an overnight age, the solution was filtered, and the light brown filter cake was washed with MeCy/iPAc (98:2 MeCy/iPAc; 50 mL) and dried overnight under vacuum with a $N_2$ sweep. 15.2 g, 96 wt %, 87% recovery. Overall yield=29.0 g, 53.5%.

Example 4

Steps 1-5

Steps 1-5 were performed according to Example 1, Steps 1-5, above.

Step 6

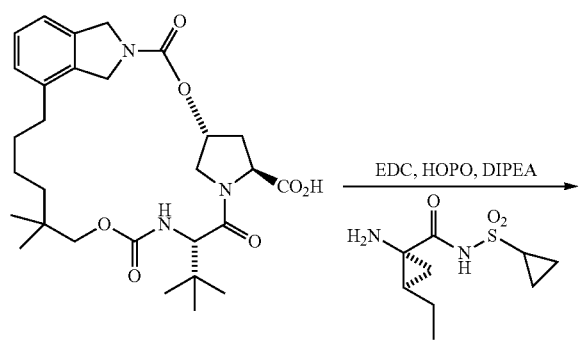

-continued

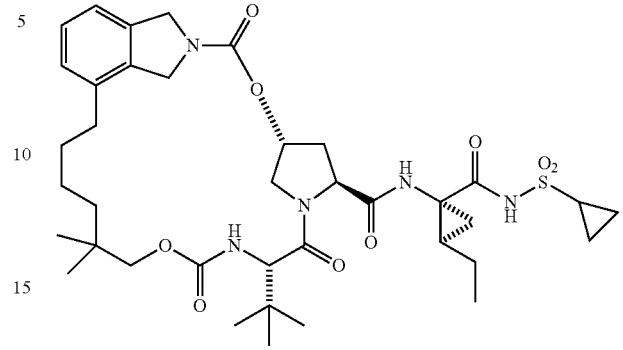

A 500-mL round-bottom flask equipped with an overhead stirrer, $N_2$ inlet, thermocouple was charged with macrocyclic acid solution. The solution was set stirring, and Intermediate C1 was added as a solid. Upon dissolution (<10 min), HOPO was added as a solid. The batch was cooled to 15° C., and DIPEA was added via addition funnel while maintaining the temperature below 20° C. Solid EDC was added. No change in temperature was observed. After 3 hours, the reaction was judged complete by HPLC (>99.8 A % conversion, 94% AY, 7.01 g).

The batch was transferred to a 500 mL extraction vessel diluted with iPAc (100 mL) and water (100 mL). The mixture was agitated for 10 minutes. The layers were allowed to separate, and the aqueous layer was discarded (pH=6-7). Aqueous HCl was added to the iPAc layer, and the solution was agitated for 10 minutes. The layers were allowed to separate, and the aqueous layer was discarded (pH=1-2). The iPAc solution was then treated with water then brine (50 mL/50 mL). After 10 minutes of agitation, the layers were allowed to phase separate, and the aqueous layers were discarded (pH=2-3). The iPAc solution was concentrated and flushed with ethanol (50 mL) until there is 2.5 mol % iPAc in ethanol, as judged by $^1$H NMR. Yield=6.86 g, 92% AY.

Step 7

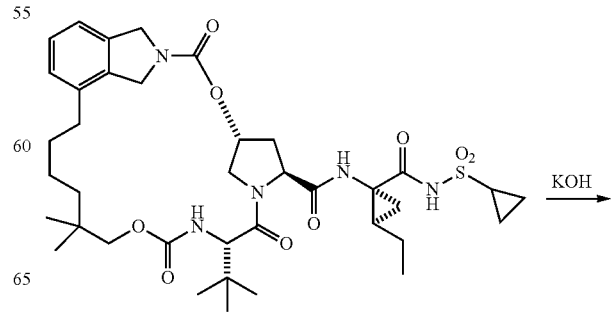

-continued

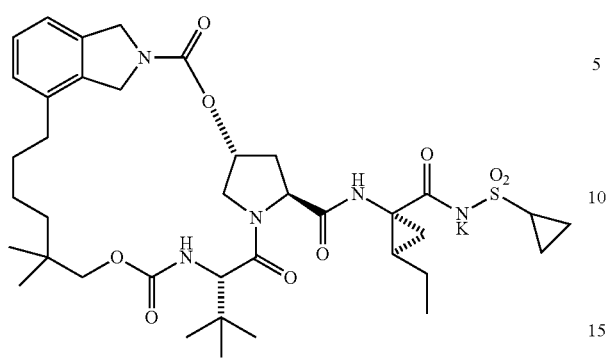

To a 300-mL round-bottom flask was charged 188 g of free acid solution (272.7 mg/g), followed by 72 g of free acid ethanol vessel flush (8.3 mg/g). The solution was mixed at RT to homogenize. By assay, free acid was ~51.9 g or 68.6 mmols. The solution was heated to 49° C., then 15.1 mL of 0.5M KOH solution in ethanol (made from 50% KOH and ethanol) was charged into the vessel. The mixture was then heated to 51° C., before charging ~59.5 g of seed slurry (8.75 wt % K-salt in ethanol). The seed bed was sonicated and aged for 1 hour at ~53° C. The seed loading was ~10 wt % or ~5.2 g of K-salt. Upon aging the seed bed, 142 mL of 0.5M KOH solution in ethanol was charged over ~10 hours while maintaining the batch at ~53° C. The batch was aged overnight, and a supernatant sample was taken. The batch was filtered in a glass sintered filter with 55° C. on filter jacket, then washed with 180 mL of warm ethanol (30-40° C.). Mother liquor and wash were ~510 mL in volume with a pH~8.5. The batch was dried by applying vacuum on bottom of filter, with jackets at 55° C., and top of filter was open to ambient air at 20° C. and 43% RH. 55.3 g of K-Salt were packaged with a KF~5.3%, residual ethanol ~0.07 wt %. The purity of the cake was 98.9 A % III-205, 0.8 A % Dimer, 0.2 A % Trimer, and some minor low level impurities. The yield of the step was 85.9% taking the seed contribution into account.

Example 5

Step 1

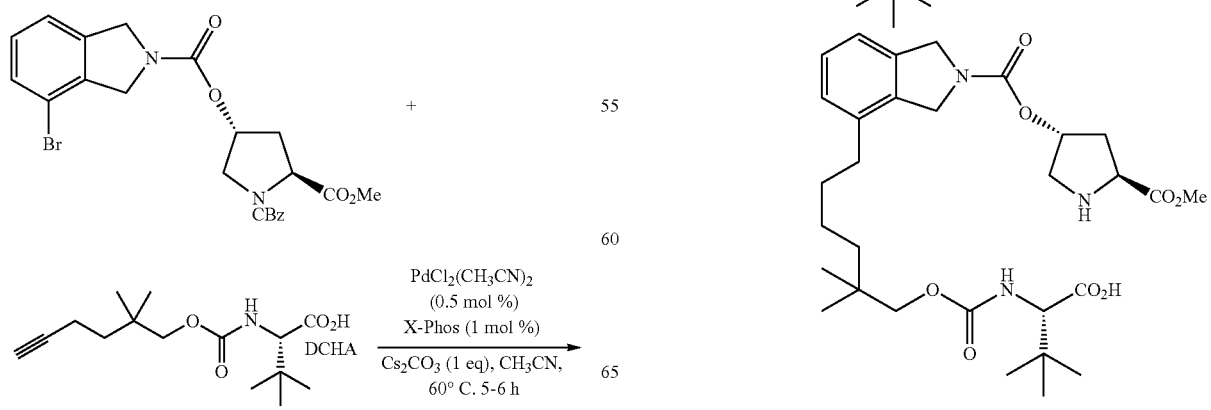

-continued

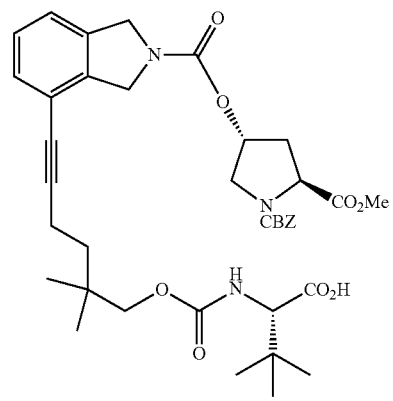

A flask was charged with Intermediate A2 (10 g), Intermediate B2 (11.1 g), Cs$_2$CO$_3$ (6.5 g), PdCl$_2$(CH$_3$CH)$_2$ (103 mg), ligand (X-Phos, 379 mg or tBu$_3$P, 160 mg), and acetonitrile (50 mL). The solution was degassed via 5 N$_2$/vacuum cycles and then warmed to 60° C. After two hours, analysis by HPLC showed the reaction was complete. The solution was quenched with water (100 mL) and iPAc (200 mL). The aqueous was separated, and water (100 mL) was added to the organic solution. The aqueous was separated again, and HCl (1N, 100 mL) was added to the organic layer. After aging for 30 minutes, the solution was filtered to remove DCHA.HCl, and the aqueous was separated. The organic layer was rinsed with saturated brine (50 mL). The solution was concentrated to dryness and redissolved in iPAc (80 mL). This solution was used in the subsequent hydrogenation. Assay yield: 14.4 grams, 103% AY.

Step 2

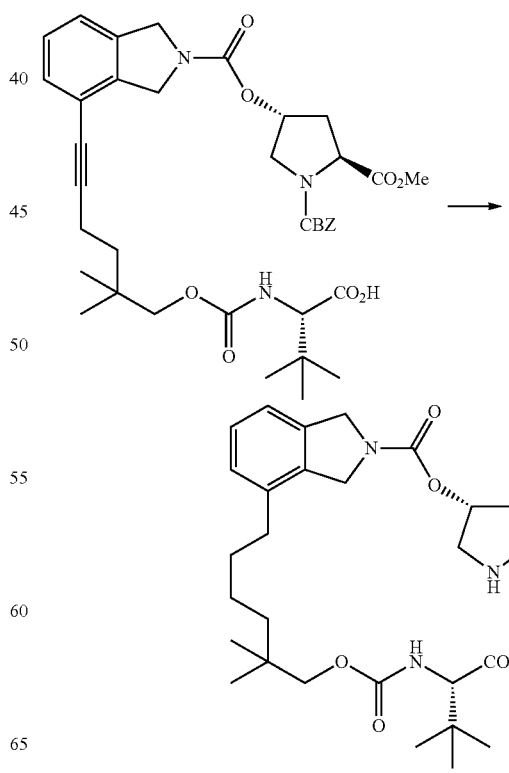

The iPAc solution of the product of Step 1 (40 mL) was charged with Pd/C (3 g, 10% Pd/C) and DMF (40 mL), degassed with vacuum/$N_2$ purges 3× and placed under $H_2$ (80 psi). After an overnight age, the solution was filtered through SOLKA FLOK. The SOLKA FLOK was rinsed with DMF/iPAc (200 mL 50/50) and concentrated on the ROTOVAP to remove the iPAc. The DMF solution was used in the macrocyclization step. Approx. yield=4.69 grams, 96%.

Step 3

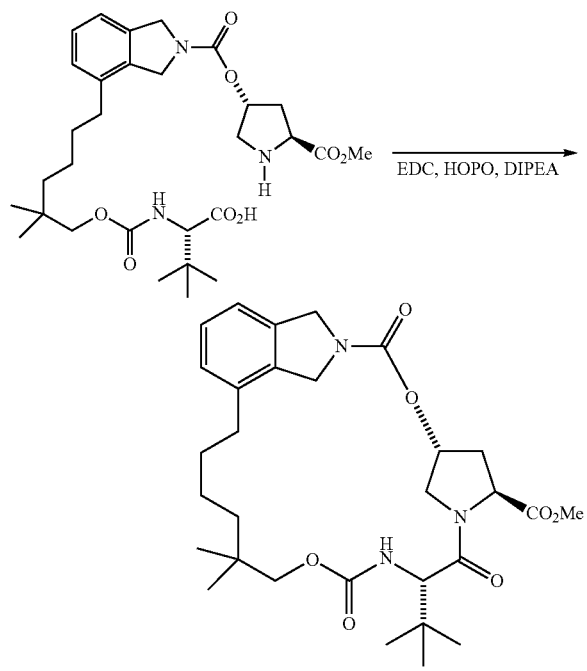

DMF (490 mL) was added to DMF solution containing the product of Step 2. To this was added 2-hydroxypyridine-N-oxide (950 mg), 4-dimethylaminopyridine (480 mg), DIPEA (1.52 mL), EDC.HCl (1.6 g). The solution was aged overnight. To drive the reaction to completion, additional 2-hydroxypyridine-N-oxide (140 mg), DIPEA (0.23 mL) and EDC.HCl (0.245 g) was added. After 3 hours the reaction was judged complete. Water (500 mL) was added to crystallize the macrocyclic product. The solution was filtered, and the white solid was dried in vacuo overnight. Yield: 3.36 g, 74% yield.

Example 6

The X-ray powder diffraction (XRPD) patterns for solid phases of a potassium salt of exemplary Compound III-205 were generated on a PHILIPS ANALYTICAL X'PERT PRO X-RAY DIFFRACTION SYSTEM with PW3040/60 console. The diffraction peak positions were referenced by silicon, which has a 2 theta value of 28.443 degree. A PW3373/00 ceramic Cu LEF X-ray tube K-ALPHA radiation was used as the source. The experiments were run at ambient condition unless noted otherwise.

The solid-state carbon-13 nuclear magnetic resonance (NMR) spectra were collected on a BRUKER AV500 NMR spectrometer using a BRUKER 4 mm double resonance CPMAS probe. All spectra were collected utilizing proton/carbon-13 variable-amplitude cross-polarization (VACP) with a contact time of 2 ms, magic-angle spinning (MAS) at 10 kHz, and TOSS spinning sideband suppression. A line broadening of 40 Hz was applied to the spectra before Fourier Transformation. Chemical shifts are reported on the TMS scale using the carbonyl carbon of glycine (176.03 ppm.) as a secondary reference.

Ethanol Solvate A of Exemplary Compound III-205 Potassium Salt

Ethanol solvate A was obtained by crystallization of the potassium salt of exemplary Compound III-205 in ethanol/water (10 ml/1 ml) at 50° C. or higher. It is only stable in contact with the solvent; the XRPD pattern was obtained using wet cake. FIG. 1 is the XRPD pattern for ethanol solvate A of the potassium salt of exemplary Compound III-205, with selected d-spacings listed in Table 1.

TABLE 1

| 2θ(2 theta)(degrees) | d-spacing (Å) |
|---|---|
| 6.1 | 14.4 |
| 7.1 | 12.4 |
| 8.7 | 10.2 |
| 10.3 | 8.56 |
| 12.3 | 7.22 |
| 13.6 | 6.53 |
| 16.1 | 5.51 |
| 20.9 | 4.24 |
| 22.1 | 4.01 |

X-ray powder diffraction: ethanol solvate A of the potassium salt of exemplary Compound III-205

Ethanol Solvate B of Exemplary Compound III-205 Potassium Salt

Figure 2:
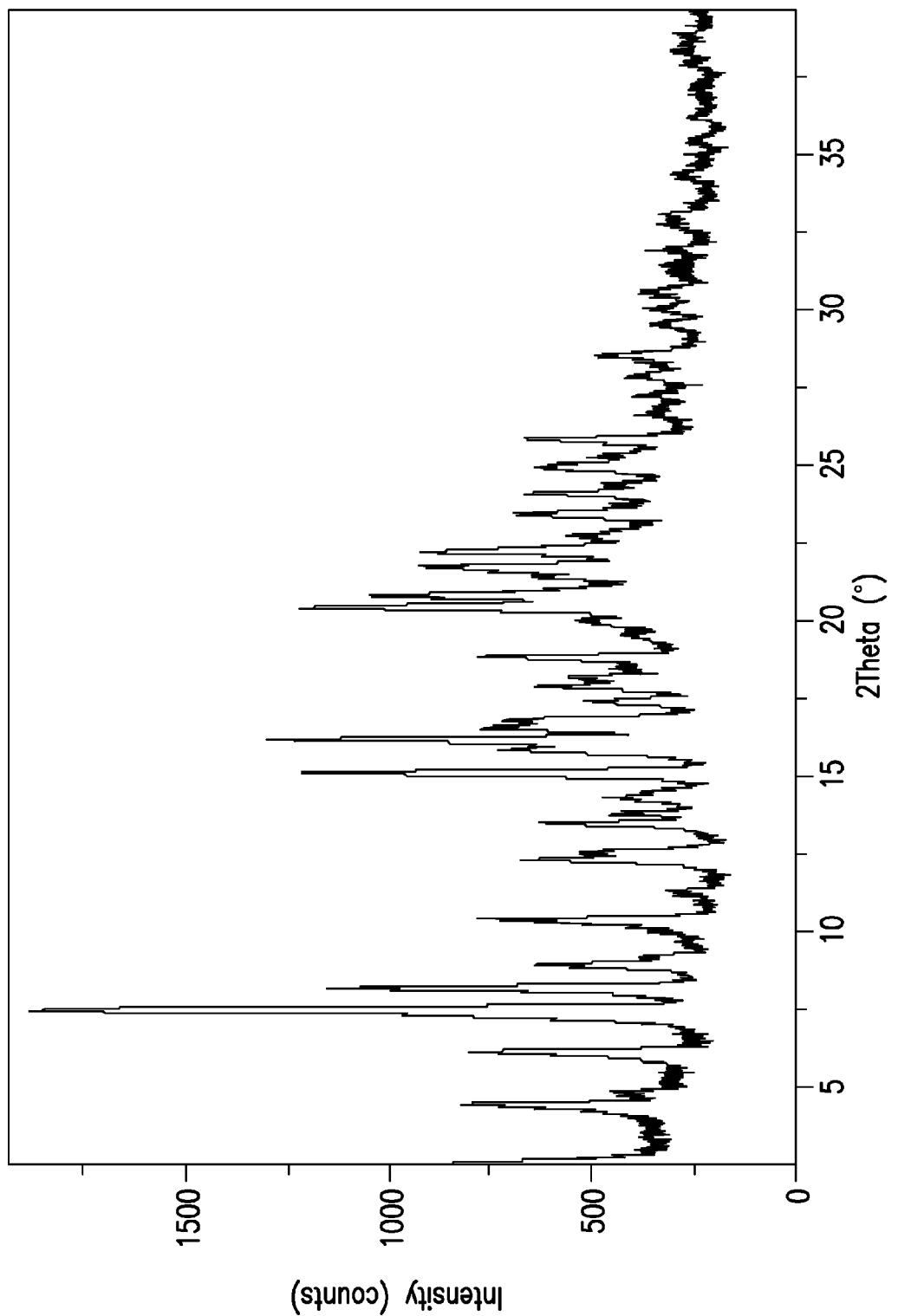
FIG. 2 is the XRPD pattern for ethanol solvate B of a potassium salt of exemplary Compound III-205.

Ethanol solvate B was be obtained by crystallization of the potassium salt of exemplary Compound III-205 in ethanol/water (10 ml/1 ml) at 40° C. or lower. It is only stable in contact with the solvent; the XRPD pattern was obtained using wet cake. FIG. 2 is the XRPD pattern for ethanol solvate B of the potassium salt of exemplary Compound III-205, with selected d-spacings listed in Table 2.

TABLE 2

X-ray powder diffraction: ethanol solvate B of the potassium salt of exemplary Compound III-205

| 2θ(2 theta)(degrees) | d-spacing (Å) |
|---|---|
| 4.5 | 19.8 |
| 6.1 | 14.4 |
| 7.4 | 11.9 |
| 8.2 | 10.8 |
| 10.4 | 8.48 |
| 15.1 | 5.85 |
| 16.2 | 5.47 |
| 18.9 | 4.70 |
| 20.8 | 4.27 |

Hydrate A4 of Exemplary Compound III-205 Potassium Salt

Figure 3:
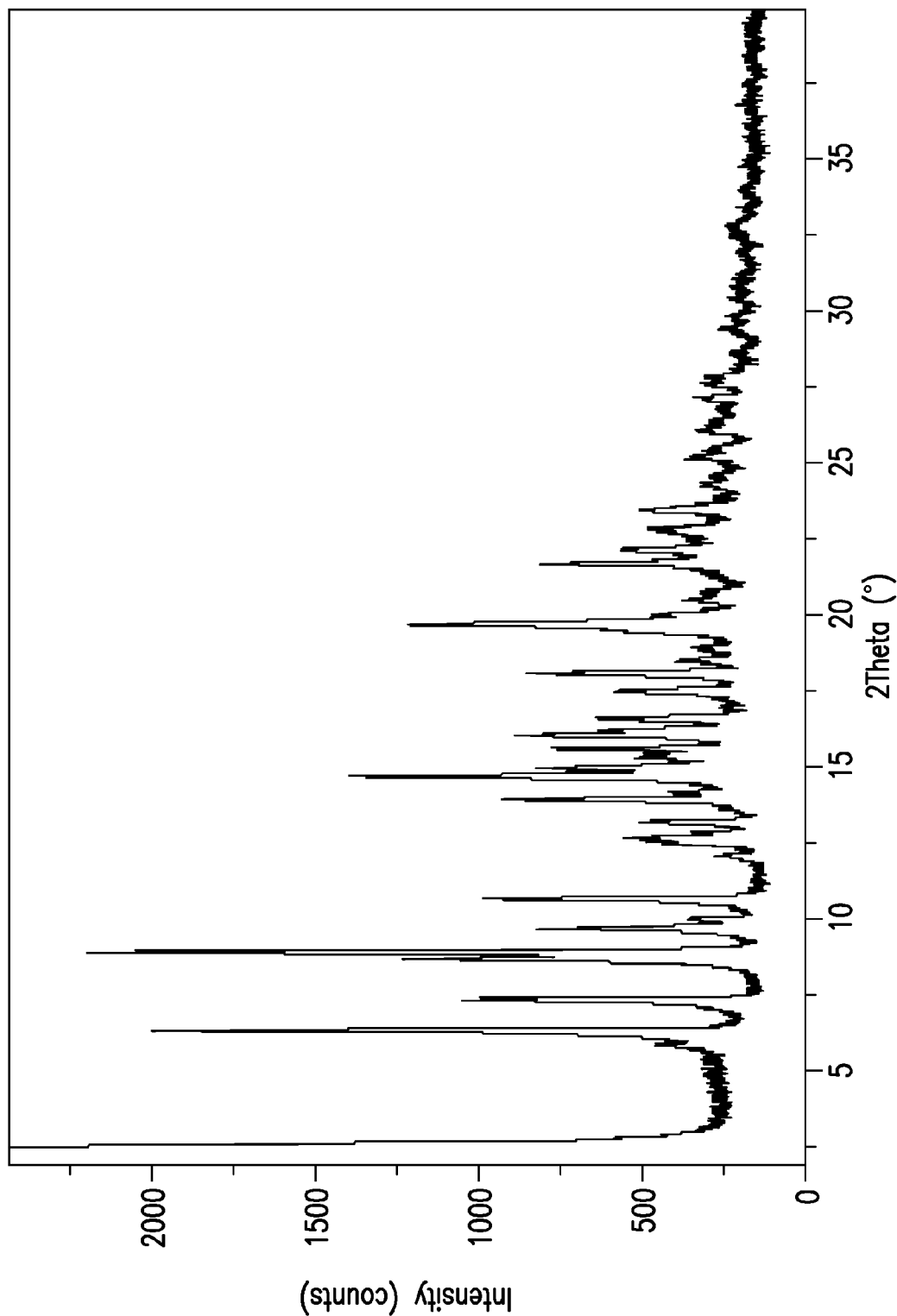
FIG. 3 is the XRPD pattern for the hydrate A4 of a potassium salt of exemplary Compound III-205.

Hydrate A4 of the potassium salt of exemplary Compound III-205 was obtained by drying ethanol solvate A at RT with flowing air or $N_2$ with RH between 10 and 60%. FIG. 3 is the XRPD pattern for the hydrate A4 of the potassium salt of exemplary Compound III-205 with selected d-spacings listed in Table 3.

TABLE 3

X-ray powder diffraction: Hydrate A4 of the
potassium salt of exemplary Compound III-205

| 2θ(2 theta)(degrees) | d-spacing (Å) |
|---|---|
| 6.3 | 14.1 |
| 7.3 | 12.1 |
| 8.9 | 10.0 |
| 9.7 | 9.2 |
| 10.6 | 8.33 |
| 13.9 | 6.38 |
| 14.6 | 6.05 |
| 16.0 | 5.55 |
| 18.0 | 4.93 |
| 19.6 | 4.53 |

Figure 4:
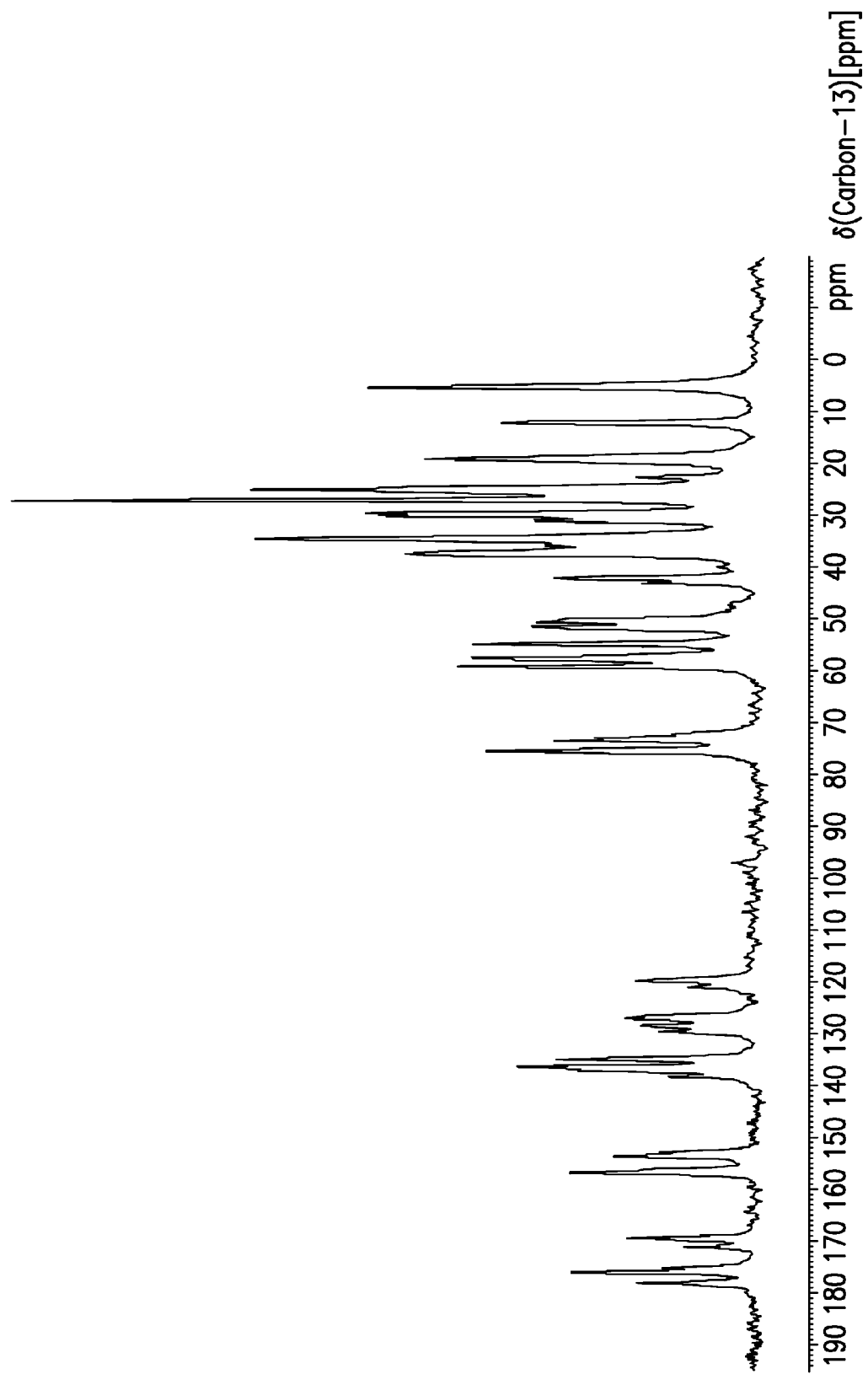
FIG. 4 is the solid-state carbon-13 CPMAS NMR spectrum of hydrate A4 of a potassium salt of exemplary Compound III-205.

FIG. 4 is the solid-state carbon-13 CPMAS NMR spectrum of hydrate A4 of the potassium salt of exemplary Compound III-205. Characteristic peaks for hydrate A4 are observed at 5.3, 24.4, 24.9, 29.4, 29.9, 51.4, 54.8, 134.9, and 178.2 ppm.

Hydrate A2 of Exemplary Compound III-205 Potassium Salt

Figure 5:
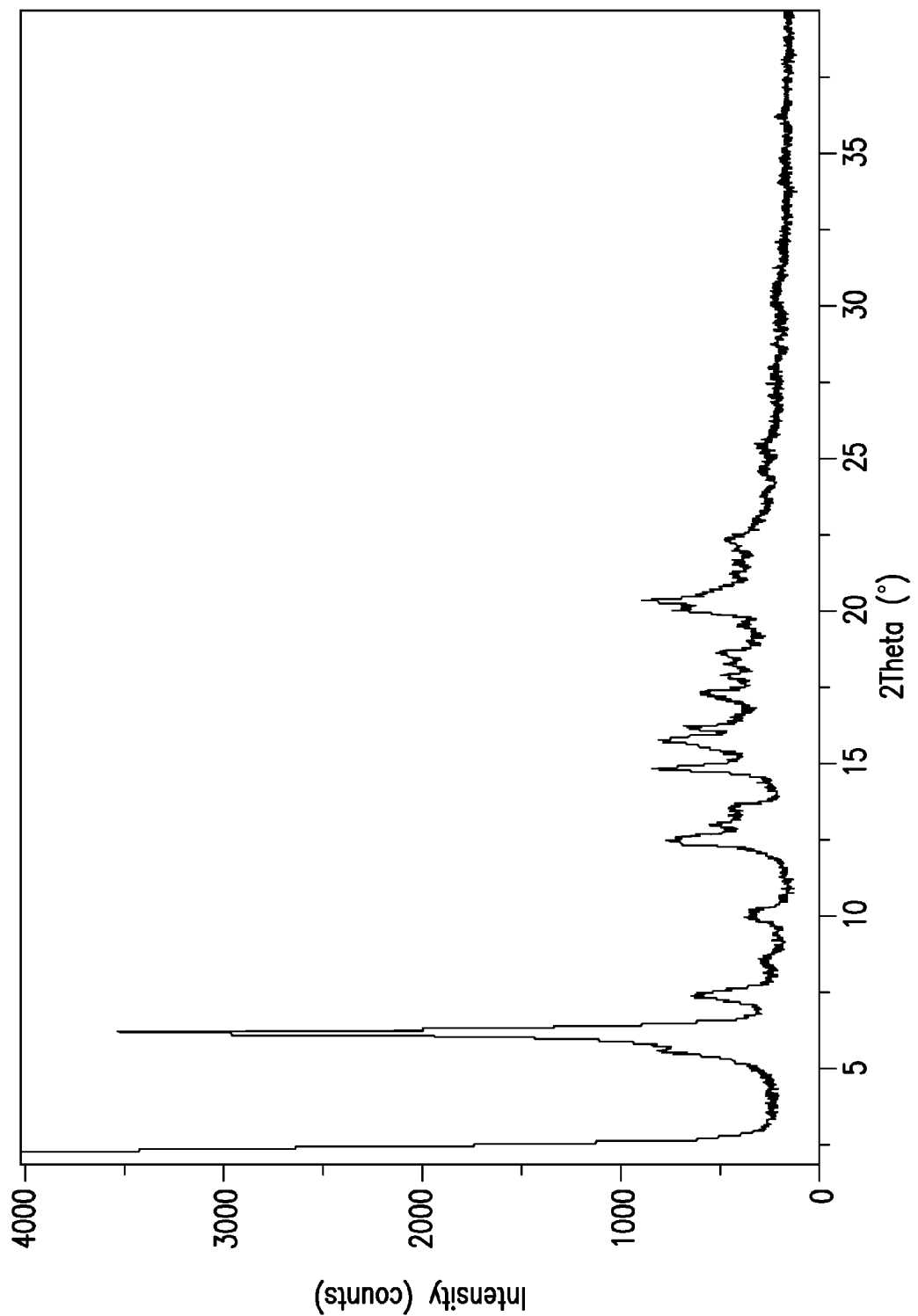
FIG. 5 is the XRPD pattern for hydrate A2 of a potassium salt of exemplary Compound III-205.

Hydrate A2 of the potassium salt of exemplary Compound III-205 was obtained by drying ethanol solvate A at 50° C. under vacuum with dry $N_2$ sweep and then exposed to air. FIG. 5 is the XRPD pattern for hydrate A2 of the potassium salt of exemplary Compound III-205 with selected d-spacings listed in Table 4.

TABLE 4

X-ray powder diffraction: Hydrate A2 of the
potassium salt of exemplary Compound III-205

| 2θ(2 theta)(degrees) | d-spacing (Å) |
|---|---|
| 6.2 | 14.3 |
| 7.4 | 12.0 |
| 12.4 | 7.12 |
| 14.8 | 5.98 |
| 17.3 | 5.11 |
| 20.4 | 4.36 |

Figure 6:
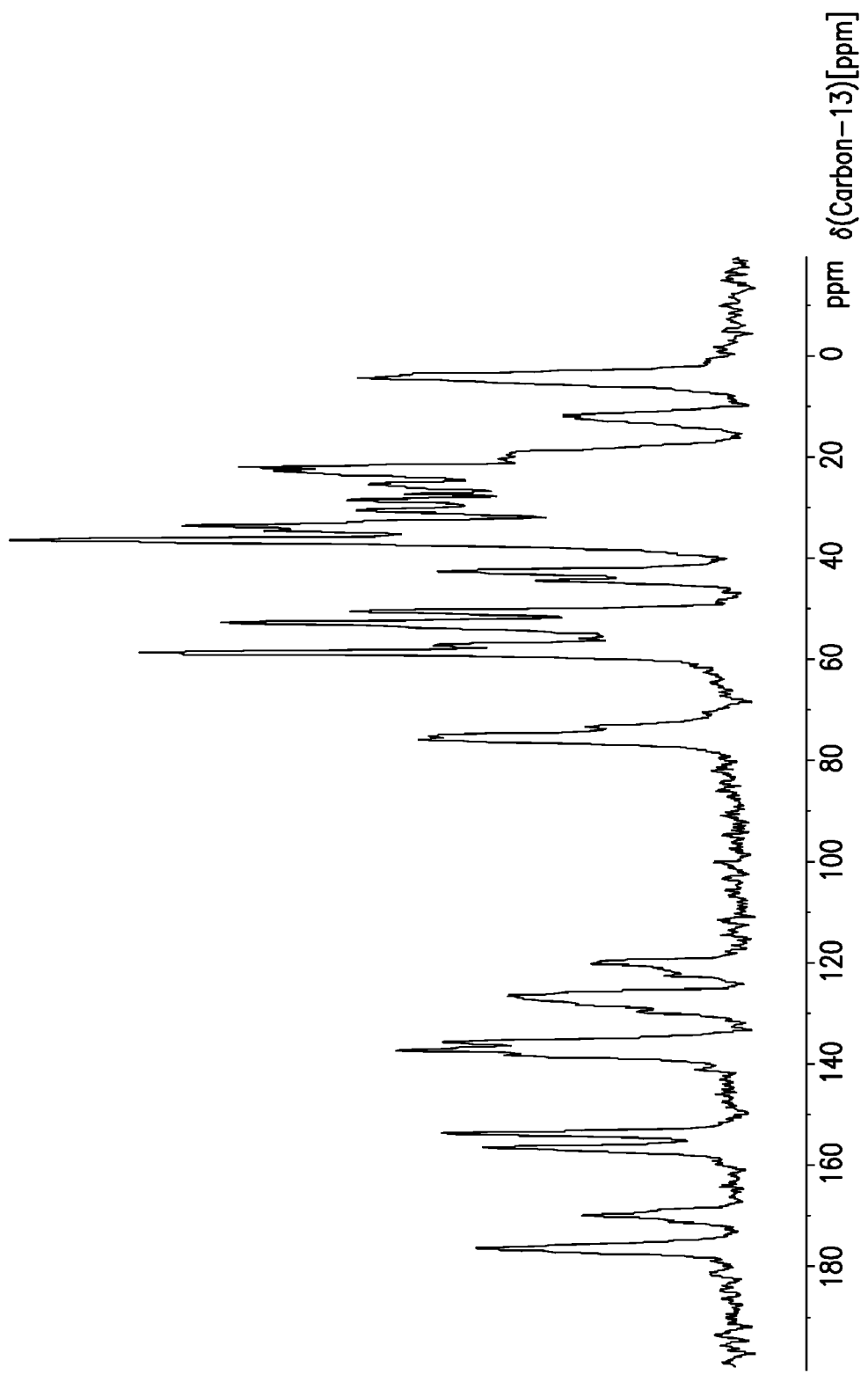
FIG. 6 is the solid-state carbon-13 CPMAS NMR spectrum of hydrate A2 of a potassium salt of exemplary Compound III-205.

FIG. 6 is the solid-state carbon-13 CPMAS NMR spectrum of hydrate A2 of the potassium salt of exemplary Compound III-205. Characteristic peaks for hydrate A2 are observed at 3.8, 4.5, 22.2, 23.0, 28.6, 33.8, 44.6, 53.0, 136.0, and 176.7 ppm.

Hydrate D of Exemplary Compound III-205 Potassium Salt

Figure 7:
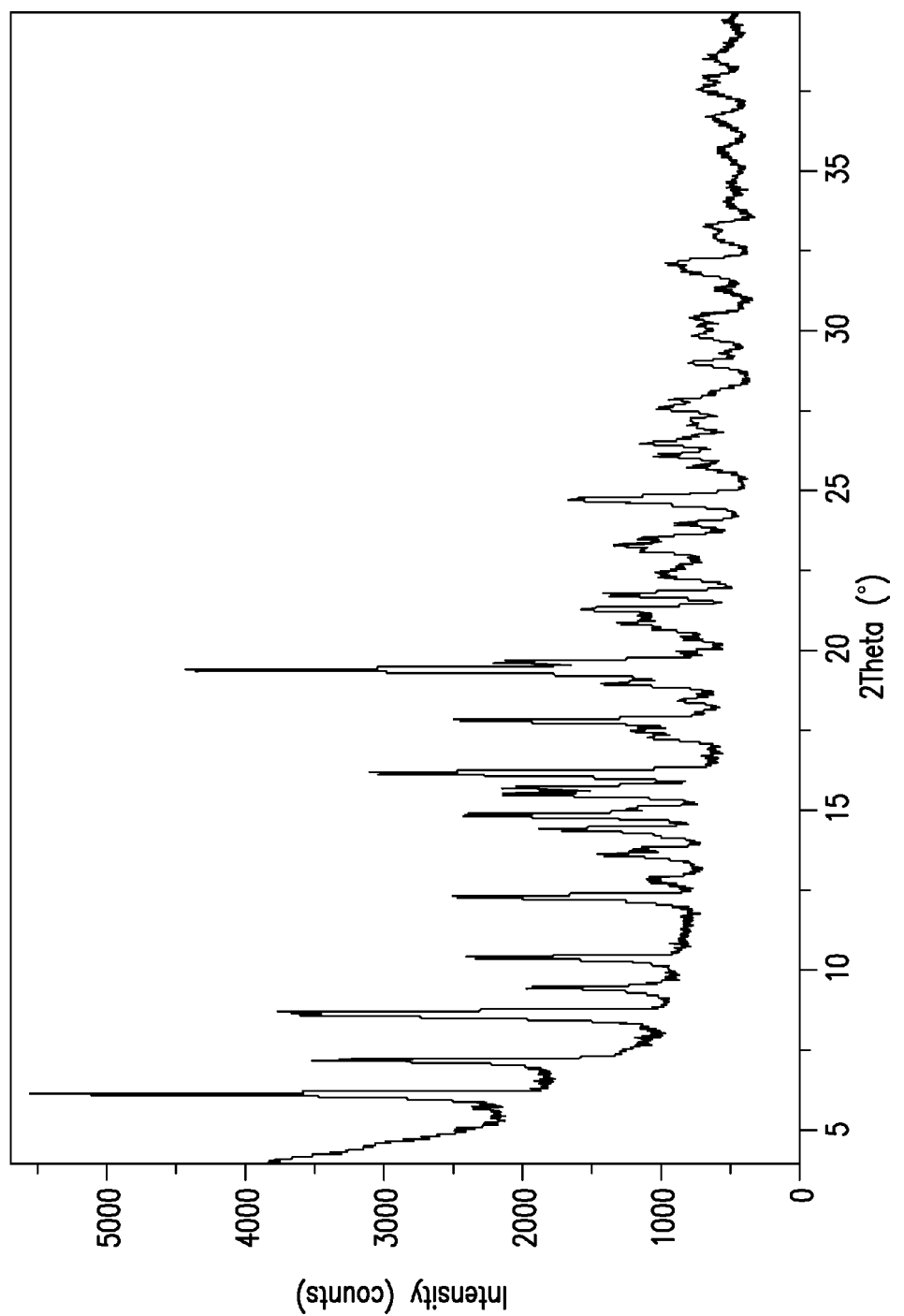
FIG. 7 is the XRPD pattern for hydrate D of a potassium salt of exemplary Compound III-205.

Hydrate D of the potassium salt of exemplary Compound III-205 was obtained by sweeping hydrate A4 with humid $N_2$, with RH higher than 60%, or by mixing hydrate A4 with water. FIG. 7 is the XRPD pattern for hydrate D of the potassium salt of exemplary Compound III-205 with selected d-spacings listed in Table 5.

TABLE 5

X-ray powder diffraction: Hydrate D of the
potassium salt of exemplary Compound III-205

| 2θ(2 theta)(degrees) | d-spacing (Å) |
|---|---|
| 6.1 | 14.4 |
| 7.2 | 12.3 |
| 8.7 | 10.2 |
| 10.4 | 8.49 |
| 12.3 | 7.18 |
| 14.9 | 5.96 |
| 16.2 | 5.48 |
| 17.8 | 4.99 |
| 19.4 | 4.58 |
| 24.7 | 3.61 |

Figure 8:
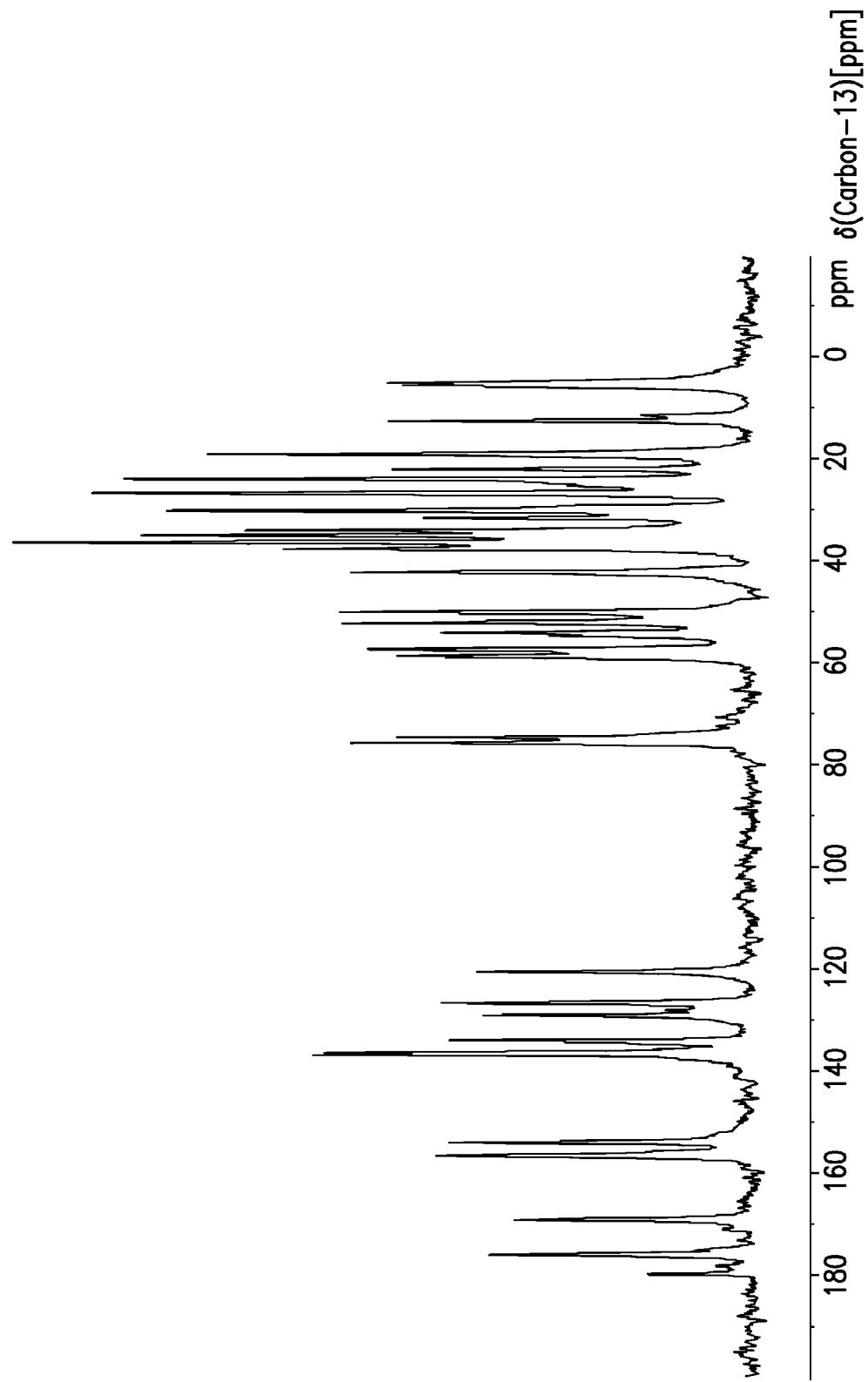
FIG. 8 is the solid-state carbon-13 CPMAS NMR spectrum of hydrate D of a potassium salt of exemplary Compound III-205.

FIG. 8 is the solid-state carbon-13 CPMAS NMR spectrum of hydrate D of the potassium salt of exemplary Compound III-205. Characteristic peaks for hydrate D are observed at 154.3, 156.9, 169.6, 176.4, and 180.0 ppm.

Hydrate F of Exemplary Compound III-205 Potassium Salt

Figure 9:
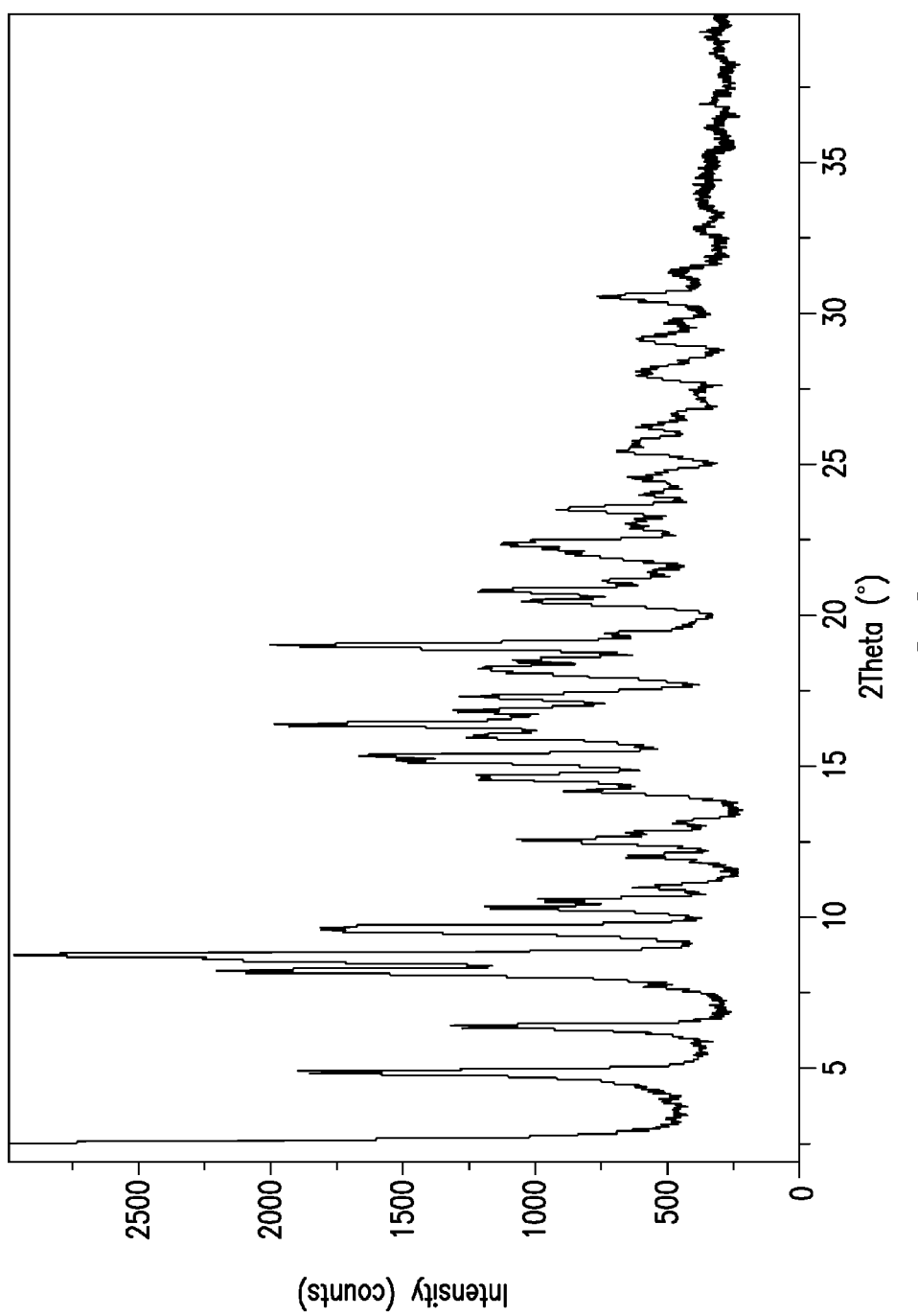
FIG. 9 is the XRPD pattern for hydrate F of a potassium salt of exemplary Compound III-205.

Hydrate F of the potassium salt of exemplary Compound III-205 was obtained by drying ethanol solvate B at RT with flowing air or $N_2$ with RH between 55 and 80%. FIG. 9 is the XRPD pattern for hydrate F of the potassium salt of exemplary Compound III-205, with selected d-spacings listed in Table 6.

TABLE 6

X-ray powder diffraction: Hydrate F of the
potassium salt of exemplary Compound III-205

| 2θ(2 theta)(degrees) | d-spacing (Å) |
|---|---|
| 4.7 | 18.8 |
| 6.3 | 14.1 |
| 8.1 | 10.9 |
| 8.6 | 10.2 |
| 12.4 | 7.13 |
| 15.2 | 5.82 |
| 16.3 | 5.45 |
| 17.2 | 5.16 |
| 18.9 | 4.71 |
| 23.4 | 3.81 |

Figure 10:
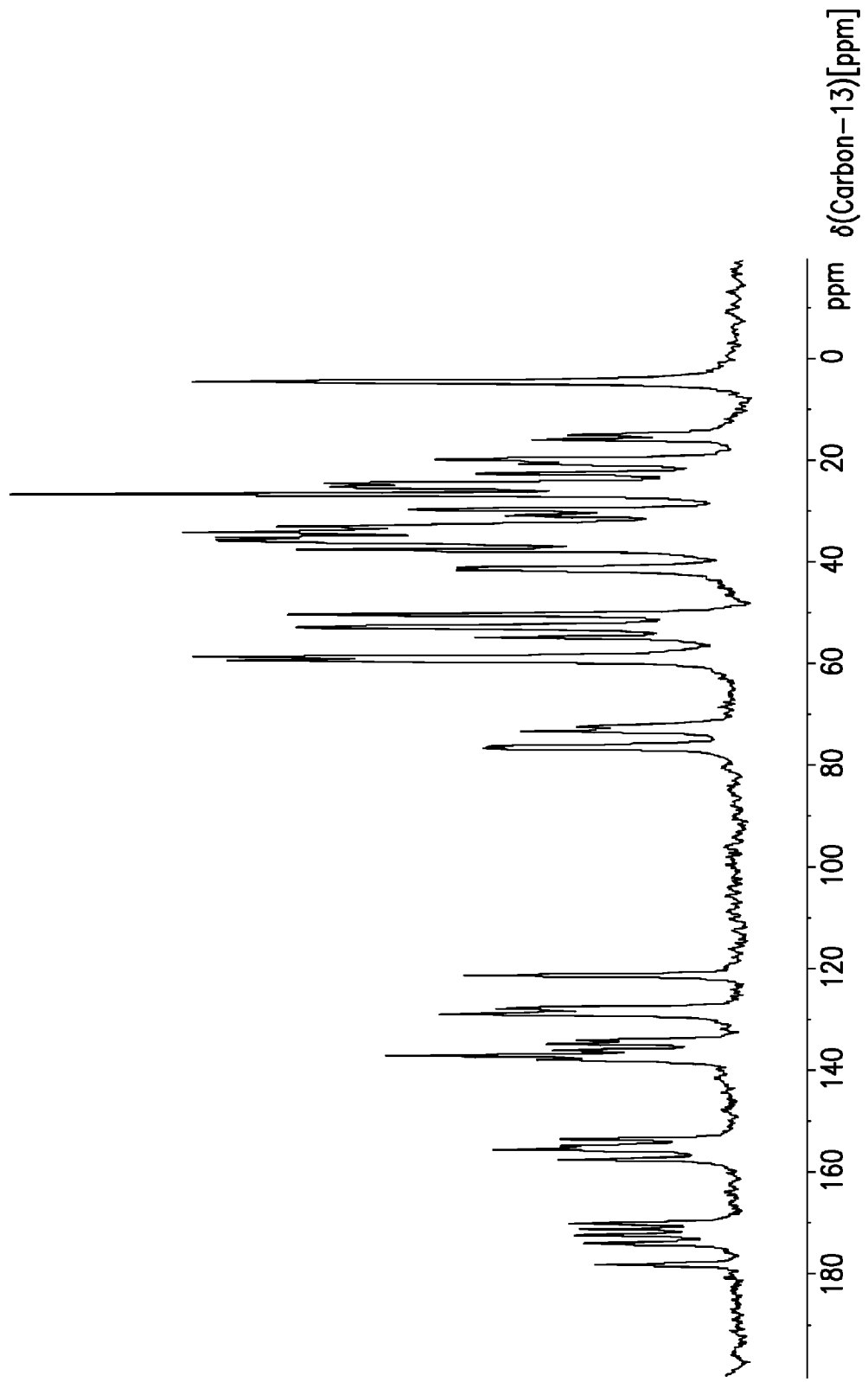
FIG. 10 is the solid-state carbon-13 CPMAS NMR spectrum of hydrate F of a potassium salt of exemplary Compound III-205.

FIG. 10 is the solid-state carbon-13 CPMAS NMR spectrum of hydrate F of the potassium salt of exemplary Compound III-205. Characteristic peaks for hydrate F are observed at 153.7, 155.1, 155.8, 157.7, 170.3, 171.5, 172.7, 174.3, and 178.4 ppm.

Hydrate G of Exemplary Compound III-205 Potassium Salt

Figure 11:
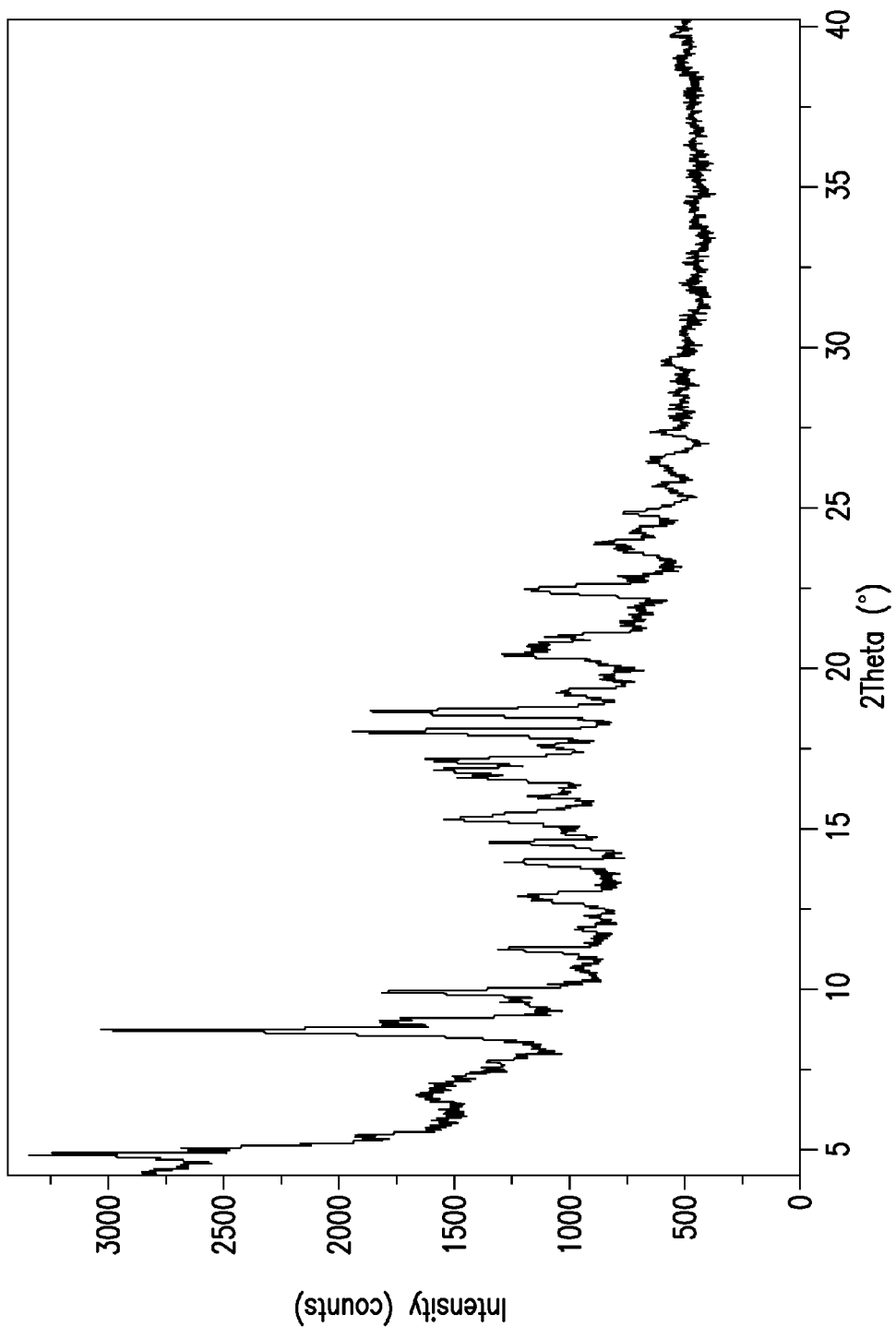
FIG. 11 is the XRPD pattern for hydrate G of a potassium salt of exemplary Compound III-205.

Hydrate G of the potassium salt of exemplary Compound III-205 was obtained by drying ethanol solvate B or hydrate F at RT with flowing $N_2$ with RH below 20%. The XRPD pattern of hydrate G was obtained at RH less than 20%. FIG. 11 is the XRPD pattern for hydrate G of the potassium salt of exemplary Compound III-205, with selected d-spacings listed in Table 7.

TABLE 7

X-ray powder diffraction: Hydrate G of the
potassium salt of exemplary Compound III-205

| 2θ(2 theta)(degrees) | d-spacing (Å) |
|---|---|
| 8.7 | 10.2 |
| 9.9 | 8.94 |
| 11.2 | 7.88 |
| 12.9 | 6.87 |
| 13.9 | 6.36 |
| 14.5 | 6.10 |
| 18.0 | 4.94 |
| 18.6 | 4.77 |
| 22.4 | 3.97 |

Example 7

The X-ray powder diffraction (XRPD) patterns for the solid phases of exemplary Compound III-205 were generated as described above in Example 7.

The solid-state carbon-13 nuclear magnetic resonance (NMR) spectra were collected on a BRUKER AV500 NMR spectrometer using a BRUKER 4 mm double resonance CPMAS probe. All spectra were collected utilizing proton/carbon-13 variable-amplitude cross-polarization (VACP) with a contact time of 2 ms, and a pulse delay of 2 s, while magic-angle spinning (MAS) the samples at 10 kHz. A line broadening of 10 Hz was applied to the carbon-13 spectra before Fourier Transformation. Chemical shifts are reported on the TMS scale using the carbonyl carbon of glycine (176.03 ppm.) as a secondary reference.

Ethyl Acetate Solvate of Exemplary Compound III-205

Figure 12:
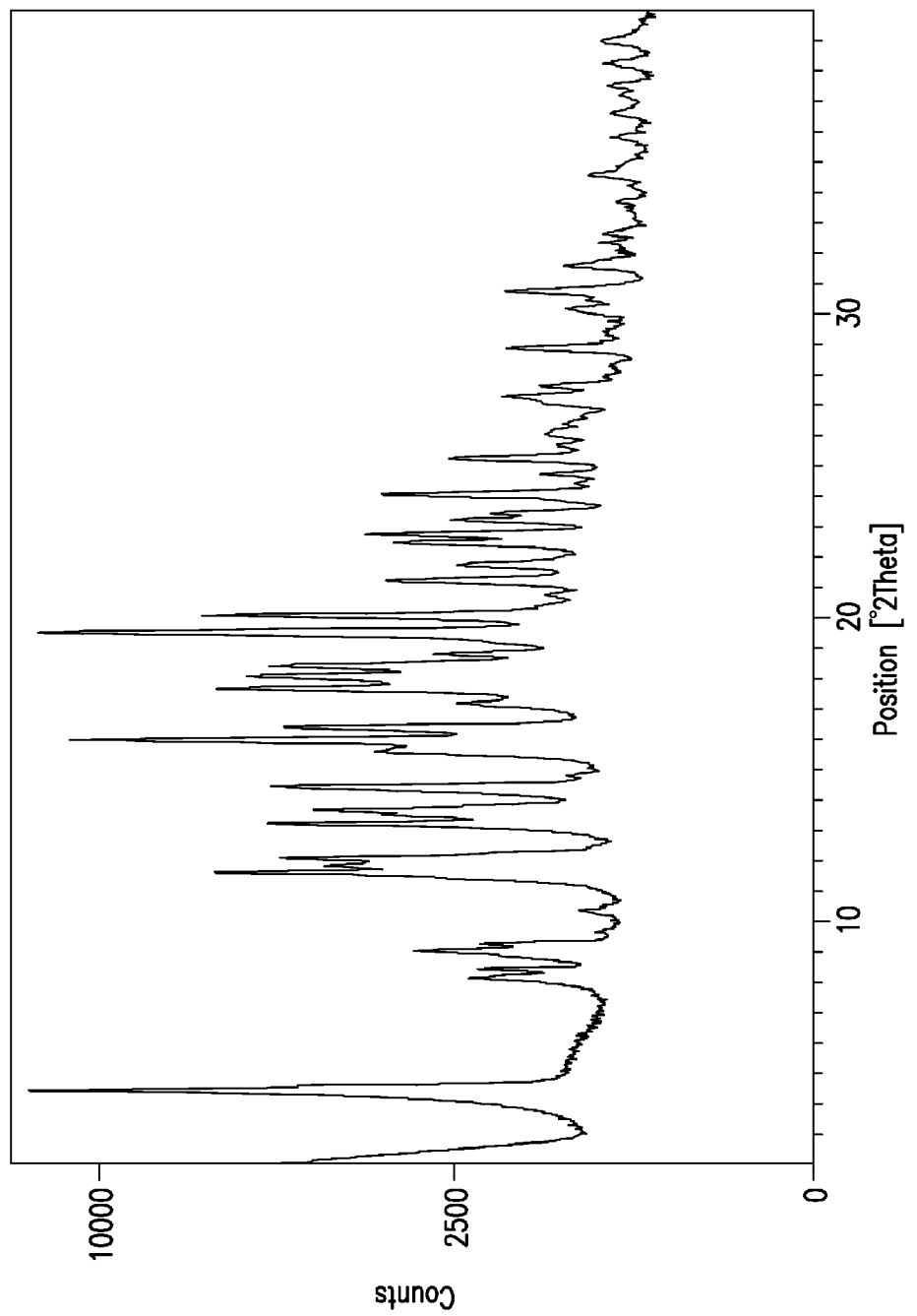
FIG. 12 is the XRPD pattern for a crystalline ethyl acetate solvate of exemplary Compound III-205.

The crystalline ethyl acetate solvate of exemplary Compound III-205 is a co-solvate with water. The ethyl acetate solvate was prepared from a crystallization performed in ethyl acetate and isopropyl acetate. FIG. 12 is the XRPD pattern for the crystalline ethyl acetate solvate of exemplary Compound III-205 with selected d-spacings listed in Table 8.

TABLE 8

X-ray powder diffraction: crystalline ethyl acetate solvate of exemplary Compound III-205

| 2θ(2 theta)(degrees) | d-spacing (Å) |
|---|---|
| 4.4 | 20.04 |
| 11.6 | 7.61 |
| 11.8 | 7.49 |
| 13.2 | 6.69 |
| 13.7 | 6.47 |
| 14.5 | 6.11 |
| 16.0 | 5.55 |
| 16.4 | 5.40 |
| 17.7 | 5.02 |
| 18.4 | 4.82 |

Figure 13:
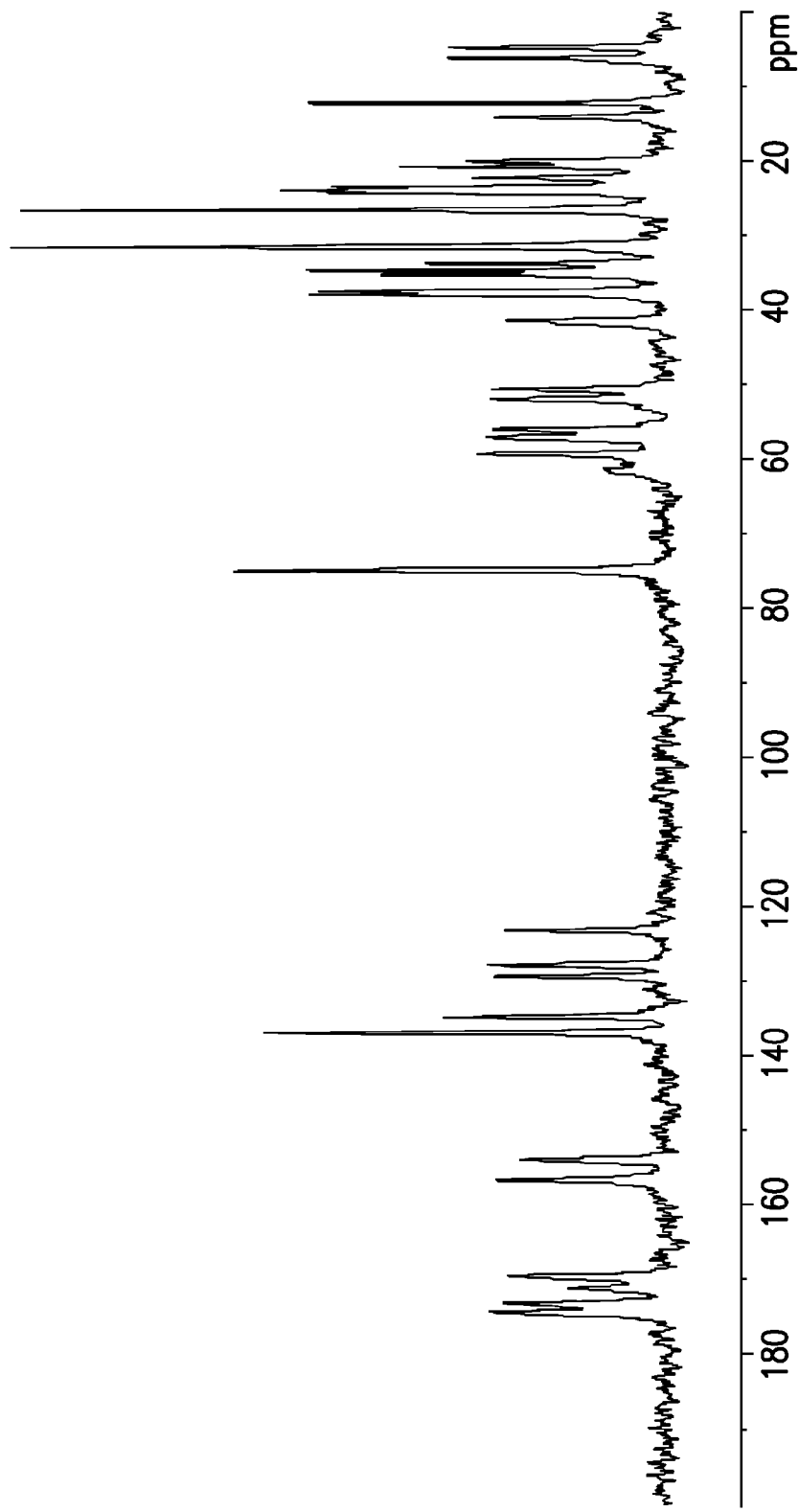
FIG. 13 is the solid-state carbon-13 CPMAS NMR spectrum of a crystalline ethyl acetate solvate of exemplary Compound III-205.

FIG. 13 is the solid-state carbon-13 CPMAS NMR spectrum of the crystalline ethyl acetate solvate of exemplary Compound III-205. Characteristic peaks for the ethyl acetate solvate are observed at 4.7, 6.2, 12.1, 23.8, 34.6, 37.8, 56.9, 74.9, 134.6 and 136.8 ppm.

Hydrate of Exemplary Compound III-205

Figure 14:
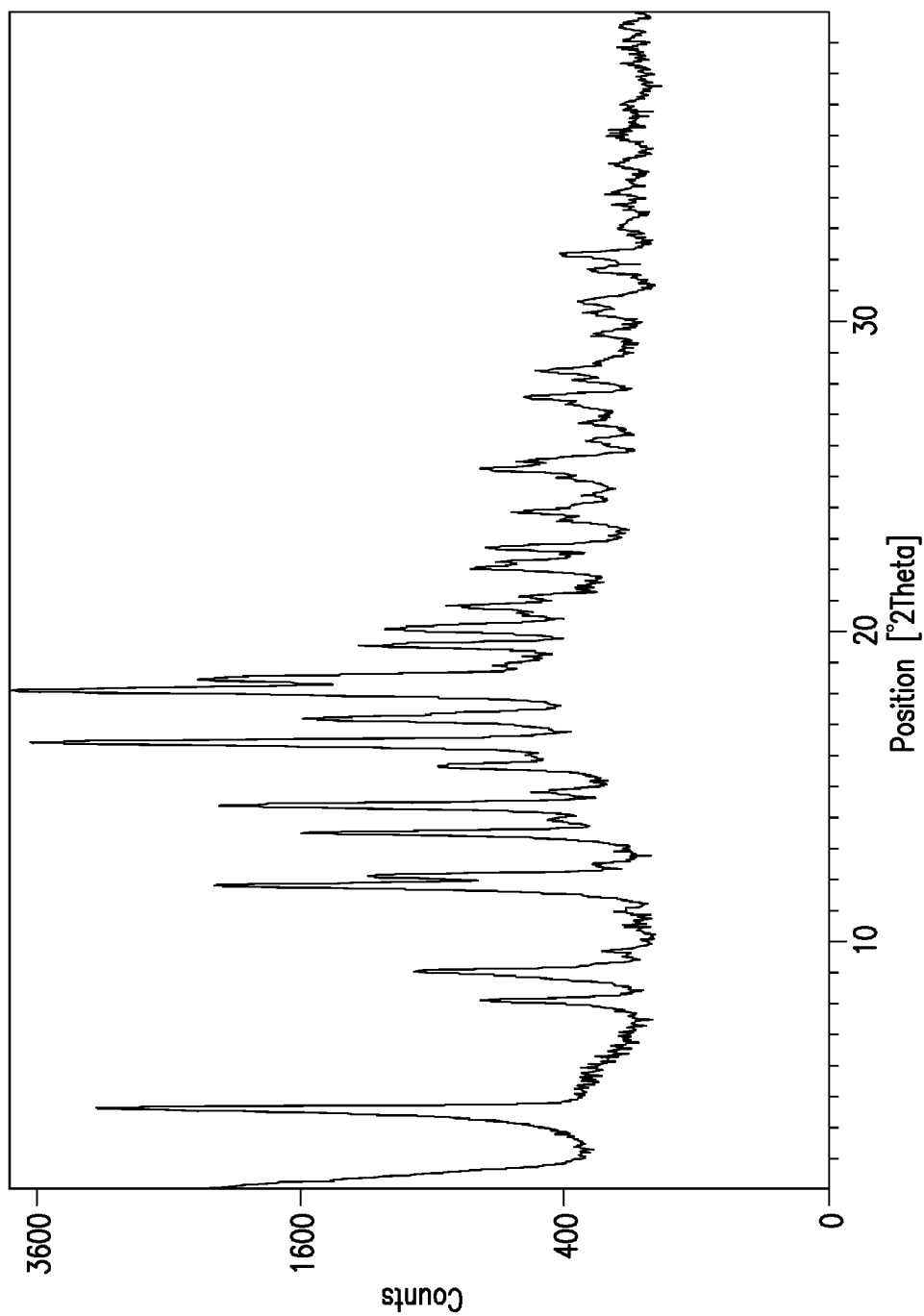
FIG. 14 is the XRPD pattern for a crystalline hydrate of exemplary Compound III-205.

The crystalline hydrate of exemplary Compound III-205 was prepared from a crystallization performed in ethyl acetate and isopropyl acetate. An ethyl acetate solvate was formed during crystallization, and upon drying, the ethyl acetate was removed from the crystal, leaving the hydrate form. FIG. 14 is the XRPD pattern for the crystalline hydrate of exemplary Compound III-205 with selected d-spacings listed in Table 9.

TABLE 9

X-ray powder diffraction: crystalline hydrate of exemplary Compound III-205

| 2θ(2 theta)(degrees) | d-spacing (Å) |
|---|---|
| 9.1 | 9.73 |
| 11.8 | 7.49 |
| 12.2 | 7.28 |
| 14.4 | 6.13 |
| 16.5 | 5.39 |
| 18.1 | 4.89 |
| 18.5 | 4.81 |
| 18.6 | 4.78 |
| 22.0 | 4.04 |
| 22.7 | 3.91 |

Figure 15:
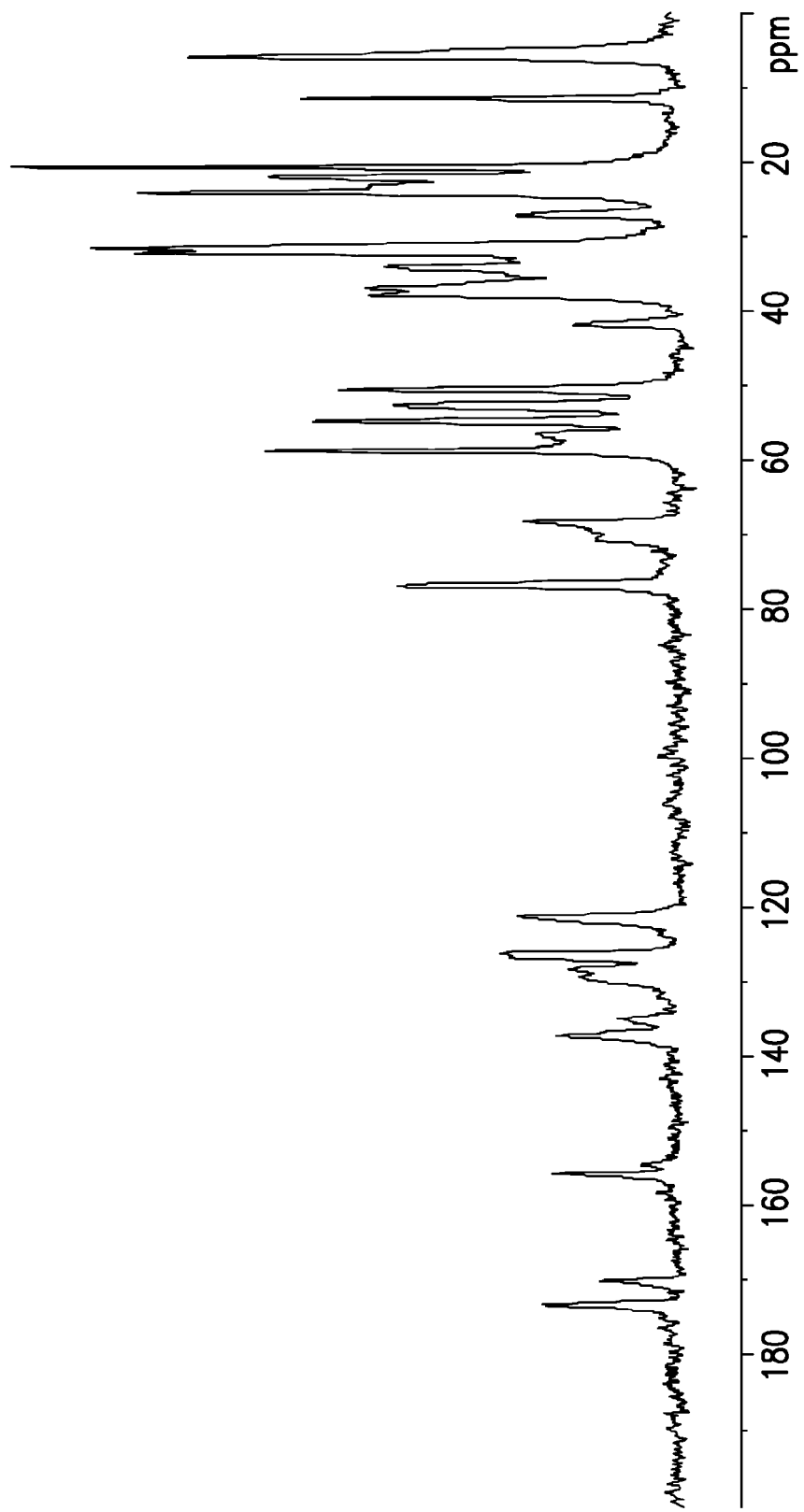
FIG. 15 is the solid-state carbon-13 CPMAS NMR spectrum of a crystalline hydrate of exemplary Compound III-205.

FIG. 15 is the solid-state carbon-13 CPMAS NMR spectrum of the crystalline hydrate of exemplary Compound III-205. Characteristic peaks for the hydrate are observed at 6.1, 11.5, 22.1, 24.3, 32.2, 36.9, 54.7, 68.2, 76.9 and 121.1 ppm.

Heptane Solvate of Exemplary Compound III-205

Figure 16:
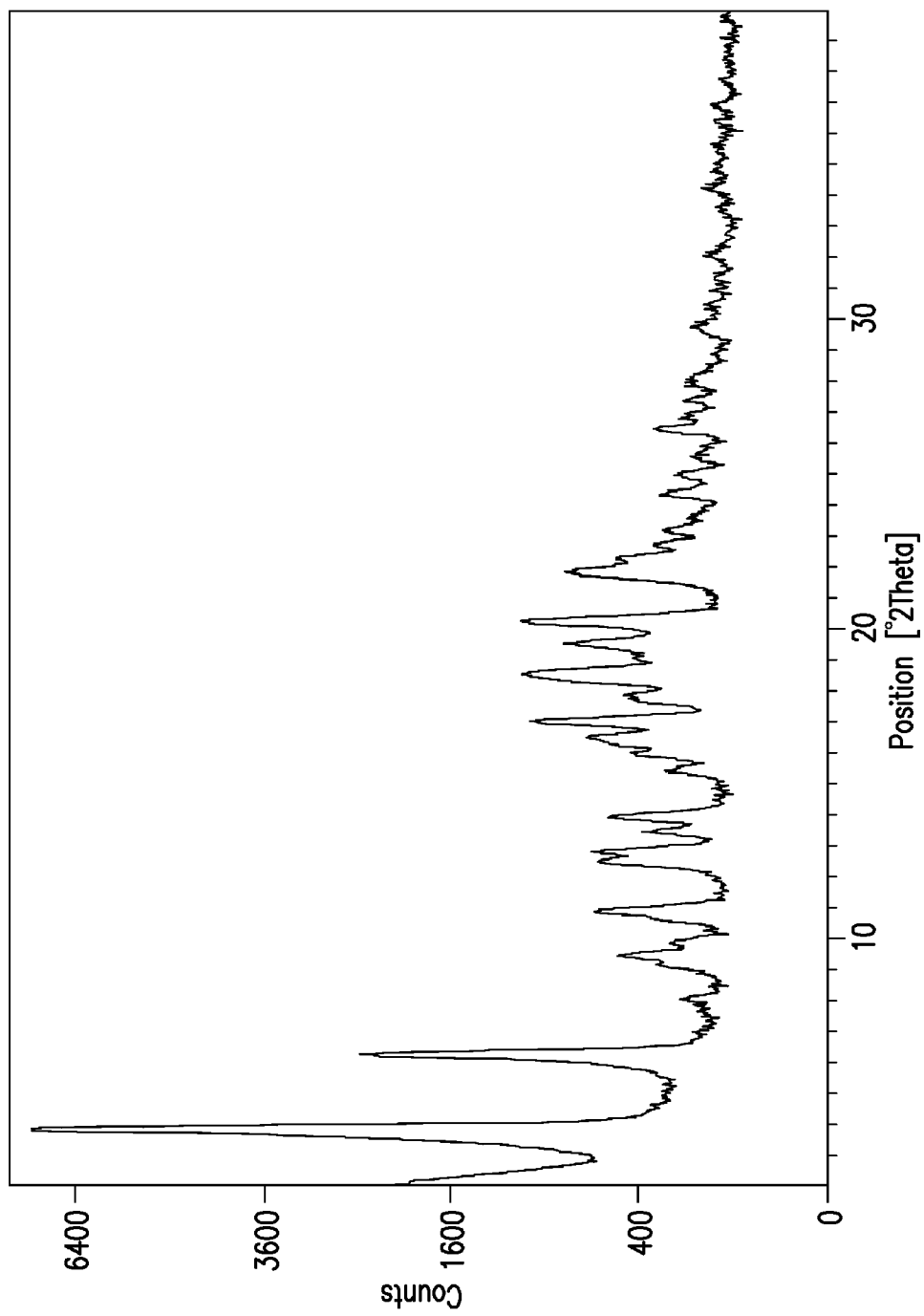
FIG. 16 is the XRPD pattern for a crystalline heptane solvate of exemplary Compound III-205.

The crystalline heptane solvate of exemplary Compound III-205 was prepared from a crystallization performed in heptane and isopropyl acetate. A heptane solvate was formed during crystallization, and upon drying, the heptane was removed from the crystal, leaving the anhydrate form. FIG. 16 is the XRPD pattern for the crystalline heptane solvate of exemplary Compound III-205 with selected d-spacings listed in Table 10.

TABLE 10

X-ray powder diffraction: crystalline heptane solvate of exemplary Compound III-205

| 2θ(2 theta)(degrees) | d-spacing (Å) |
|---|---|
| 10.9 | 8.11 |
| 12.5 | 7.09 |
| 15.9 | 5.56 |
| 16.5 | 5.36 |
| 17.0 | 5.23 |
| 18.3 | 4.84 |
| 19.5 | 4.55 |
| 20.3 | 4.38 |
| 21.9 | 4.06 |
| 22.3 | 3.99 |

Figure 17:
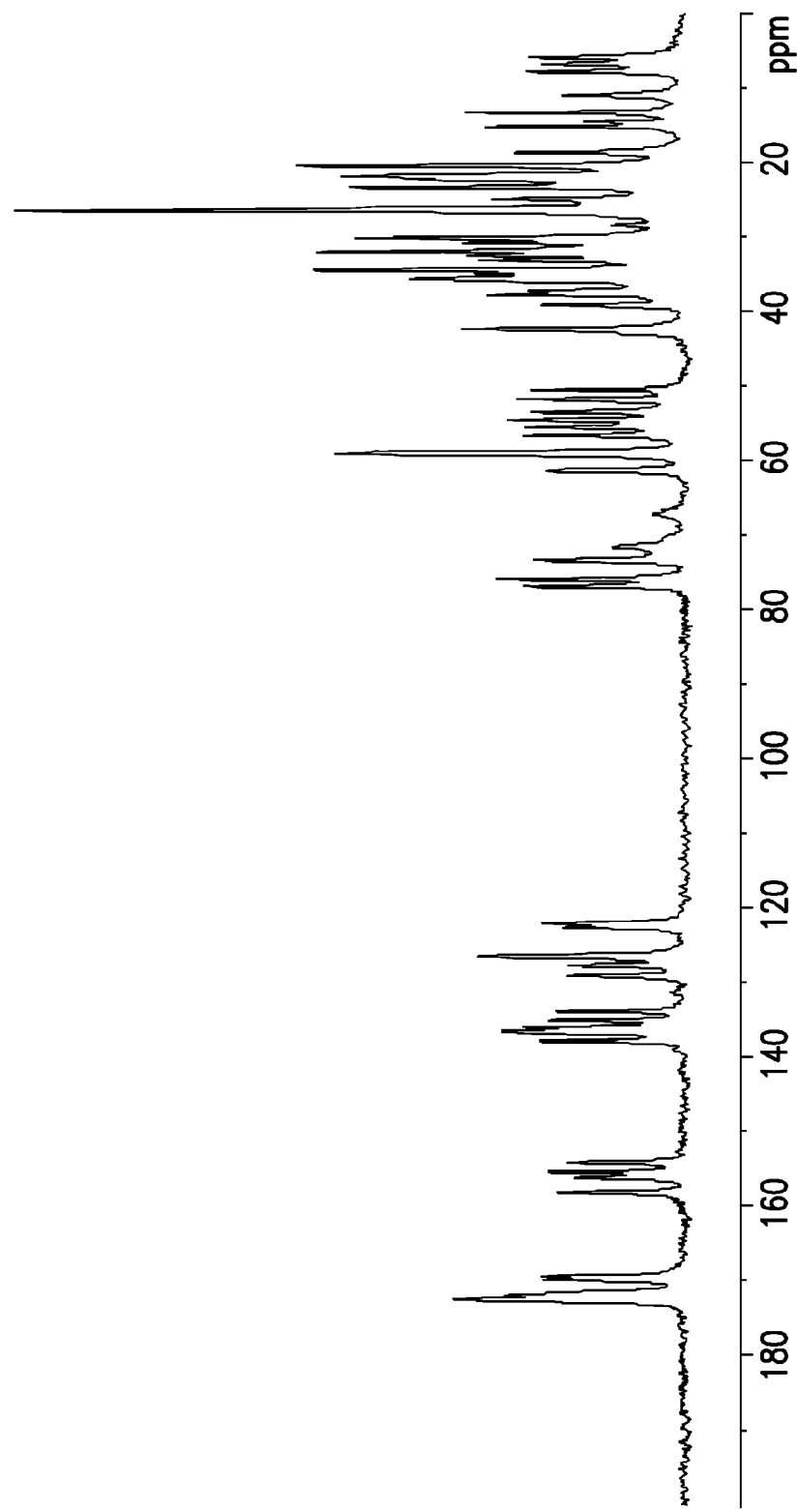
FIG. 17 is the solid-state carbon-13 CPMAS NMR spectrum of a crystalline heptane solvate of exemplary Compound III-205.

FIG. 17 is the solid-state carbon-13 CPMAS NMR spectrum of the crystalline heptane solvate of exemplary Compound III-205. Characteristic peaks for the heptane solvate are observed at 13.2, 15.2, 20.5, 31.9, 35.7, 42.3, 59.0, 76.0, 126.4 and 172.6 ppm.

Anhydrate of Exemplary Compound III-205

Figure 18:
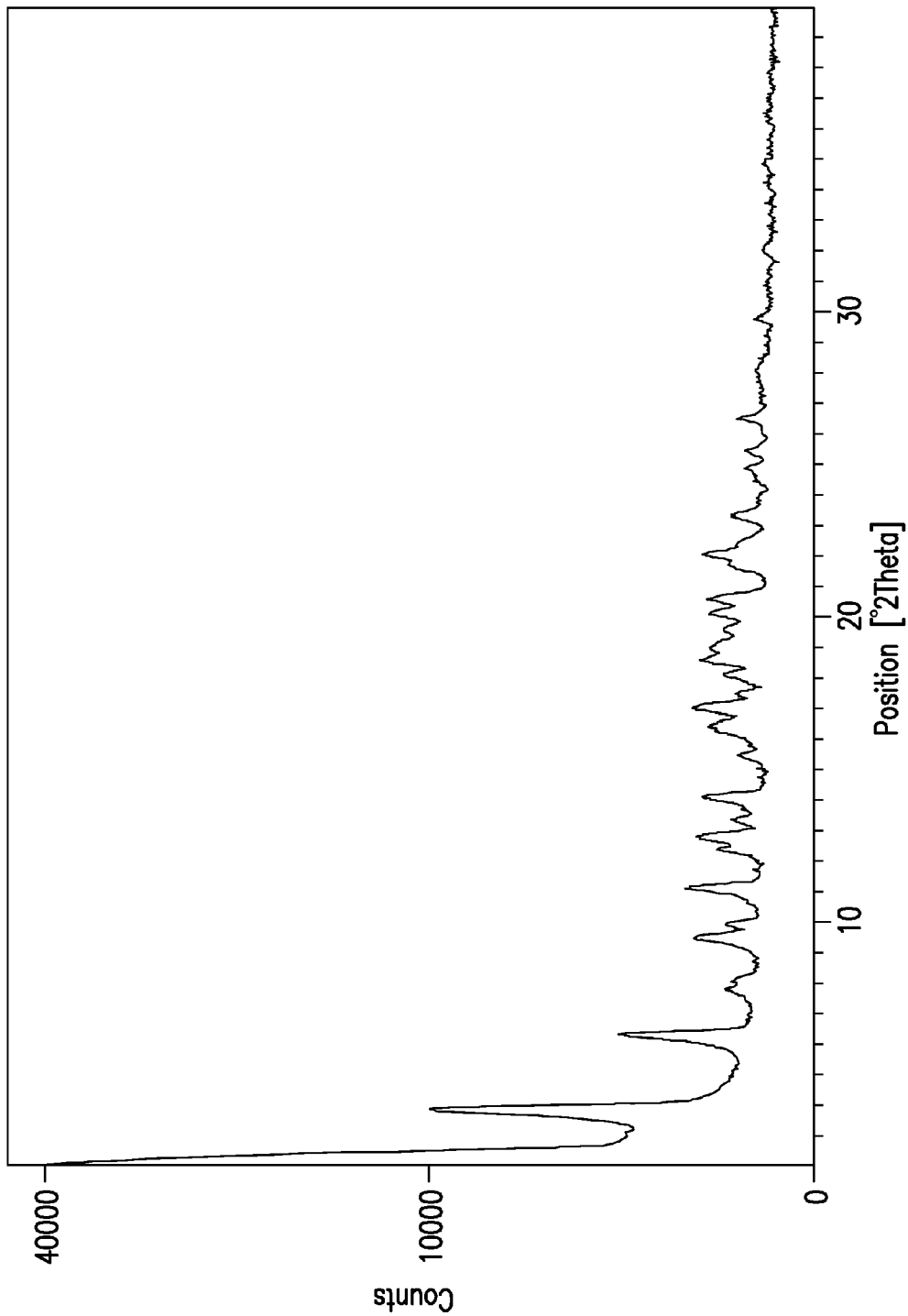
FIG. 18 is the XRPD pattern for a crystalline anhydrate of exemplary Compound III-205.

The crystalline anhydrate of exemplary Compound III-205 was prepared from a crystallization performed in heptane and isopropyl acetate. A heptane solvate was formed during crystallization, and upon drying, the heptane was removed from the crystal, leaving the anhydrate form. FIG. 18 is the XRPD pattern for the crystalline anhydrate of exemplary Compound III-205 with selected d-spacings listed in Table 11.

TABLE 11

X-ray powder diffraction: crystalline anhydrate of exemplary Compound III-205

| 2θ(2 theta)(degrees) | d-spacing (Å) |
|---|---|
| 2.4 | 36.59 |
| 3.9 | 22.72 |
| 11.2 | 7.93 |
| 14.2 | 6.25 |
| 16.4 | 5.39 |
| 17.2 | 5.17 |
| 19.1 | 4.65 |
| 20.1 | 4.41 |
| 20.6 | 4.31 |
| 22.1 | 4.03 |

Figure 19:
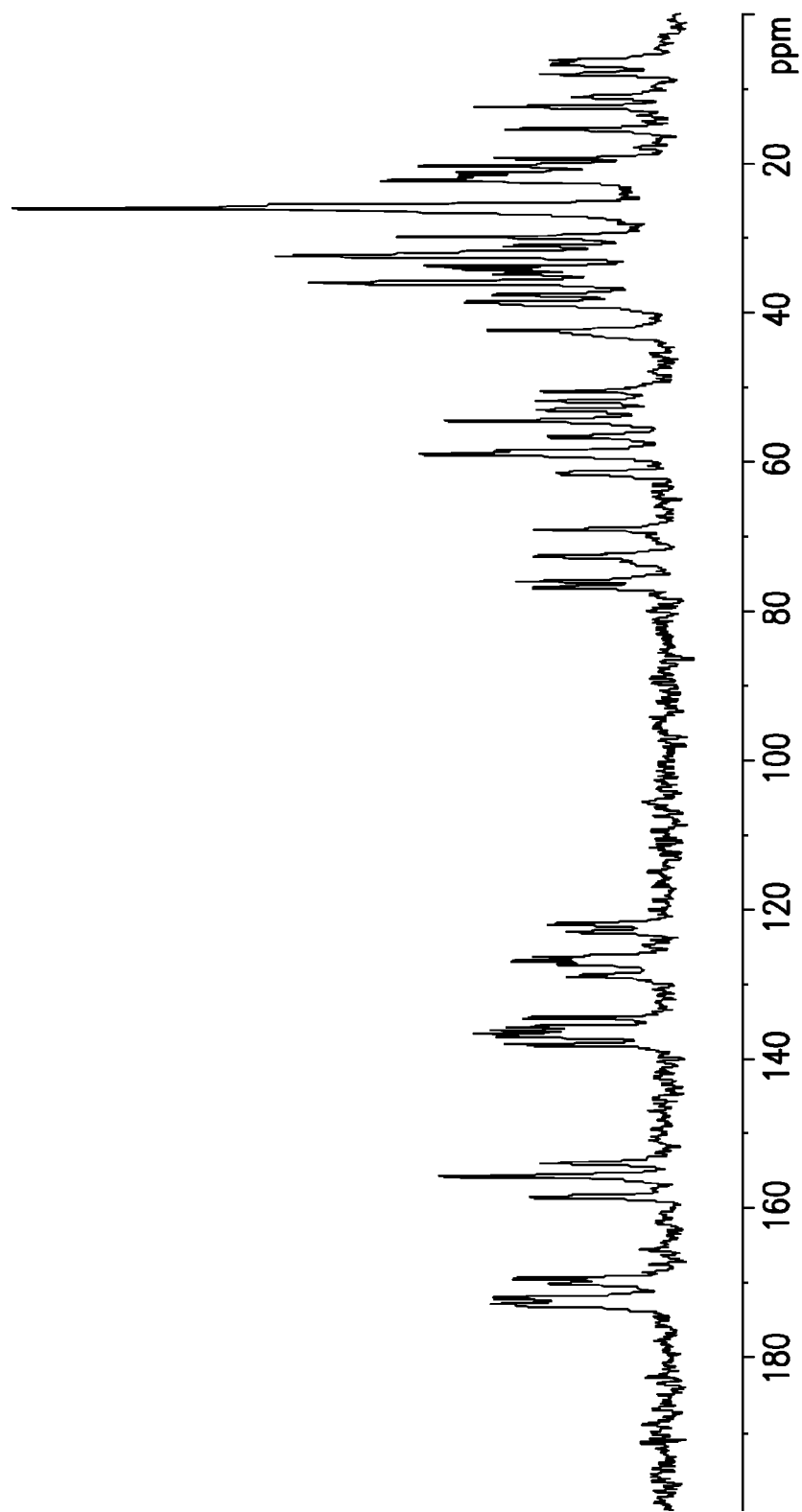
FIG. 19 is the solid-state carbon-13 CPMAS NMR spectrum of a crystalline anhydrate of exemplary Compound III-205.

FIG. 19 is the solid-state carbon-13 CPMAS NMR spectrum of the crystalline anhydrate of exemplary Compound III-205. Characteristic peaks for the anhydrate are observed at 19.4, 26.0, 29.8, 33.7, 34.7, 37.6, 135.9, 155.5, 171.7 and 172.5 ppm.

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A process for preparing compounds of Formula I,

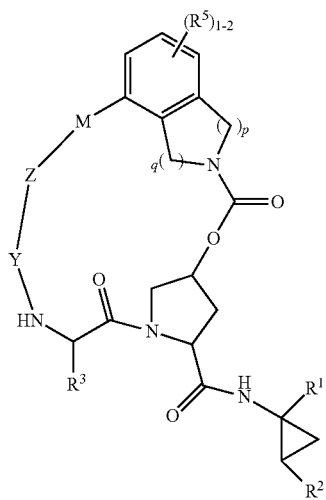

or pharmaceutically acceptable salts, solvates or hydrates thereof, wherein:

p and q are independently 1 or 2;

$R^1$ is $CO_2R^{10}$, $CONR^{10}SO_2R^6$, $CONR^{10}SO_2NR^8R^9$, or tetrazolyl;

$R^2$ is $C_1$-$C_6$ alkyl, $C_2$-$C_6$ alkenyl or $C_3$-$C_8$ cycloalkyl, wherein said alkyl, alkenyl or cycloalkyl is substituted with from 0 to 3 halo;

$R^3$ is $C_1$-$C_8$ alkyl, $C_3$-$C_8$ cycloalkyl, $C_3$-$C_8$ cycloalkyl($C_1$-$C_8$)alkyl, aryl($C_1$-$C_8$)alkyl, or Het, wherein aryl is phenyl or naphthyl and said alkyl, cycloalkyl, or aryl is substituted with from 0 to 3 substituents selected from the group consisting of halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, $C(O)R^{10}$, and $CON(R^{10})_2$;

Het is a 5- or 6-membered saturated cyclic ring having 1 or 2 heteroatoms selected from N, O and S, wherein said ring is substituted with from 0 to 3 substituents selected from halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, $C(O)R^{10}$, and $CON(R^{10})_2$;

$R^4$ is H, $C_1$-$C_8$ alkyl, $C_3$-$C_8$ cycloalkyl($C_1$-$C_8$)alkyl, or aryl($C_1$-$C_8$)alkyl; wherein aryl is phenyl or naphthyl and said alkyl, cycloalkyl, or aryl is substituted with from 0 to 3 substituents selected from the group consisting of halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, $C(O)R^{10}$, and $CON(R^{10})_2$;

$R^5$ is H, halo, $OR^{10}$, $C_1$-$C_6$ alkyl, CN, $CF_3$, $SR^{10}$, $SO_2(C_1$-$C_6$ alkyl), $C_3$-$C_8$ cycloalkyl, $C_3$-$C_8$ cycloalkoxy, $C_1$-$C_6$ haloalkyl, $N(R^7)_2$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein said aryl, heteroaryl, heterocyclyl, cycloalkyl, cycloalkoxy, or alkyl is substituted with from 0 to 4 substituents selected from the group consisting of halo, $OR^{10}$, $SR^{10}$, $N(R^7)_2$, $N(C_1-C_6$ alkyl)$O(C_1-C_6$ alkyl), $C_1-C_6$ alkyl, $C_1-C_6$ haloalkyl, halo($C_1-C_6$ alkoxy), $C_3-C_6$ cycloalkyl, $C_3-C_6$ cycloalkoxy, $NO_2$, CN, $CF_3$, $SO_2(C_1-C_6$ alkyl), $NR^{10}SO_2R^6$, $SO_2N(R^6)_2$, $S(O)(C_1-C_6$ alkyl), $NHCOOR^6$, $NHCOR^6$, $NHCONHR^6$, $CO_2R^{10}$, $C(O)R^{10}$, and $CON(R^{10})_2$; wherein 2 adjacent substituents of said cycloalkyl, cycloalkoxy, aryl, heteroaryl or heterocyclyl, if present, are optionally taken together to form a 3- to 6-membered cyclic ring containing from 0 to 3 heteroatoms selected from N, O and S;

$R^6$ is $C_1-C_6$ alkyl, $C_3-C_6$ cycloalkyl, $C_3-C_6$ cycloalkyl($C_1$-$C_5$)alkyl, aryl, aryl($C_1-C_4$)alkyl, heteroaryl, heteroaryl ($C_1-C_4$ alkyl), heterocyclyl, or heterocyclyl($C_1-C_8$ alkyl), wherein said alkyl, cycloalkyl, aryl, heteroaryl, or heterocyclyl is substituted with 0 to 2 W substituents; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

Y is C(=O), $SO_2$, or C(=N—CN);

Z is $C(R^{10})_2$, O, or $N(R^4)$;

M is $C_1-C_{12}$ alkylene, wherein said alkylene is substituted with from 0 to 2 substituents selected from the group consisting of $C_1-C_8$ alkyl, $C_3-C_8$ cycloalkyl($C_1-C_8$ alkyl), and aryl($C_1-C_8$ alkyl); and 2 adjacent substituents of M, if present, are optionally taken together to form a 3- to 6-membered cyclic ring containing from 0 to 3 heteroatoms selected from N, O and S;

each $R^7$ is independently H, $C_1-C_6$ alkyl, $C_3-C_6$ cycloalkyl, $C_3-C_6$ cycloalkyl($C_1-C_5$)alkyl, aryl, aryl($C_1-C_4$)alkyl, heteroaryl, heteroaryl($C_1-C_4$ alkyl), heterocyclyl, or heterocyclyl($C_1-C_8$ alkyl), wherein said alkyl, cycloalkyl, aryl, heteroaryl, or heterocyclyl is substituted with from 0 to 2 W substituents; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

each W is independently halo, $OR^{10}$, $C_1-C_6$ alkyl, CN, $CF_3$, $NO_2$, $SR^{10}$, $CO_2R^{10}$, $CON(R^{10})_2$, $C(O)R^{10}$, $N(R^{10})C(O)R^{10}$, $SO_2(C_1-C_6$ alkyl), $S(O)(C_1-C_6$ alkyl), $C_3-C_8$ cycloalkyl, $C_3-C_8$ cycloalkoxy, $C_1-C_6$ haloalkyl, $N(R^{10})_2$, $N(C_1-C_6$ alkyl)$O(C_1-C_6$ alkyl), halo($C_1-C_6$ alkoxy), $NR^{10}SO_2R^{10}$, $SO_2N(R^{10})_2$, $NHCOOR^{10}$, $NHCONHR^{10}$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen;

$R^8$ is $C_1-C_8$ alkyl, $C_3-C_8$ cycloalkyl, $C_3-C_8$ cycloalkyl($C_1$-$C_8$ alkyl), aryl, aryl($C_1-C_4$ alkyl), heteroaryl, heterocyclyl, heteroaryl($C_1-C_4$ alkyl), or heterocyclyl($C_1-C_8$ alkyl), wherein said alkyl, cycloalkyl, aryl, heteroaryl or heterocyclyl is substituted with from 0 to 4 substituents selected from the group consisting of aryl, $C_3-C_8$ cycloalkyl, heteroaryl, heterocyclyl, $C_1-C_6$ alkyl, halo ($C_1-C_6$ alkoxy), halo, $OR^{10}$, $SR^{10}$, $N(R^{10})_2$, $N(C_1-C_6$ alkyl)$O(C_1-C_6$ alkyl), $C_1-C_6$ alkyl, $C(O)R^{10}$, $C_1-C_6$ haloalkyl, $NO_2$, CN, $CF_3$, $SO_2(C_1-C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, and $C(O)N(R^{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein 2 adjacent substituents of said cycloalkyl, cycloalkoxy, aryl, heteroaryl or heterocyclyl, if present, are optionally taken together to form a 3- to 6-membered cyclic ring containing from 0 to 3 heteroatoms selected from N, O and S;

$R^9$ is $C_1-C_8$ alkyl, $C_3-C_8$ cycloalkyl, $C_3-C_8$ cycloalkyl($C_1$-$C_8$ alkyl), $C_1-C_8$ alkoxy, $C_3-C_8$ cycloalkoxy, aryl, aryl ($C_1-C_4$ alkyl), heteroaryl, heterocyclyl, heteroaryl($C_1$-$C_4$ alkyl), or heterocyclyl($C_1-C_8$ alkyl), wherein said alkyl, cycloalkyl, alkoxy, cycloalkoxy, aryl, heteroaryl or heterocyclyl is substituted with from 0 to 4 substituents selected from the group consisting of aryl, $C_3-C_8$ cycloalkyl, heteroaryl, heterocyclyl, $C_1-C_6$ alkyl, halo ($C_1-C_6$ alkoxy), halo, $OR^{10}$, $SR^{10}$, $N(R^{10})_2$, $N(C_1-C_6$ alkyl)$O(C_1-C_6$ alkyl), $C_1-C_6$ alkyl, $C(O)R^{10}$, $C_1-C_6$ haloalkyl, $NO_2$, CN, $CF_3$, $SO_2(C_1-C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, and $C(O)N(R^{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein 2 adjacent substituents of said cycloalkyl, cycloalkoxy, aryl, heteroaryl or heterocyclyl, if present, are optionally taken together to form a 3- to 6-membered cyclic ring containing from 0 to 3 heteroatoms selected from N, O and S;

or $R^8$ and $R^9$ are optionally taken together, with the nitrogen atom to which they are attached, to form a 4- to 8-membered monocyclic ring containing from 0 to 2 additional heteroatoms selected from N, O and S; and each $R^{10}$ is independently H or $C_1-C_6$ alkyl;

said process comprising a) coupling a compound of structural formula IA with a compound of structural formula IB to form a compound of structural formula IC

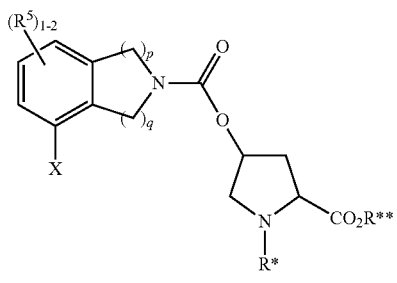 IA

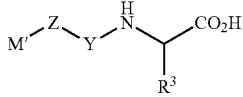 IB

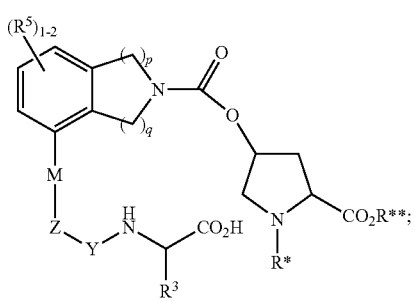 IC wherein
- R* is selected from the group consisting of carbobenzyloxy and tert-butyloxycarbonyl;
- R** is selected from the group consisting of $C_1$-$C_8$ alkyl;
- X is selected from the group consisting of halides and sulfonides; and
- M' is a $C_2$-$C_{12}$ alkyl group containing from 0 to 2 double bonds and 0 to 1 triple bonds, wherein one of said double bonds or triple bonds is between $C_1$ and $C_2$ of said M' and said $C_2$-$C_{12}$ alkyl group is substituted with from 0 to 2 substituents selected from the group consisting of $C_1$-$C_8$ alkyl, $C_3$-$C_8$ cycloalkyl($C_1$-$C_8$ alkyl), and aryl($C_1$-$C_8$ alkyl); and 2 adjacent substituents of M', if present, are optionally taken together to form a 3- to 6-membered cyclic ring containing from 0 to 3 heteroatoms selected from N, O and S;

b) hydrogenating said compound of structural formula IC to form a compound of structural formula ID

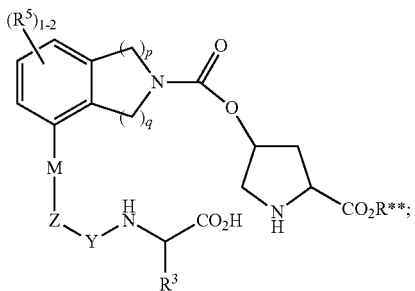 ID c) cyclizing said compound of structural formula ID to form a compound of structural formula IE

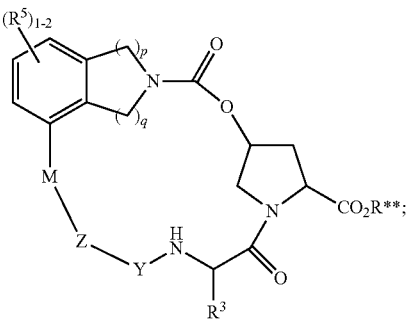 IE d) hydrolyzing the compound of structural formula IE to provide a compound of structural formula IF

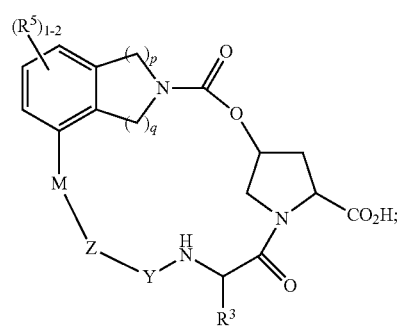 IF and
e) reacting said compound of structural formula IF with a compound of structural formula IG to provide the compound of Formula I;

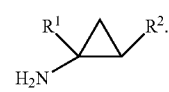 IG

2. The process according to claim 1, wherein X is selected from the group consisting of chloride, bromide, iodide, methane sulfonate, trifluoromethane sulfonate, and aryl sulfonates.

3. The process according to claim 2, wherein M' contains from 1 to 2 double bonds, wherein one of said double bonds, and said coupling comprises reacting said compound of structural formula IB with said compound of the structural formula IC in the presence of a palladium-based catalyst.

4. The process according to claim 3, wherein said palladium-based catalyst is a palladium complex.

5. The process according to claim 4, wherein said palladium complex is a palladium-phosphine complex.

6. The process according to claim 3, wherein said palladium-based catalyst is selected from the group consisting of tetrakis(triphenylphosphine)palladium(0), bis(triphenylphosphine)palladium(II)chloride, bis(triphenylphosphine)palladium(II)acetate, bis(tri-tert-butylphosphine)palladium(0), bis(tricyclohexylphosphine)palladium(0), palladium bis(diphenylphosphinyl ferrocene) dichloride, palladium bis-(di-tert-butylphosphineyl ferrocene)dichloride, palladium(II)acetate, palladium(II)chloride, bis(benzonitrile)palladium(II)chloride, tris(dibenzylideneacetone)dipalladium(0), bis(dibenzylideneacetone)dipalladium, and palladium on carbon.

7. The process according to claim 1, wherein M' contains from 0 or 1 double bond and 1 triple bond, wherein said double triple bond is between $C_1$ and $C_2$ of said M', and said coupling comprises reacting said compound of structural formula IB with a compound of said structural formula IC in the presence of a palladium-based catalyst and a copper salt.

8. The process according to claim 7, wherein said palladium-based catalyst is a palladium complex.

9. The process according to claim 7, wherein the palladium-based catalyst is selected from the group consisting of tetrakis(triphenylphosphine)palladium(0), bis(triphenylphosphine)palladium(II)chloride, bis(triphenylphosphine)palladium(II)acetate, bis(tri-t-butylphosphine)palladium(0), bis(tricyclohexylphosphine)palladium(0), palladium bis(diphenylphosphinyl ferrocene) dichloride, palladium bis-(di-t-butylphosphineyl ferrocene)dichloride, palladium(II)acetate, palladium(II)chloride, bis(benzonitrile) palladium(II)chloride, tris(dibenzylideneacetone) dipalladium(0), bis(dibenzylideneacetone)dipalladium, 2-dicyclohexyl phosphine-2',4',6'-triisopropyl biphenyl and palladium on carbon.

10. The process according to claim 7, wherein said copper salt is selected from the group consisting of copper(I) salts.

11. The process according to claim 10, wherein said copper (I) salt is selected from the group consisting of copper(I) bromide, copper(I) chloride, copper(I)iodide and copper(I) trifluoromethane sulfonate.

12. The process according to claim 11, wherein said copper (I) salt is selected from the group consisting of copper(I) iodide.

13. The process according to claim 1, wherein said hydrogenating of step b comprises reacting said compound of structural formula IC with hydrogen gas in the presence of a catalyst.

14. The process according to claim 13, wherein said catalyst is palladium on carbon.

15. The process according to claim 13, wherein said hydrogenating is conducted at a temperature of from 10° C. to 50° C. and said hydrogen gas is provided at a pressure of from 5 psi to 100 psi.

16. The process according to claim 1, wherein R* is tert-butyloxycarbonyl, and said hydrogenating of step b comprises reacting said compound of structural formula IC with an acid to produce a compound of structural formula IC'

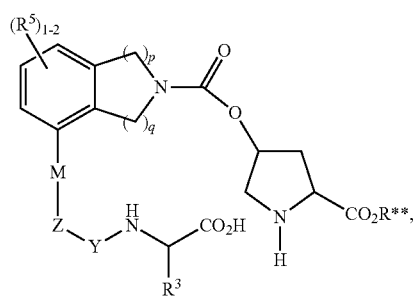

(IC')

and hydrogenating said compound of structural formula IC' to produce the compound of structural formula ID.

17. The process according to claim 16, wherein said acid is selected from the group consisting of methanesulfonic acid and trifluoroacetic acid.

18. The process according to claim 1, wherein said cyclizing of step c comprises reacting said compound of structural formula ID with N-(3-dimethylaminopropyl)-N'-ethylcarbodiimide or O-(7-azabenzotriazol-1-yl)-N,N,N',N'-tetramethyluronium dexafluorophosphate.

19. The process according to claim 1, wherein
p and q are both 1;
$R^1$ is $CONR^{10}SO_2R^6$;
$R^2$ is —$CH_2CH_3$;
$R^3$ is tert-butyl;
$R^5$ is H;
$R^6$ is cyclopropyl;
Y is C(=O);
Z is O;
M is $C_1$-$C_8$ alkylene; and
$R^{10}$ is H.

20. The process according to claim 19, wherein the compound of Formula I is:

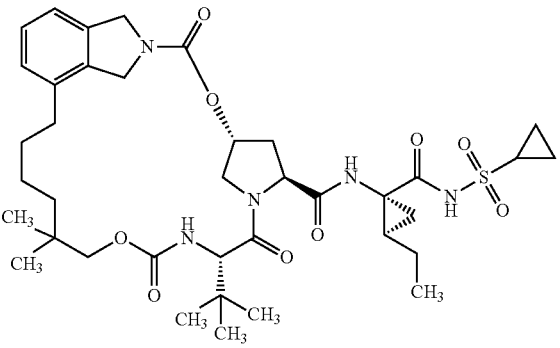

III-205 or a pharmaceutically acceptable salt, solvate or hydrate thereof.

21. The process according to claim 1, wherein the pharmaceutically acceptable salts of the compound of Formula I are selected from the group consisting of aluminum salts, ammonium salts, calcium salts, copper salts, ferric salts, ferrous salts, lithium salts, magnesium salts, manganic salts, manganous salts, potassium salts, sodium salts, zinc salts, salts of primary amines, salts of secondary amines, salts of tertiary amines, salts of substituted amines, salts of cyclic amines, arginine salts, betaine salts, caffeine salts, choline salts, N,N'-dibenzylethylenediamine salts, diethylamine salts, 2-diethylaminoethanol salts, 2-dimethylaminoethanol salts, ethanolamine salts, ethylenediamine salts, N-ethyl-morpholine salts, N-ethylpiperidine salts, glucamine salts, glucosamine salts, histidine salts, hydrabamine salts, isopropylamine salts, lysine salts, methylglucamine salts, morpholine salts, piperazine salts, piperidine salts, polyamine resin salts, procaine salts, purine salts, theobromine salts, triethylamine salts, trimethylamine salts, tripropylamine salts, tromethamine salts, acetic acid salts, benzenesulfonic acid salts, benzoic acid salts, camphorsulfonic acid salts, citric acid salts, ethanesulfonic acid salts, formic acid salts, fumaric acid salts, gluconic acid salts, glutamic acid salts, hydrobromic acid salts, hydrochloric acid salts, isethionic acid salts, lactic acid salts, maleic acid salts, malic acid salts, mandelic acid salts, methanesulfonic acid salts, malonic acid salts, mucic acid salts, nitric acid salts, pamoic acid salts, pantothenic acid salts, phosphoric acid salts, propionic acid salts, succinic acid salts, sulfuric acid salts, tartaric acid salts, p-toluenesulfonic acid salts and trifluoroacetic acid salts.

22. The process according to claim 21, wherein the pharmaceutically acceptable salt of the compound of Formula I is selected from the group consisting of potassium salts and sodium salts.

23. The process according to claim 22, wherein the pharmaceutically acceptable salt is a sodium or potassium salt of a compound of Formula III-205:

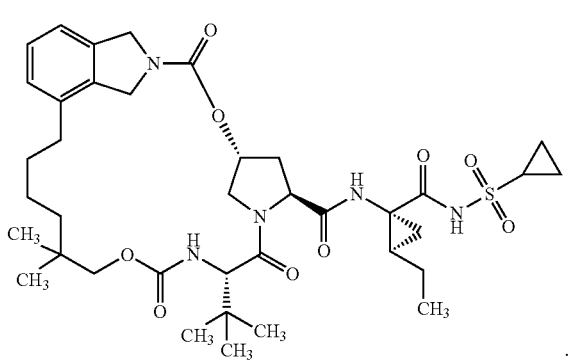

III-205

24. A compound prepared by the process according to claim 1, wherein the compound is selected from the group consisting of:
- a stable crystalline ethanol solvate of a potassium salt of Compound III-205 having an x-ray powder diffraction comprising 2Θ values in degrees of about 6.1±0.1, 8.7±0.1 and 12.3±0.1, when copper K-ALPHA radiation is used as the radiation source;
- a stable crystalline ethanol solvate of a potassium salt of Compound III-205 having an x-ray powder diffraction comprising 2Θ values in degrees of about 7.4±0.1, 8.2±0.1 and 15.1±0.1, when copper K-ALPHA radiation is used as the radiation source;
- a stable crystalline hydrate of a potassium salt of Compound III-205 having an x-ray powder diffraction comprising 2Θ values in degrees of about 6.3±0.1, 8.9±0.1 and 19.6±0.1, when copper K-ALPHA radiation is used as the radiation source;
- a stable crystalline hydrate of a potassium salt of Compound III-205 having an x-ray powder diffraction comprising 2Θ values in degrees of about 6.2±0.1, 12.4±0.1 and 14.8±0.1, when copper K-ALPHA radiation is used as the radiation source;
- a stable crystalline hydrate of a potassium salt of Compound III-205 having an x-ray powder diffraction comprising 2Θ values in degrees of about 8.7±0.1, 16.2±0.1 and 19.4±0.1, when copper K-ALPHA radiation is used as the radiation source;
- a stable crystalline hydrate of a potassium salt of Compound III-205 having an x-ray powder diffraction comprising 2Θ values in degrees of about 8.6±0.1, 16.3±0.1 and 18.9±0.1, when copper K-ALPHA radiation is used as the radiation source;
- a stable crystalline hydrate of a potassium salt of Compound III-205 having an x-ray powder diffraction comprising 2Θ values in degrees of about 8.7±0.1, 18.0±0.1 and 18.6±0.1, when copper K-ALPHA radiation is used as the radiation source;
- a stable crystalline ethyl acetate solvate of a free acid of Compound III-205 having an x-ray powder diffraction comprising 2Θ values in degrees of about 4.4±0.1, 16.0±0.1 and 17.7±0.1, when copper K-ALPHA radiation is used as the radiation source;
- a stable crystalline hydrate of a free acid of Compound III-205 having an x-ray powder diffraction comprising 2Θ values in degrees of about 11.84±0.1, 16.5±0.1 and 18.1±0.1, when copper K-ALPHA radiation is used as the radiation source;
- a stable crystalline heptane solvate of a free acid of Compound III-205 having an x-ray powder diffraction comprising 2Θ values in degrees of about 17.0±0.1, 18.3±0.1 and 20.3±0.1, when copper K-ALPHA radiation is used as the radiation source; and
- a stable crystalline anhydrate of a free acid of Compound III-205 having an x-ray powder diffraction comprising 2Θ values in degrees of about 11.2±0.1, 14.2±0.1 and 20.6±0.1, when copper K-ALPHA radiation is used as the radiation source.

25. The compound of claim 24, wherein the compound is selected from the group consisting of:
- a stable crystalline ethanol solvate of a potassium salt of Compound III-205 having an x-ray powder diffraction comprising 2Θ values in degrees of about 6.1±0.1, 7.1±0.1, 8.7±0.1, 10.3±0.1, 12.3±0.1, 13.6±0.1, 16.1±0.1, 20.9±0.1 and 22.1±0.1, when copper K-ALPHA radiation is used as the radiation source;
- a stable crystalline ethanol solvate of a potassium salt of Compound III-205 having an x-ray powder diffraction comprising 2Θ values in degrees of about 4.5±0.1, 6.1±0.1, 7.4±0.1, 8.2±0.1, 10.4±0.1, 15.1±0.1, 16.2±0.1, 18.9±0.1 and 20.8±0.1, when copper K-ALPHA radiation is used as the radiation source;
- a stable crystalline hydrate of a potassium salt of Compound III-205 having an x-ray powder diffraction comprising 2Θ values in degrees of about 6.3±0.1, 7.3±0.1, 8.9±0.1, 9.7±0.1, 10.6±0.1, 13.9±0.1, 14.6±0.1, 16.0±0.1, 18.0±0.1 and 19.6±0.1, when copper K-ALPHA radiation is used as the radiation source;
- a stable crystalline hydrate of a potassium salt of Compound III-205 having an x-ray powder diffraction comprising 2Θ values in degrees of about 6.2±0.1, 7.4±0.1, 12.4±0.1, 14.8±0.1, 17.3±0.1 and 20.4±0.1, when copper K-ALPHA radiation is used as the radiation source;
- a stable crystalline hydrate of a potassium salt of Compound III-205 having an x-ray powder diffraction comprising 2Θ values in degrees of about 6.1±0.1, 7.2±0.1, 8.7±0.1, 10.4±0.1, 12.3±0.1, 14.9±0.1, 16.2±0.1, 17.8±0.1, 19.4±0.1 and 24.7±0.1, when copper K-ALPHA radiation is used as the radiation source;
- a stable crystalline hydrate of a potassium salt of Compound III-205 having an x-ray powder diffraction comprising 2Θ values in degrees of about 4.7±0.1, 6.3±0.1, 8.1±0.1, 8.6±0.1, 12.4±0.1, 15.2±0.1, 16.3±0.1, 17.2±0.1, 18.9±0.1 and 23.4±0.1, when copper K-ALPHA radiation is used as the radiation source;
- a stable crystalline hydrate of a potassium salt of Compound III-205 having an x-ray powder diffraction comprising 2Θ values in degrees of about 8.7±0.1, 9.9±0.1, 11.2±0.1, 12.9±0.1, 13.9±0.1, 14.5±0.1, 18.0±0.1, 18.6±0.1 and 22.4±0.1, when copper K-ALPHA radiation is used as the radiation source;
- a stable crystalline ethyl acetate solvate of a free acid of Compound III-205 having an x-ray powder diffraction comprising 2Θ values in degrees of about 4.4±0.1, 11.6±0.1, 11.8±0.1, 13.2±0.1, 13.7±0.1, 14.5±0.1, 16.0±0.1, 16.4±0.1, 17.7±0.1 and 18.4±0.1, when copper K-ALPHA radiation is used as the radiation source;

a stable crystalline hydrate of a free acid of Compound III-205 having an x-ray powder diffraction comprising 2Θ values in degrees of about 9.1±0.1, 11.8±0.1, 12.2±0.1, 14.4±0.1, 16.5±0.1, 18.1±0.1, 18.5±0.1, 18.6±0.1, 22.0±0.1 and 22.7±0.1, when copper K-ALPHA radiation is used as the radiation source;

a stable crystalline heptane solvate of a free acid of Compound III-205 having an x-ray powder diffraction comprising 2Θ values in degrees of about 10.9±0.1, 12.5±0.1, 15.9±0.1, 16.5±0.1, 17.0±0.1, 18.3±0.1, 19.5±0.1, 20.3±0.1, 21.9±0.1 and 22.3±0.1, when copper K-ALPHA radiation is used as the radiation source; and a stable crystalline anhydrate of a free acid of Compound III-205 having an x-ray powder diffraction comprising 2Θ values in degrees of about 2.4±0.1, 3.9±0.1, 11.2±0.1, 14.2±0.1, 16.4±0.1, 17.2±0.1, 19.1±0.1, 20.1±0.1, 20.6±0.1 and 22.1±0.1, when copper K-ALPHA radiation is used as the radiation source.

26. The compound of claim 25, wherein the compound is selected from the group consisting of:

a stable crystalline ethanol solvate of a potassium salt of Compound III-205 having an x-ray powder diffraction comprising 2Θ values in degrees of 6.1, 7.1, 8.7, 10.3, 12.3, 13.6, 16.1, 20.9 and 22.1, when copper K-ALPHA radiation is used as the radiation source;

a stable crystalline ethanol solvate of a potassium salt of Compound III-205 having an x-ray powder diffraction comprising 2Θ values in degrees of 4.5, 6.1, 7.4, 8.2, 10.4, 15.1, 16.2, 18.9 and 20.8, when copper K-ALPHA radiation is used as the radiation source;

a stable crystalline hydrate of a potassium salt of Compound III-205 having an x-ray powder diffraction comprising 2Θ values in degrees of 6.3, 7.3, 8.9, 9.7, 10.6, 13.9, 14.6, 16.0, 18.0 and 19.6, when copper K-ALPHA radiation is used as the radiation source;

a stable crystalline hydrate of a potassium salt of Compound III-205 having an x-ray powder diffraction comprising 2Θ values in degrees of 6.2, 7.4, 12.4, 14.8, 17.3 and 20.4, when copper K-ALPHA radiation is used as the radiation source;

a stable crystalline hydrate of a potassium salt of Compound III-205 having an x-ray powder diffraction comprising 2Θ values in degrees of 6.1, 7.2, 8.7, 10.4, 12.3, 14.9, 16.2, 17.8, 19.4 and 24.7, when copper K-ALPHA radiation is used as the radiation source;

a stable crystalline hydrate of a potassium salt of Compound III-205 having an x-ray powder diffraction comprising 2Θ values in degrees of 4.7, 6.3, 8.1, 8.6, 12.4, 15.2, 16.3, 17.2, 18.9 and 23.4, when copper K-ALPHA radiation is used as the radiation source;

a stable crystalline hydrate of a potassium salt of Compound III-205 having an x-ray powder diffraction comprising 2Θ values in degrees of 8.7, 9.9, 11.2, 12.9, 13.9, 14.5, 18.0, 18.6 and 22.4, when copper K-ALPHA radiation is used as the radiation source;

a stable crystalline ethyl acetate solvate of a free acid of Compound III-205 having an x-ray powder diffraction comprising 2Θ values in degrees of 4.4, 11.6, 11.8, 13.2, 13.7, 14.5, 16.0, 16.4, 17.7 and 18.4, when copper K-ALPHA radiation is used as the radiation source;

a stable crystalline hydrate of a free acid of Compound III-205 having an x-ray powder diffraction comprising 2Θ values in degrees of 9.1, 11.8, 12.2, 14.4, 16.5, 18.1, 18.5, 18.6, 22.0 and 22.7, when copper K-ALPHA radiation is used as the radiation source;

a stable crystalline heptane solvate of a free acid of Compound III-205 having an x-ray powder diffraction comprising 2Θ values in degrees of 10.9, 12.5, 15.9, 16.5, 17.0, 18.3, 19.5, 20.3, 21.9 and 22.3, when copper K-ALPHA radiation is used as the radiation source; and a stable crystalline anhydrate of a free acid of Compound III-205 having an x-ray powder diffraction comprising 2Θ values in degrees of 2.4, 3.9, 11.2, 14.2, 16.4, 17.2, 19.1, 20.1, 20.6 and 22.1, when copper K-ALPHA radiation is used as the radiation source.

* * * * *